US011564761B2

(12) United States Patent
Rohs et al.

(10) Patent No.: US 11,564,761 B2
(45) Date of Patent: Jan. 31, 2023

(54) SYSTEMS AND METHODS FOR CONTROLLING MOVEMENT OF A SURGICAL TOOL ALONG A PREDEFINED PATH

(71) Applicant: MAKO Surgical Corp., Ft. Lauderdale, FL (US)

(72) Inventors: Helmut Rohs, Freiburg (DE); Michael Dale Dozeman, Portage, MI (US); Bharat Arora, San Francisco, CA (US); Michael Ferko, Warwick, NY (US); Patrick Roessler, Merzhausen (DE); Richard Thomas DeLuca, Kalamazoo, MI (US); David Gene Bowling, Los Ranchos De Albuquerque, NM (US)

(73) Assignee: MAKO Surgical Corp., Ft, Lauderdale, FL (US)

( * ) Notice: Subject to any disclaimer, the term of this patent is extended or adjusted under 35 U.S.C. 154(b) by 365 days.

(21) Appl. No.: 16/811,909

(22) Filed: Mar. 6, 2020

(65) Prior Publication Data

US 2020/0281676 A1 Sep. 10, 2020

Related U.S. Application Data

(60) Provisional application No. 62/896,394, filed on Sep. 5, 2019, provisional application No. 62/815,739, filed on Mar. 8, 2019.

(51) Int. Cl.
*A61B 34/00* (2016.01)
*A61B 34/10* (2016.01)
(Continued)

(52) U.S. Cl.
CPC .............. *A61B 34/76* (2016.02); *A61B 34/10* (2016.02); *A61B 34/20* (2016.02); *A61B 34/37* (2016.02);
(Continued)

(58) Field of Classification Search
None
See application file for complete search history.

(56) References Cited

U.S. PATENT DOCUMENTS 5,261,895 A 11/1993 Kablik
6,298,262 B1 10/2001 Franck et al.
(Continued)

FOREIGN PATENT DOCUMENTS

| WO | 2008031077 A3 | 5/2008 |
| WO | 2014151550 A2 | 9/2014 |
| WO | 2016187290 A1 | 11/2016 |

OTHER PUBLICATIONS

B. Davies, "Active Constraints for Robotic Knee Surgery", May 4, 2006, The Institution of Engineering and Technology Robotics & Mechatronics Network, pp. 31-48 (Year: 2006).*
(Continued)

*Primary Examiner* — Tamara L Weber
(74) *Attorney, Agent, or Firm* — Howard & Howard Attorneys PLLC

(57) ABSTRACT

A robotic surgical system comprises a surgical tool, a manipulator configured to support the surgical tool, a force/torque sensor to measure forces and torques applied to the surgical tool, and a control system. The control system obtains a three-dimensional milling path for the surgical tool. The control system also receives one or more signals from the force/torque sensor in response to a user manually applying user forces and torques to the surgical tool. The control system determines a commanded pose to which to command the manipulator to advance the surgical tool along the milling path based on a tangential component of the user forces and torques, based on a virtual simulation using virtual constraints, and/or based on other suitable factors to promote guided, manual movement of the surgical tool along the milling path.

30 Claims, 40 Drawing Sheets

(51) Int. Cl.
*A61B 34/20* (2016.01)
*A61B 34/37* (2016.01)

(52) U.S. Cl.
CPC ........ *A61B 34/74* (2016.02); *A61B 2034/107* (2016.02); *A61B 2034/108* (2016.02); *A61B 2034/2046* (2016.02)

(56) References Cited

U.S. PATENT DOCUMENTS

| | | | |
|---|---|---|---|
| 6,406,472 | B1 | 6/2002 | Jensen |
| 6,792,398 | B1* | 9/2004 | Handley ............. G06F 3/03545 703/2 |
| 7,035,716 | B2 | 4/2006 | Harris et al. |
| 7,831,292 | B2 | 11/2010 | Quaid et al. |
| 8,010,180 | B2 | 8/2011 | Quaid et al. |
| 8,398,541 | B2 | 3/2013 | DiMaio et al. |
| 8,433,389 | B2 | 4/2013 | Geiger et al. |
| 8,551,115 | B2 | 10/2013 | Steger et al. |
| 9,008,757 | B2 | 4/2015 | Wu |
| 9,119,695 | B2 | 9/2015 | Reinbold |
| 9,125,699 | B2 | 9/2015 | Zahrly et al. |
| 9,179,832 | B2 | 11/2015 | Diolaiti |
| 9,283,050 | B2 | 3/2016 | Prisco et al. |
| 9,566,122 | B2 | 2/2017 | Bowling et al. |
| 2002/0035400 | A1 | 3/2002 | Bryan et al. |
| 2004/0068172 | A1 | 4/2004 | Nowinski et al. |
| 2005/0234465 | A1 | 10/2005 | McCombs et al. |
| 2007/0021738 | A1 | 1/2007 | Hasser et al. |
| 2007/0142751 | A1* | 6/2007 | Kang ..................... A61B 34/20 600/587 |
| 2008/0010706 | A1 | 1/2008 | Moses et al. |
| 2009/0248038 | A1* | 10/2009 | Blumenkranz ........ A61B 34/30 606/130 |
| 2012/0059378 | A1* | 3/2012 | Farrell .................. A61B 90/25 606/80 |
| 2012/0330429 | A1 | 12/2012 | Axelson, Jr. et al. |
| 2013/0245375 | A1 | 9/2013 | DiMaio et al. |
| 2014/0088410 | A1 | 3/2014 | Wu |
| 2014/0276949 | A1 | 9/2014 | Staunton et al. |
| 2014/0276954 | A1 | 9/2014 | Hourtash |
| 2015/0100066 | A1* | 4/2015 | Kostrzewski .......... A61B 34/20 606/130 |
| 2015/0265358 | A1* | 9/2015 | Bowling ................ A61B 17/16 700/261 |
| 2015/0289941 | A1* | 10/2015 | Bowling .................. B25J 13/00 606/130 |
| 2015/0342690 | A1 | 12/2015 | Zubiate et al. |
| 2015/0374446 | A1 | 12/2015 | Malackowski et al. |
| 2016/0100900 | A1 | 4/2016 | Madhani et al. |
| 2018/0353253 | A1 | 12/2018 | Bowling |

OTHER PUBLICATIONS

Marijn Tamis; Comparison between Projected Gauss-Seidel and Sequential Impulse Solvers for Real-Time Physics Simulations; Jul. 1, 2015; v1.01; 11 pages.

Marijn Tamis et al.; Constraint based physics solver; Jun. 15, 2015; v1.02; 31 pages.

Catto, Erin et al., "Modeling and Solving Constraints", 2018, 81 pages.

Constantinescu, Daniela et al., "Haptic Rendering of Rigid Contacts Using Impulsive and Penalty Forces", fransations on Robotics, Mar. 4, 2004, 14 pages.

Hennekens, D. et al., "Continuous Impulsive Force Controller for Forbidden-Region Virtual Fixtures", IEEE International Conference on Robotics and Automation, 2008, 6 pages.

Yen, P-L, et al., "Active Constraint Control for Image-Guided Robotic Surgery", Proceedings of the Institution of Mechanical Engineers, Part H: Journal of Engineering in Medicine, 2010, pp. 623-631.

* cited by examiner

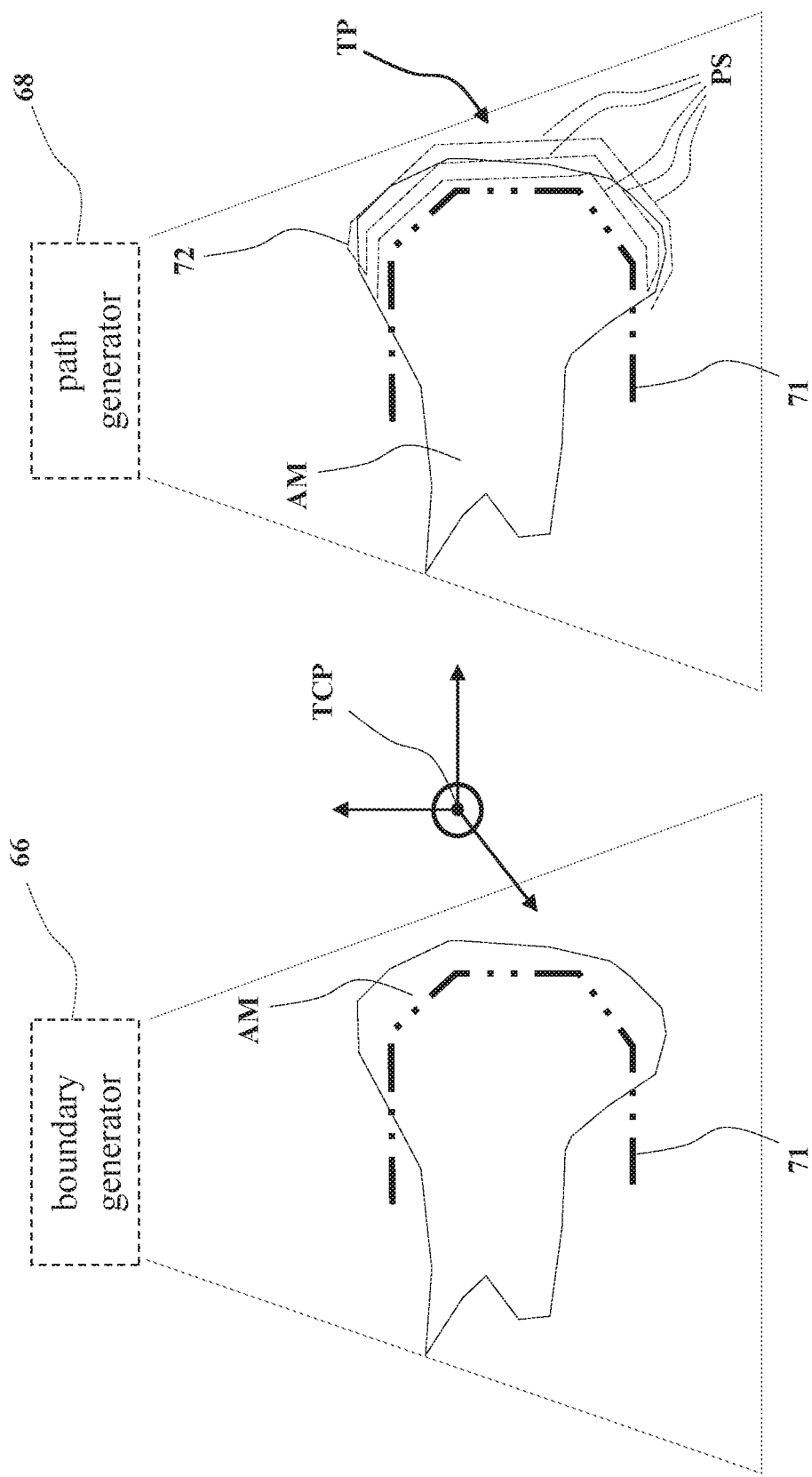

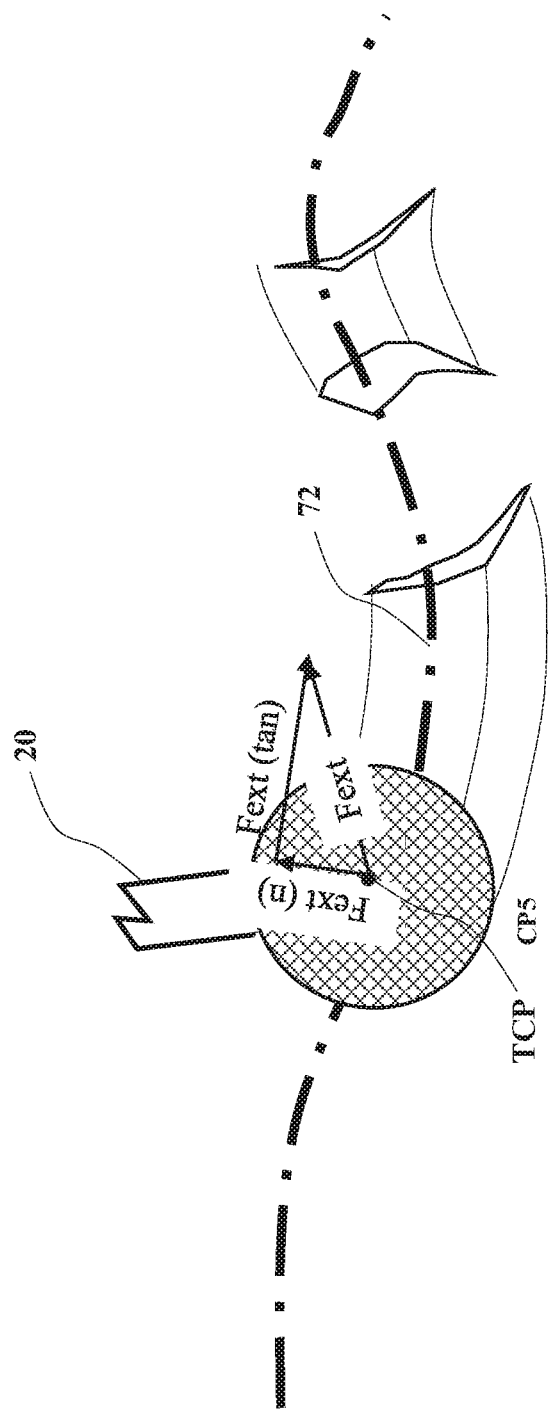

Constraint Equation

- Calculate force for each constraint ($F_{p_i}$) in constraint space by solving system of n linear equations ($Ax = b \rightarrow x = A^{-1}b = F = (M^{-1})^{-1}a$)

$$F_p = \left(J_p M^{-1} J_p^T + \frac{C}{\Delta t}\right)^{-1} \left(\frac{v_{p_2}}{\Delta t} - \frac{J_p v_{cg_1}}{\Delta t} - \frac{\epsilon \Delta d}{\Delta t^2} - \left(J_p M^{-1} + \frac{C}{\Delta t} J_p^{-T}\right)\left(F_{inertial} + F_{damping} + F_{cg_{ext}}\right)\right) \geq 0$$

FIG. 14

Forward Dynamics Algorithm

Configuration Parameters:
Mass matrix, $M_{6DOF}$ [6 × 6] combination of Mass and Inertia [3 × 3] matrices
Velocity Limits, $v_{max}, \omega_{max}$ Inputs:
initial pose, $^{0}_{n}T(t_0)$
initial velocity, $^{n}v(t_0)$
total force applied at CG, $^{n}F_{total}$
time interval, dT Outputs:
final pose, $^{0}_{n}T(t_0 + dT)$
final velocity, $^{n}v(t_0 + dT)$

FIG. 15

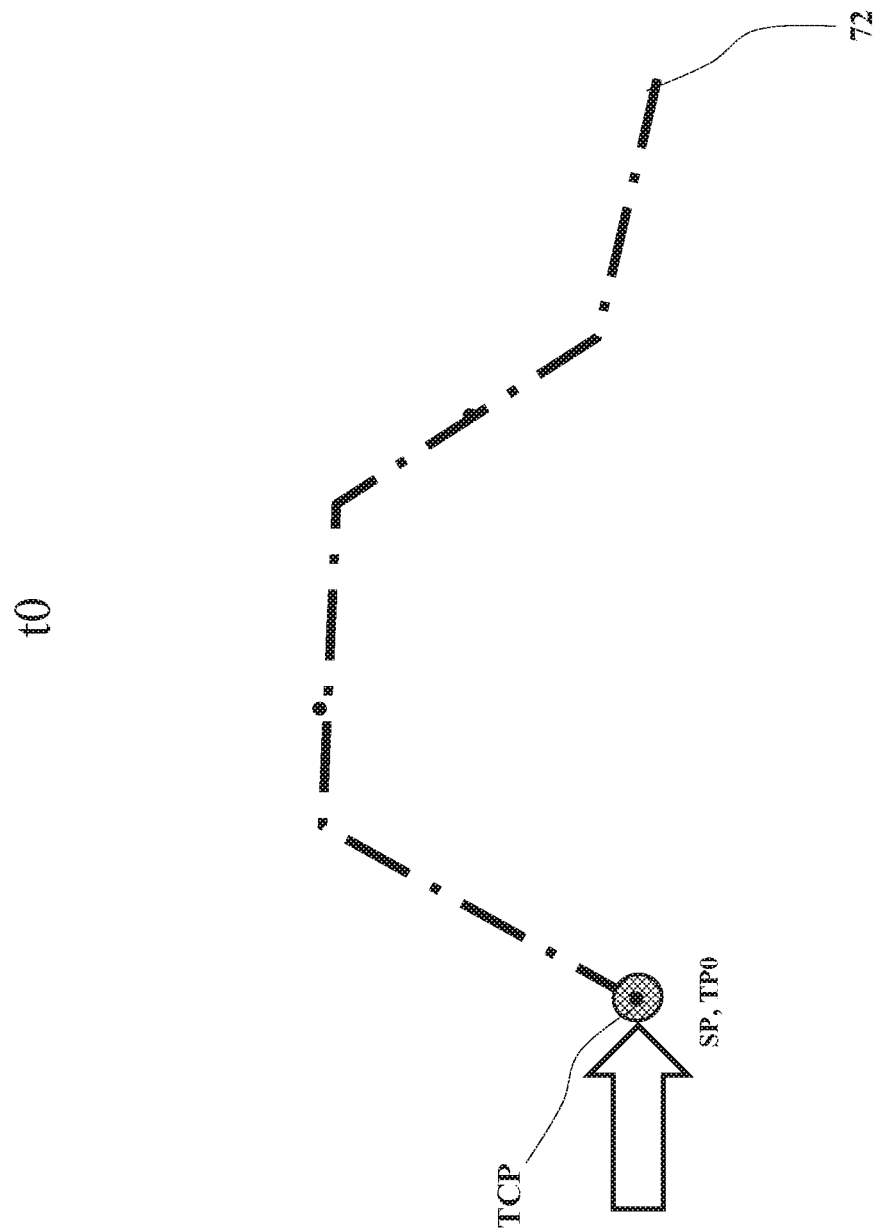

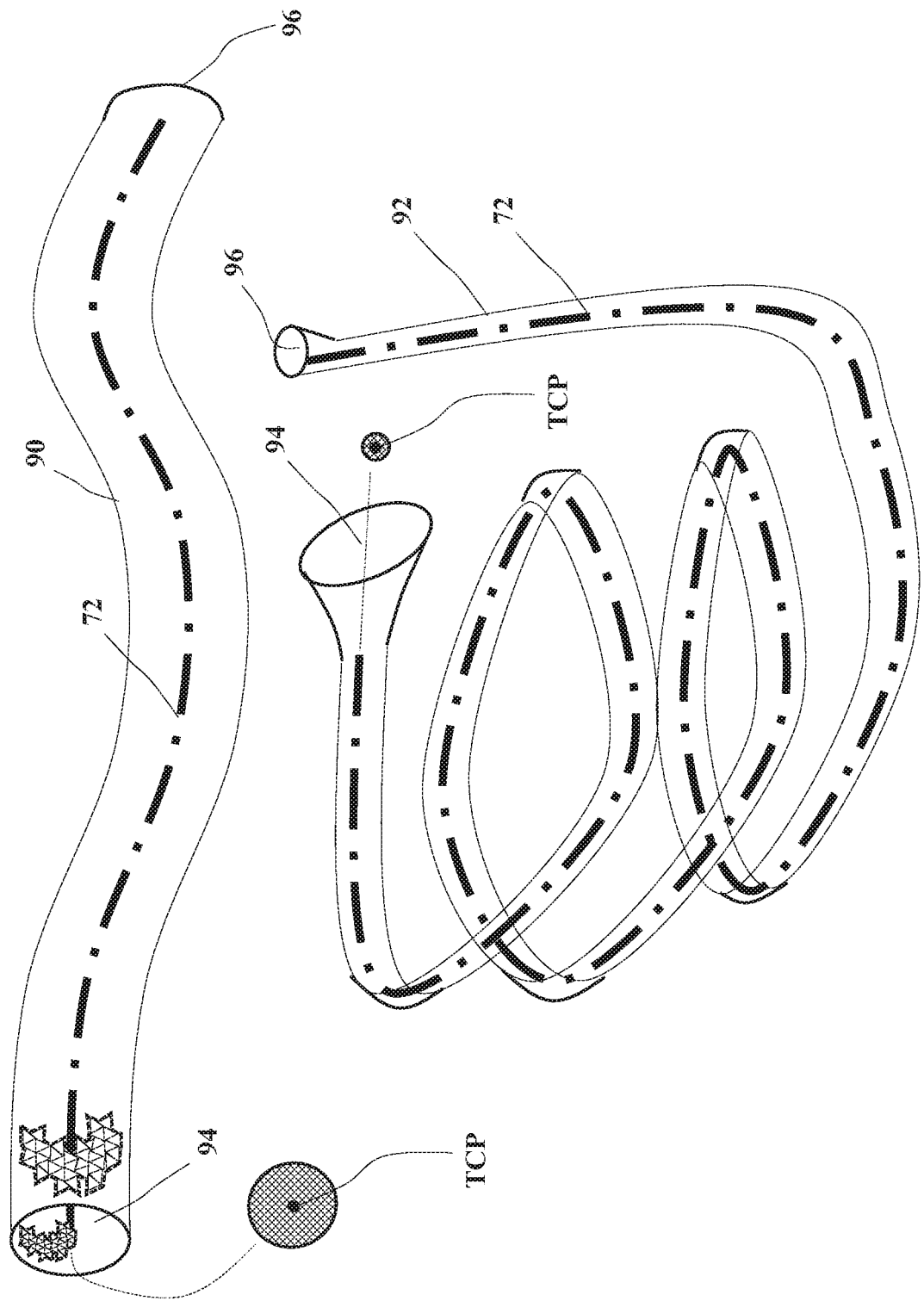

SYSTEMS AND METHODS FOR CONTROLLING MOVEMENT OF A SURGICAL TOOL ALONG A PREDEFINED PATH

CROSS-REFERENCE TO RELATED APPLICATIONS

The subject application claims priority to and all the benefits of U.S. Provisional Patent Application No. 62/815,739, filed Mar. 8, 2019, and U.S. Provisional Patent Application No. 62/896,394, filed Sep. 5, 2019, the contents of each of the above applications being hereby incorporated by reference in their entirety.

TECHNICAL FIELD

The present disclosure relates generally to systems and methods for controlling movement of a surgical tool along a predefined path.

BACKGROUND

Robotic surgical systems perform surgical procedures at surgical sites. Robotic surgical systems typically include a manipulator and an end effector coupled to the manipulator. Often, the end effector comprises a surgical tool to remove tissue at the surgical site.

In a manual mode of operation, one type of robotic surgical system senses forces and torques manually applied to the surgical tool by a user. The robotic surgical system commands positioning of the surgical tool to emulate motion expected by the user from application of the sensed forces and torques. Thus, the robotic surgical system generally positions the surgical tool in accordance with the user's intentions and expectations so that the user, for example, is able to remove a desired volume of tissue. However, in the manual mode, it can be fatiguing for the user to cause movement of the surgical tool as needed to completely remove the entire volume of tissue, especially when the volume of tissue is relatively large compared to the size of the surgical tool. Accordingly, the robotic surgical system is also operable in a semi-autonomous mode in which the robotic surgical system commands the manipulator to move the surgical tool autonomously along a predefined tissue removal path, unassisted by the user. However, when operating in the semi-autonomous mode, there may be a perception that the user has less control over the surgical tool. For this reason, the manual mode may be preferred by some users.

There is a need in the art for systems and methods to address these challenges.

SUMMARY

A robotic surgical system is provided that comprises a surgical tool and a manipulator configured to support the surgical tool. The manipulator comprises a plurality of links. A force/torque sensor measures forces and torques applied to the surgical tool. A control system obtains a milling path for the surgical tool wherein the milling path is three-dimensional. The control system receives input from the force/torque sensor in response to a user manually applying user forces and torques to the surgical tool. The control system calculates a tangential component of force tangential to the milling path based on the input from the force/torque sensor and commands the manipulator to advance the surgical tool along the milling path based on the calculated tangential component.

A method is provided for operating a robotic surgical system. The robotic surgical system comprises a surgical tool, a manipulator configured to support the surgical tool, and a force/torque sensor to measure forces and torques applied to the surgical tool. The method comprises obtaining a milling path for the surgical tool wherein the milling path is three-dimensional. Input from the force/torque sensor is received in response to a user manually applying user forces and torques to the surgical tool. A tangential component of force tangential to the milling path is calculated based on the input from the force/torque sensor so that the manipulator can be commanded to advance the surgical tool along the milling path based on the calculated tangential component.

Another robotic surgical system is provided that comprises a surgical tool and a manipulator configured to support the surgical tool. The manipulator comprises a plurality of links. A force/torque sensor measures forces and torques applied to the surgical tool. A control system obtains a milling path for the surgical tool wherein the milling path is three-dimensional. The control system also defines virtual constraints on movement of the surgical tool along the milling path with respect to two degrees of freedom each being normal to the milling path. The virtual constraints are defined to constrain movement of the surgical tool to be along the milling path. The control system receives input from the force/torque sensor in response to a user manually applying user forces and torques to the surgical tool. The control system simulates dynamics of the surgical tool in a virtual simulation based on the virtual constraints and the input from the force/torque sensor and commands the manipulator to advance the surgical tool along the milling path based on the virtual simulation.

Another method is provided for operating a robotic surgical system. The robotic surgical system comprises a surgical tool, a manipulator configured to support the surgical tool, and a force/torque sensor to measure forces and torques applied to the surgical tool. The method comprises obtaining a milling path for the surgical tool wherein the milling path is three-dimensional. Virtual constraints are defined with respect to two degrees of freedom each being normal to the milling path. The virtual constrains are defined to constrain movement of the surgical tool to be along the milling path. Input from the force/torque sensor is received in response to a user manually applying user forces and torques to the surgical tool. Dynamics of the surgical tool are simulated in a virtual simulation based on the virtual constraints and the input from the force/torque sensor so that the manipulator can be commanded to advance the surgical tool along the milling path based on the virtual simulation.

Another robotic surgical system is provided that comprises a surgical tool and a manipulator configured to support the surgical tool. The manipulator comprises a plurality of links. A force/torque sensor measures forces and torques applied to the surgical tool. A control system obtains a milling path for the surgical tool wherein the milling path is three-dimensional. The control system receives an input from the force/torque sensor in response to user forces and torques manually applied to the surgical tool by a user. The control system calculates a tangential component of force tangential to the milling path based on the input from the force/torque sensor and calculates an effective feed rate for advancing the surgical tool along the milling path based on the calculated tangential component. The control system defines virtual constraints on movement of the surgical tool along the milling path with respect to three degrees of freedom and based on the effective feed rate to promote movement of the surgical tool along the milling path. The control system simulates dynamics of the surgical tool in a virtual simulation based on the virtual constraints and the input from the force/torque sensor and commands the manipulator to advance the surgical tool along the milling path based on the virtual simulation.

Another method is provided for operating a robotic surgical system. The robotic surgical system comprises a surgical tool, a manipulator configured to support the surgical tool, and a force/torque sensor to measure forces and torques applied to the surgical tool. The method comprises obtaining a milling path for the surgical tool wherein the milling path is three-dimensional. Input is received from the force/torque sensor in response to user forces and torques manually applied to the surgical tool by a user. A tangential component of force is calculated tangential to the milling path based on the input from the force/torque sensor. An effective feed rate is calculated based on the calculated tangential component. Virtual constraints are defined with respect to three degrees of freedom and based on the effective feed rate to promote movement of the surgical tool along the milling path. Dynamics of the surgical tool are simulated in a virtual simulation based on the virtual constraints and the input from the force/torque sensor so that the manipulator can be commanded to advance the surgical tool along the milling path based on the virtual simulation.

Another robotic surgical system is provided that comprises a surgical tool and a manipulator configured to support the surgical tool. The manipulator comprises a plurality of links. A force/torque sensor measures forces and torques applied to the surgical tool. A control system obtains a virtual boundary for the surgical tool wherein the virtual boundary is three-dimensional. The virtual boundary comprises a tube defining a milling path for the surgical tool. The control system defines virtual constraints on movement of the surgical tool inside the tube and along the milling path. The virtual constraints are defined to constrain movement of the surgical tool to be along the milling path. The control system receives an input from the force/torque sensor in response to user forces and torques manually applied to the surgical tool by a user. The control system simulates dynamics of the surgical tool in a virtual simulation based on the virtual constraints and the input from the force/torque sensor and commands the manipulator to advance the surgical tool along the milling path based on the virtual simulation.

Another method is provided for operating a robotic surgical system. The robotic surgical system comprises a surgical tool, a manipulator configured to support the surgical tool, and a force/torque sensor to measure forces and torques applied to the surgical tool. The method comprises obtaining a virtual boundary for the surgical tool wherein the virtual boundary is three-dimensional. The virtual boundary comprises a tube defining a milling path for the surgical tool. The method also comprises defining virtual constraints on movement of the surgical tool inside the tube and along the milling path, the virtual constraints being defined to constrain movement of the surgical tool to be along the milling path. Input is received from the force/torque sensor in response to user forces and torques manually applied to the surgical tool by a user. Dynamics of the surgical tool are simulated in a virtual simulation based on the virtual constraints and the input from the force/torque sensor and the manipulator is commanded to advance the surgical tool along the milling path based on the virtual simulation.

DESCRIPTION OF THE DRAWINGS

Advantages of the present disclosure will be readily appreciated as the same becomes better understood by reference to the following detailed description when considered in connection with the accompanying drawings.

FIG. 4 illustrates output of a boundary generator.

FIG. 5 illustrates output of a path generator.

FIGS. 9A-9J illustrate each of the movements of the surgical tool along the milling path shown in FIG. 7.

FIG. 14 shows a sample constraint equation.

FIGS. 15 and 16 show a sample forward dynamics algorithm for carrying out a virtual simulation.

FIGS. 23A-23D illustrate each of the movements of the surgical tool along the milling path shown in FIG. 22.

FIG. 24 illustrates another milling path and a virtual object defining a boundary to keep the surgical tool moving along the milling path, the virtual object being modeled as a triangulated mesh.

FIG. 25 illustrates another milling path and another virtual object defining a boundary to keep the surgical tool moving along the milling path.

DETAILED DESCRIPTION

Figure 1:
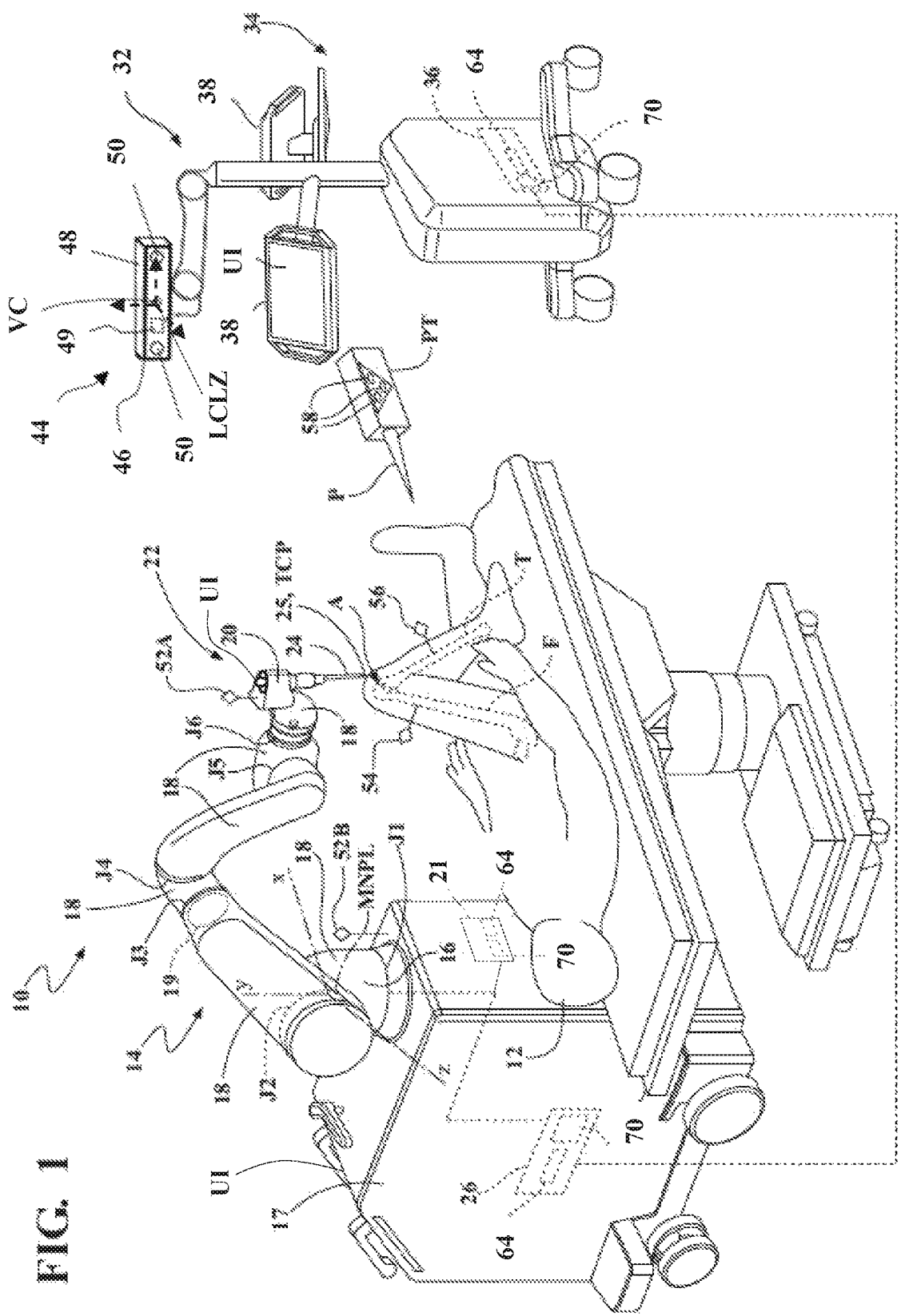
FIG. 1 is a perspective view of a robotic surgical system.

Referring to FIG. 1, a robotic surgical system 10 is illustrated. The system 10 is useful for treating a surgical site or anatomical volume (A) of a patient 12, such as treating bone or soft tissue. In FIG. 1, the patient 12 is undergoing a surgical procedure. The anatomy in FIG. 1 includes a femur F and a tibia T of the patient 12. The surgical procedure may involve tissue removal or other forms of treatment. Treatment may include cutting, coagulating, lesioning the tissue, other in-situ tissue treatments, or the like. In some examples, the surgical procedure involves partial or total knee or hip replacement surgery, shoulder replacement surgery, spine surgery, or ankle surgery. In some examples, the system 10 is designed to cut away material to be replaced by surgical implants, such as hip and knee implants, including unicompartmental, bicompartmental, multicompartmental, or total knee implants. Some of these types of implants are shown in U.S. Patent Application Publication No. 2012/0330429, entitled, "Prosthetic Implant and Method of Implantation," the disclosure of which is hereby incorporated by reference. The system 10 and techniques disclosed herein may be used to perform other procedures, surgical or non-surgical, or may be used in industrial applications or other applications where robotic systems are utilized.

The system 10 includes a manipulator 14. The manipulator 14 has a base 16 and plurality of links 18. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1), a parallel arm configuration, or any other suitable manipulator configuration. In other examples, more than one manipulator 14 may be utilized in a multiple arm configuration.

In the example shown in FIG. 1, the manipulator 14 comprises a plurality of joints J and a plurality of joint encoders 19 located at the joints J for determining position data of the joints J. For simplicity, only one joint encoder 19 is illustrated in FIG. 1, although other joint encoders 19 may be similarly illustrated. The manipulator 14 according to one example has six joints J1-J6 implementing at least six-degrees of freedom (DOF) for the manipulator 14. However, the manipulator 14 may have any number of degrees of freedom and may have any suitable number of joints J and may have redundant joints.

The manipulator 14 need not require joint encoders 19 but may alternatively, or additionally, utilize motor encoders present on motors at each joint J. Also, the manipulator 14 need not require rotary joints, but may alternatively, or additionally, utilize one or more prismatic joints. Any suitable combination of joint types are contemplated.

The base 16 of the manipulator 14 is generally a portion of the manipulator 14 that provides a fixed reference coordinate system for other components of the manipulator 14 or the system 10 in general. Generally, the origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the manipulator cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference pose, which provides both a fixed position and orientation reference and which does not move relative to the manipulator 14 and/or manipulator cart 17. In other examples, the manipulator 14 can be a hand-held manipulator where the base 16 is a base portion of a tool (e.g., a portion held free-hand by the user) and the tool tip is movable relative to the base portion. The base portion has a reference coordinate system that is tracked and the tool tip has a tool tip coordinate system that is computed relative to the reference coordinate system (e.g., via motor and/or joint encoders and forward kinematic calculations). Movement of the tool tip can be controlled to follow the path since its pose relative to the path can be determined.

The manipulator 14 and/or manipulator cart 17 house a manipulator controller 26, or other type of control unit. The manipulator controller 26 may comprise one or more computers, or any other suitable form of controller that directs the motion of the manipulator 14. The manipulator controller 26 may have a central processing unit (CPU) and/or other processors, memory (not shown), and storage (not shown). The manipulator controller 26 is loaded with software as described below. The processors could include one or more processors to control operation of the manipulator 14. The processors can be any type of microprocessor, multi-processor, and/or multi-core processing system. The manipulator controller 26 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor. The manipulator 14 may also comprise a user interface UI with one or more displays and/or input devices (e.g., push buttons, keyboard, mouse, microphone (voice-activation), gesture control devices, touchscreens, etc.).

A tool 20 couples to the manipulator 14 and is movable relative to the base 16 to interact with the anatomy in certain modes. The tool 20 is a physical and surgical tool and is or forms part of an end effector 22 supported by the manipulator 14 in certain embodiments. The tool 20 may be grasped by the user. One possible arrangement of the manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference.

The tool 20 includes an energy applicator 24 designed to contact and remove the tissue of the patient 12 at the surgical site. In one example, the energy applicator 24 is a bur 25. The bur 25 may be substantially spherical and comprise a spherical center, radius (r) and diameter. Alternatively, the energy applicator 24 may be a drill bit, a saw blade, an ultrasonic vibrating tip, or the like. The tool 20 and/or energy applicator 24 may comprise any geometric feature, e.g., perimeter, circumference, radius, diameter, width, length, volume, area, surface/plane, range of motion envelope (along any one or more axes), etc. The geometric feature may be considered to determine how to locate the tool 20 relative to the tissue at the surgical site to perform the desired treatment. In some of the embodiments described herein, a spherical bur having a tool center point (TCP) will be described for convenience and ease of illustration, but is not intended to limit the tool 20 to any particular form.

The tool 20 may comprise a tool controller 21 to control operation of the tool 20, such as to control power to the tool (e.g., to a rotary motor of the tool 20), control movement of the tool 20, control irrigation/aspiration of the tool 20, and/or the like. The tool controller 21 may be in communication with the manipulator controller 26 or other components. The tool 20 may also comprise a user interface UI with one or more displays and/or input devices (e.g., push buttons, keyboard, mouse, microphone (voice-activation), gesture control devices, touchscreens, etc.). The manipulator controller 26 controls a state (position and/or orientation) of the tool 20 (e.g, the TCP) with respect to a coordinate system, such as the manipulator coordinate system MNPL. The manipulator controller 26 can control (linear or angular) velocity, acceleration, or other derivatives of motion of the tool 20.

The tool center point (TCP), in one example, is a predetermined reference point defined at the energy applicator 24. The TCP has a known, or able to be calculated (i.e., not necessarily static), pose relative to other coordinate systems. The geometry of the energy applicator 24 is known in or defined relative to a TCP coordinate system. The TCP may be located at the spherical center of the bur 25 of the tool 20 such that only one point is tracked. The TCP may be defined in various ways depending on the configuration of the energy applicator 24. The manipulator 14 could employ the joint/motor encoders, or any other non-encoder position sensing method, to enable a pose of the TCP to be determined. The manipulator 14 may use joint measurements to determine TCP pose and/or could employ techniques to measure TCP pose directly. The control of the tool 20 is not limited to a center point. For example, any suitable primitives, meshes, etc., can be used to represent the tool 20.

The system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 tracks movement of various objects. Such objects include, for example, the manipulator 14, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformations.

The navigation system 32 includes a cart assembly 34 that houses a navigation controller 36, and/or other types of control units. A navigation user interface UI is in operative communication with the navigation controller 36. The navigation user interface includes one or more displays 38. The navigation system 32 is capable of displaying a graphical representation of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, a keyboard, a mouse, a microphone (voice-activation), gesture control devices, and the like.

The navigation system 32 also includes a navigation localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC.

The navigation system 32 includes one or more trackers. In one example, the trackers include a pointer tracker PT, one or more manipulator trackers 52A, 52B, a first patient tracker 54, and a second patient tracker 56. In the illustrated example of FIG. 1, the manipulator tracker is firmly attached to the tool 20 (i.e., tracker 52A), the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The pointer tracker PT is firmly affixed to a pointer P used for registering the anatomy to the localizer coordinate system LCLZ. The manipulator tracker 52A, 52B may be affixed to any suitable component of the manipulator 14, in addition to, or other than the tool 20, such as the base 16 (i.e., tracker 52B), or any one or more links 18 of the manipulator 14. The trackers 52A, 52B, 54, 56, PT may be fixed to their respective components in any suitable manner. For example, the trackers may be rigidly fixed, flexibly connected (optical fiber), or not physically connected at all (ultrasound), as long as there is a suitable (supplemental) way to determine the relationship (measurement) of that respective tracker to the object that it is associated with.

Any one or more of the trackers may include active markers 58. The active markers 58 may include light emitting diodes (LEDs). Alternatively, the trackers 52A, 52B, 54, 56, PT may have passive markers, such as reflectors, which reflect light emitted from the camera unit 46. Other suitable markers not specifically described herein may be utilized.

The localizer 44 tracks the trackers 52A, 52B, 54, 56, PT to determine a state of each of the trackers 52A, 52B, 54, 56, PT, which correspond respectively to the state of the object respectively attached thereto. The localizer 44 may perform known triangulation techniques to determine the states of the trackers 52, 54, 56, PT, and associated objects. The localizer 44 provides the state of the trackers 52A, 52B, 54, 56, PT to the navigation controller 36. In one example, the navigation controller 36 determines and communicates the state the trackers 52A, 52B, 54, 56, PT to the manipulator controller 26. As used herein, the state of an object includes, but is not limited to, data that defines the position and/or orientation of the tracked object or equivalents/derivatives of the position and/or orientation. For example, the state may be a pose of the object, and may include linear velocity data, and/or angular velocity data, and the like.

The navigation controller 36 may comprise one or more computers, or any other suitable form of controller. Navigation controller 36 has a central processing unit (CPU) and/or other processors, memory (not shown), and storage (not shown). The processors can be any type of processor, microprocessor or multi-processor system. The navigation controller 36 is loaded with software. The software, for example, converts the signals received from the localizer 44 into data representative of the position and orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

Although one example of the navigation system 32 is shown that employs triangulation techniques to determine object states, the navigation system 32 may have any other suitable configuration for tracking the manipulator 14, tool 20, and/or the patient 12. In another example, the navigation system 32 and/or localizer 44 are ultrasound-based. For example, the navigation system 32 may comprise an ultrasound imaging device coupled to the navigation controller 36. The ultrasound imaging device images any of the aforementioned objects, e.g., the manipulator 14, the tool 20, and/or the patient 12, and generates state signals to the navigation controller 36 based on the ultrasound images. The ultrasound images may be 2-D, 3-D, or a combination of both. The navigation controller 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation controller 36. The manipulator 14, the tool 20, and/or the patient 12 may comprise RF emitters or transponders attached thereto. The RF emitters or transponders may be passive or actively energized. The RF transceiver transmits an RF tracking signal and generates state signals to the navigation controller 36 based on RF signals received from the RF emitters. The navigation controller 36 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52A, 52B, 54, 56, PT shown in FIG. 1.

In yet another example, the navigation system 32 and/or localizer 44 are electromagnetically based. For example, the navigation system 32 may comprise an EM transceiver coupled to the navigation controller 36. The manipulator 14, the tool 20, and/or the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the navigation controller 36 based upon EM signals received from the trackers. The navigation controller 36 may analyze the received EM signals to associate relative states thereto. Again, such navigation system 32 examples may have structural configurations that are different than the navigation system 32 configuration shown in FIG. 1.

The navigation system 32 may have any other suitable components or structure not specifically recited herein. Furthermore, any of the techniques, methods, and/or components described above with respect to the navigation system 32 shown may be implemented or provided for any of the other examples of the navigation system 32 described herein. For example, the navigation system 32 may utilize solely inertial tracking or any combination of tracking techniques, and may additionally or alternatively comprise, fiber optic-based tracking, machine-vision tracking, and the like.

Figure 2:
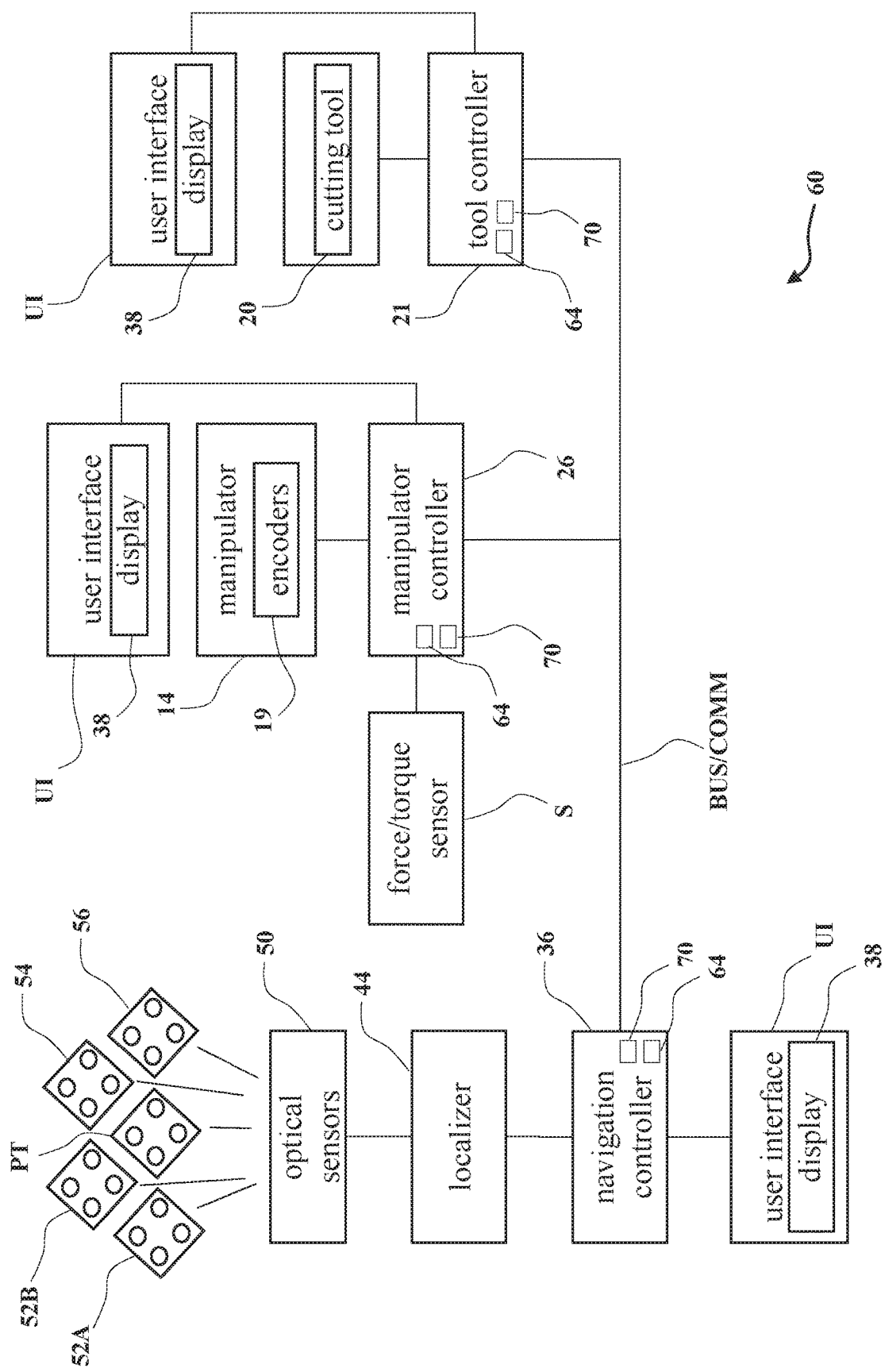
FIG. 2 is a block diagram of a control system for controlling the robotic surgical system.

Referring to FIG. 2, the system 10 includes a control system 60 that comprises, among other components, the manipulator controller 26, the navigation controller 36, and the tool controller 21. The control system 60 further includes one or more software programs and software modules shown in FIG. 3. The software modules may be part of the program or programs that operate on the manipulator controller 26, navigation controller 36, tool controller 21, or any combination thereof, to process data to assist with control of the system 10. The software programs and/or modules include computer readable instructions stored in non-transitory memory 64 on the manipulator controller 26, navigation controller 36, tool controller 21, or a combination thereof, to be executed by one or more processors 70 of the controllers 21, 26, 36. The memory 64 may be any suitable configuration of memory, such as RAM, non-volatile memory, etc., and may be implemented locally or from a remote database. Additionally, software modules for prompting and/or communicating with the user may form part of the program or programs and may include instructions stored in memory 64 on the manipulator controller 26, navigation controller 36, tool controller 21, or any combination thereof. The user may interact with any of the input devices of the navigation user interface UI or other user interface UI to communicate with the software modules. The user interface software may run on a separate device from the manipulator controller 26, navigation controller 36, and/or tool controller 21.

The control system 60 may comprise any suitable configuration of input, output, and processing devices suitable for carrying out the functions and methods described herein. The control system 60 may comprise the manipulator controller 26, the navigation controller 36, or the tool controller 21, or any combination thereof, or may comprise only one of these controllers. These controllers may communicate via a wired bus or communication network as shown in FIG. 2, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

Figure 3:
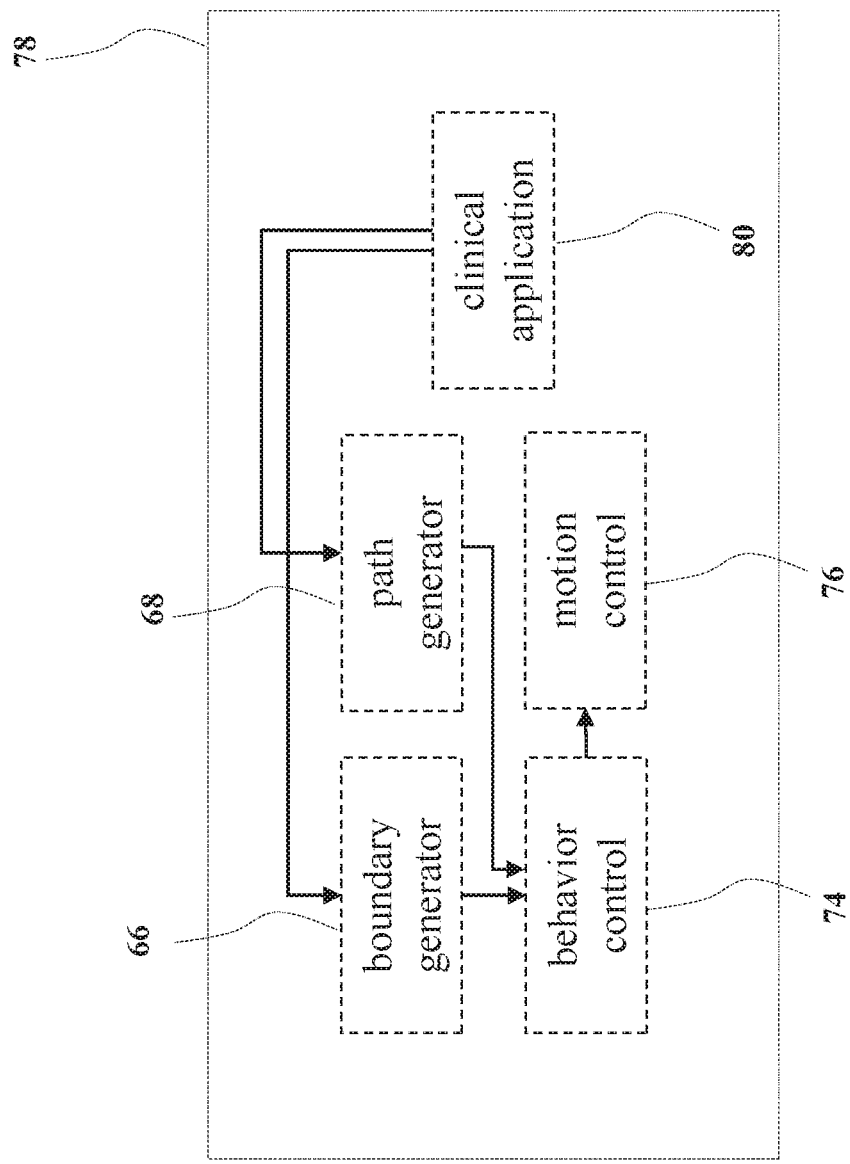
FIG. 3 is a functional block diagram of a software program.

Referring to FIG. 3, the software employed by the control system 60 includes a boundary generator 66. As shown in FIG. 4, the boundary generator 66 is a software program or module that generates a virtual boundary 71 for constraining movement and/or operation of the tool 20. The virtual boundary 71 may be one-dimensional, two-dimensional, three-dimensional, and may comprise a point, line, axis, trajectory, plane, or other shapes, including complex geometric shapes. In some embodiments, the virtual boundary 71 is a surface defined by a triangle mesh. Such virtual boundaries 71 may also be referred to as virtual objects. The virtual boundaries 71 may be defined with respect to an anatomical model AM, such as a 3-D bone model. In the example of FIG. 4, the virtual boundaries 71 are planar boundaries to delineate five planes for a total knee implant, and are associated with a 3-D model of the head of the femur F. The anatomical model AM is registered to the one or more patient trackers 54, 56 such that the virtual boundaries 71 become associated with the anatomical model AM. The virtual boundaries 71 may be implant-specific, e.g., defined based on a size, shape, volume, etc. of an implant and/or patient-specific, e.g., defined based on the patient's anatomy. The virtual boundaries 71 may be boundaries that are created pre-operatively, intra-operatively, or combinations thereof. In other words, the virtual boundaries 71 may be defined before the surgical procedure begins, during the surgical procedure (including during tissue removal), or combinations thereof. In any case, the control system 60 obtains the virtual boundaries 71 by storing/retrieving the virtual boundaries 71 in/from memory, obtaining the virtual boundaries 71 from memory, creating the virtual boundaries 71 pre-operatively, creating the virtual boundaries 71 intra-operatively, or the like.

The manipulator controller 26 and/or the navigation controller 36 track the state of the tool 20 relative to the virtual boundaries 71. In one example, the state of the TCP is measured relative to the virtual boundaries 71 for purposes of determining haptic forces to be applied to a virtual rigid body model via a virtual simulation so that the tool 20 remains in a desired positional relationship to the virtual boundaries 71 (e.g., not moved beyond them). The results of the virtual simulation are commanded to the manipulator 14. The control system 60 controls/positions the manipulator 14 in a manner that emulates the way a physical handpiece would respond in the presence of physical boundaries/barriers. The boundary generator 66 may be implemented on the manipulator controller 26. Alternatively, the boundary generator 66 may be implemented on other components, such as the navigation controller 36.

Referring to FIGS. 3 and 5, a path generator 68 is another software program or module run by the control system 60. In one example, the path generator 68 is run by the manipulator controller 26. The path generator 68 generates a tool path TP for the tool 20 to traverse, such as for removing sections of the anatomy to receive an implant. The tool path TP may comprise a plurality of path segments PS, or may comprise a single path segment PS. The path segments PS may be straight segments, curved segments, combinations thereof, or the like. The tool path TP may also be defined with respect to the anatomical model AM. The tool path TP may be implant-specific, e.g., defined based on a size, shape, volume, etc. of an implant and/or patient-specific, e.g., defined based on the patient's anatomy.

In one version described herein, the tool path TP is defined as a tissue removal path, but, in other versions, the tool path TP may be used for treatment other than tissue removal. One example of the tissue removal path described herein comprises a milling path 72. It should be understood that the term "milling path" generally refers to the path of the tool 20 in the vicinity of the target site for milling the anatomy and is not intended to require that the tool 20 be operably milling the anatomy throughout the entire duration of the path. For instance, as will be understood in further detail below, the milling path 72 may comprise sections or segments where the tool 20 transitions from one location to another without milling. Additionally, other forms of tissue removal along the milling path 72 may be employed, such as tissue ablation, and the like. The milling path 72 may be a predefined path that is created pre-operatively, intra-operatively, or combinations thereof. In other words, the milling path 72 may be defined before the surgical procedure begins, during the surgical procedure (including during tissue removal), or combinations thereof. In any case, the control system 60 obtains the milling path 72 by storing/retrieving the milling path 72 in/from memory, obtaining the milling path 72 from memory, creating the milling path 72 pre-operatively, creating the milling path 72 intra-operatively, or the like. The milling path 72 may have any suitable shape, or combinations of shapes, such as circular, helical/corkscrew, linear, curvilinear, combinations thereof, and the like.

One example of a system and method for generating the virtual boundaries 71 and/or the milling path 72 is described in U.S. Pat. No. 9,119,655, entitled, "Surgical Manipulator Capable of Controlling a Surgical Instrument in Multiple Modes," the disclosure of which is hereby incorporated by reference. In some examples, the virtual boundaries 71 and/or milling paths 72 may be generated offline rather than on the manipulator controller 26 or navigation controller 36. Thereafter, the virtual boundaries 71 and/or milling paths 72 may be utilized at runtime by the manipulator controller 26.

Referring back to FIG. 3, two additional software programs or modules run on the manipulator controller 26 and/or the navigation controller 36. One software module performs behavior control 74. Behavior control 74 is the process of computing data that indicates the next commanded position and/or orientation (e.g., pose) for the tool 20. In some cases, only the position of the TCP is output from the behavior control 74, while in other cases, the position and orientation of the tool 20 is output. Output from the boundary generator 66, the path generator 68, and a force/torque sensor S may feed as inputs into the behavior control 74 to determine the next commanded position and/or orientation for the tool 20. The behavior control 74 may process these inputs, along with one or more virtual constraints described further below, to determine the commanded pose.

The second software module performs motion control 76. One aspect of motion control is the control of the manipulator 14. The motion control 76 receives data defining the next commanded pose from the behavior control 74. Based on these data, the motion control 76 determines the next position of the joint angles of the joints J of the manipulator 14 (e.g., via inverse kinematics and Jacobian calculators) so that the manipulator 14 is able to position the tool 20 as commanded by the behavior control 74, e.g., at the commanded pose. In other words, the motion control 76 processes the commanded pose, which may be defined in Cartesian space, into joint angles of the manipulator 14, so that the manipulator controller 26 can command the joint motors accordingly, to move the joints J of the manipulator 14 to commanded joint angles corresponding to the commanded pose of the tool 20. In one version, the motion control 76 regulates the joint angle of each joint J and continually adjusts the torque that each joint motor outputs to, as closely as possible, ensure that the joint motor drives the associated joint J to the commanded joint angle.

The boundary generator 66, path generator 68, behavior control 74, and motion control 76 may be sub-sets of a software program 78. Alternatively, each may be software programs that operate separately and/or independently in any combination thereof. The term "software program" is used herein to describe the computer-executable instructions that are configured to carry out the various capabilities of the technical solutions described. For simplicity, the term "software program" is intended to encompass, at least, any one or more of the boundary generator 66, path generator 68, behavior control 74, and/or motion control 76. The software program 78 can be implemented on the manipulator controller 26, navigation controller 36, or any combination thereof, or may be implemented in any suitable manner by the control system 60.

A clinical application 80 may be provided to handle user interaction. The clinical application 80 handles many aspects of user interaction and coordinates the surgical workflow, including pre-operative planning, implant placement, registration, bone preparation visualization, and post-operative evaluation of implant fit, etc. The clinical application 80 is configured to output to the displays 38. The clinical application 80 may run on its own separate processor or may run alongside the navigation controller 36. In one example, the clinical application 80 interfaces with the boundary generator 66 and/or path generator 68 after implant placement is set by the user, and then sends the virtual boundary 71 and/or tool path TP returned by the boundary generator 66 and/or path generator 68 to the manipulator controller 26 for execution. Manipulator controller 26 executes the tool path TP as described herein. The manipulator controller 26 may additionally create certain segments (e.g., lead-in segments) when starting or resuming machining to smoothly get back to the generated tool path TP. The manipulator controller 26 may also process the virtual boundaries 71 to generate virtual corresponding virtual constraints as described further below.

The system 10 may operate in a manual mode, such as described in U.S. Pat. No. 9,119,655, incorporated herein by reference. Here, the user manually directs, and the manipulator 14 executes movement of the tool 20 and its energy applicator 24 at the surgical site. The user physically contacts the tool 20 to cause movement of the tool 20 in the manual mode. In one version, the manipulator 14 monitors forces and torques placed on the tool 20 by the user in order to position the tool 20. For example, the manipulator 14 may comprise the force/torque sensor S that detects the forces and torques applied by the user and generates corresponding input used by the control system 60 (e.g., one or more corresponding input/output signals).

The force/torque sensor S may comprise a 6-DOF force/torque transducer. The manipulator controller 26 and/or the navigation controller 36 receives the input (e.g., signals) from the force/torque sensor S. In response to the user-applied forces and torques, the manipulator 14 moves the tool 20 in a manner that emulates the movement that would have occurred based on the forces and torques applied by the user. Movement of the tool 20 in the manual mode may also be constrained in relation to the virtual boundaries 71 generated by the boundary generator 66. In some versions, measurements taken by the force/torque sensor S are transformed from a force/torque coordinate system FT of the force/torque sensor S to another coordinate system, such as a virtual mass coordinate system VM in which a virtual simulation is carried out on the virtual rigid body model of the tool 20 so that the forces and torques can be virtually applied to the virtual rigid body in the virtual simulation to ultimately determine how those forces and torques (among other inputs) would affect movement of the virtual rigid body, as described below.

The system 10 may also operate in a semi-autonomous mode in which the manipulator 14 moves the tool 20 along the milling path 72 (e.g., the active joints J of the manipulator 14 operate to move the tool 20 without requiring force/torque on the tool 20 from the user). An example of operation in the semi-autonomous mode is also described in U.S. Pat. No. 9,119,655, incorporated herein by reference. In some embodiments, when the manipulator 14 operates in the semi-autonomous mode, the manipulator 14 is capable of moving the tool 20 free of user assistance. Free of user assistance may mean that a user does not physically contact the tool 20 to move the tool 20. Instead, the user may use some form of remote control to control starting and stopping of movement. For example, the user may hold down a button of the remote control to start movement of the tool 20 and release the button to stop movement of the tool 20.

Figure 6A:
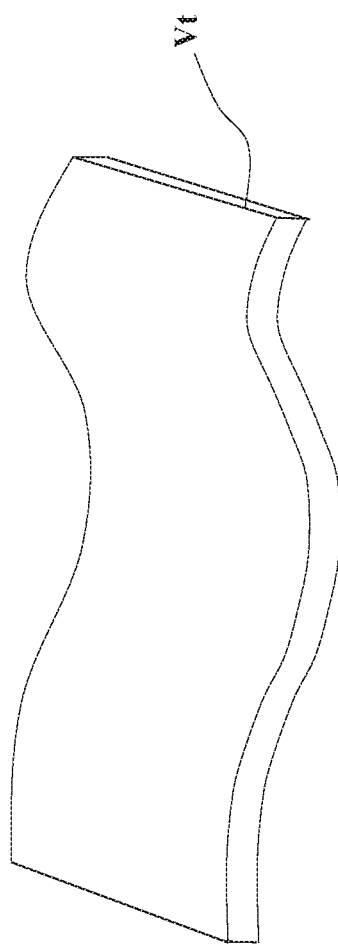
FIGS. 6A-6C illustrate a sequence of steps carried out in a manual mode of operation of the robotic surgical system.
Figure 6B:
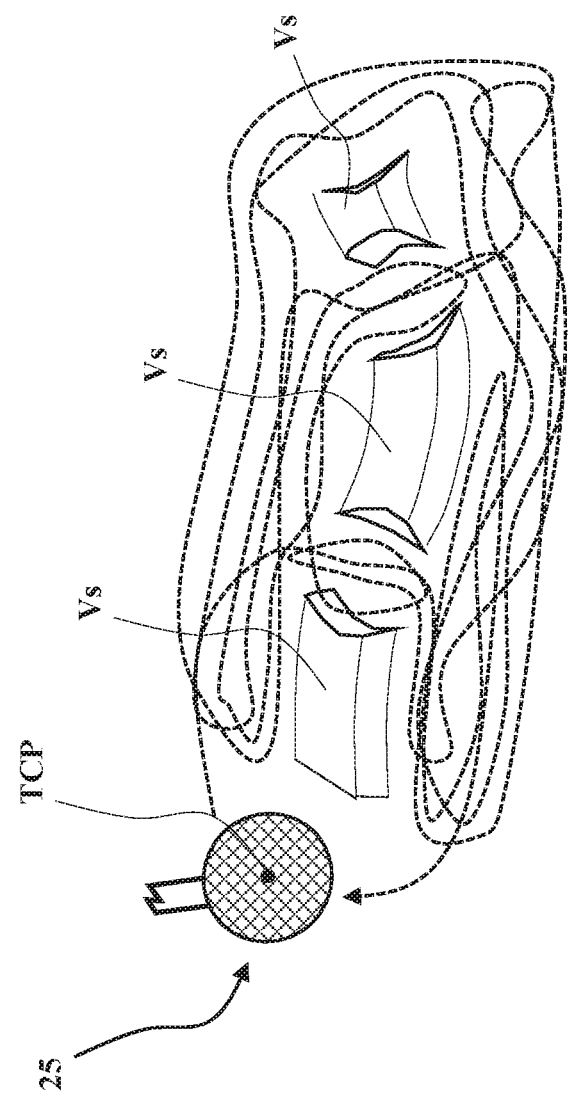
Figure 6C:
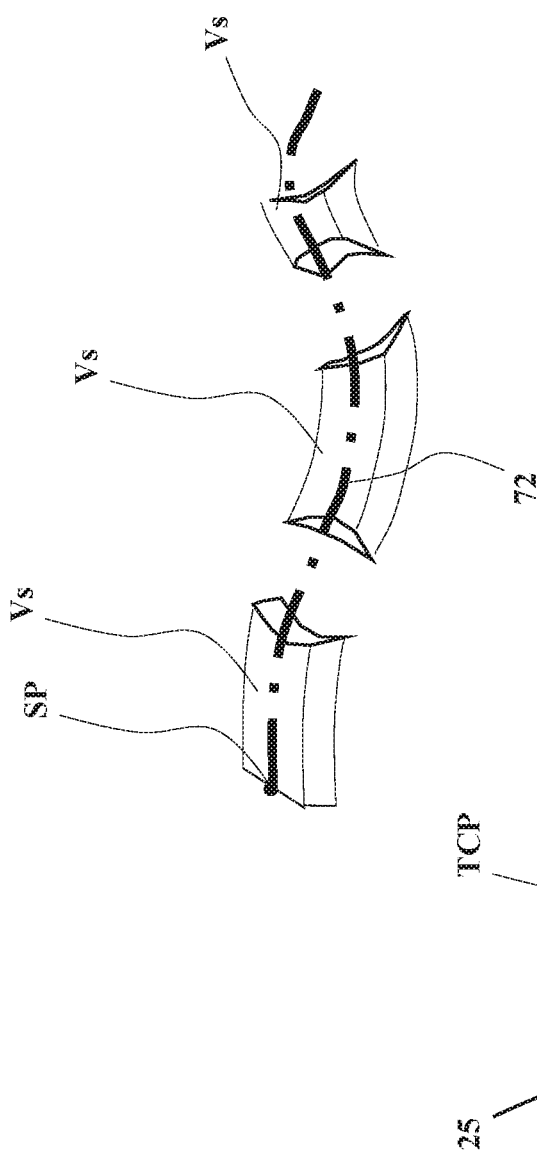

In the manual mode, it may be fatiguing to the user to remove an entire volume of tissue Vt required to be removed for a particular surgical procedure, especially when the volume of tissue Vt is relatively large as compared to the working end of the tool 20. As shown in FIGS. 6A through 6C, for example, it may be difficult for the user, through manual mode operation of the manipulator 14, to place the TCP of the tool 20 to remove all of the bone required. Instead, as illustrated in FIG. 6B, the user's operation in the manual mode (see tortuous movement arrow) causes the bur 25 to skip several subvolumes Vs of bone that need removal leaving these bone subvolumes Vs for later removal, as shown in FIG. 6C. To this end, the system 10 may switch from the manual mode to the semi-autonomous mode to complete the removal of the bone, such as in the manner described in U.S. Pat. No. 9,119,655, incorporated herein by reference, including generating a milling path 72 through these subvolumes Vs. Accordingly, to finish bone removal in preparation for receiving the implant, the manipulator 14 autonomously moves the TCP along the milling path 72.

The system 10 may also operate in a guided-manual mode to remove the remaining subvolumes Vs of bone, or for other purposes. In this mode, aspects of control used in both the manual mode and the semi-autonomous mode are utilized. For example, forces and torques applied by the user are detected by the force/torque sensor S to determine an external force $F_{ext}$. The external force $F_{ext}$ may comprise other forces and torques, aside from those applied by the user, such as gravity-compensating forces, backdrive forces, and the like, as described in U.S. Pat. No. 9,119,655, incorporated herein by reference. Thus, the user-applied forces and torques at least partially define the external force $F_{ext}$, and in some cases, may fully define the external force $F_{ext}$. Additionally, in the guided-manual mode, the system 10 utilizes the milling path 72 (or other tool path) generated by the path generator 68 to help guide movement of the tool 20 along the milling path 72. In some cases, the milling path 72 is generated upon the user entering the guided-manual mode. The guided-manual mode relies on manual manipulation of the tool 20 to advance the tool 20, but such advancement, instead of merely emulating the movement that would have occurred based on the forces and torques applied by the user, is actively controlled to be along the milling path 72. Therefore, the guided-manual mode combines direct user engagement with the tool 20 and the benefits associated with moving the tool 20 along the milling path 72, as illustrated in FIG. 7.

Figure 7:
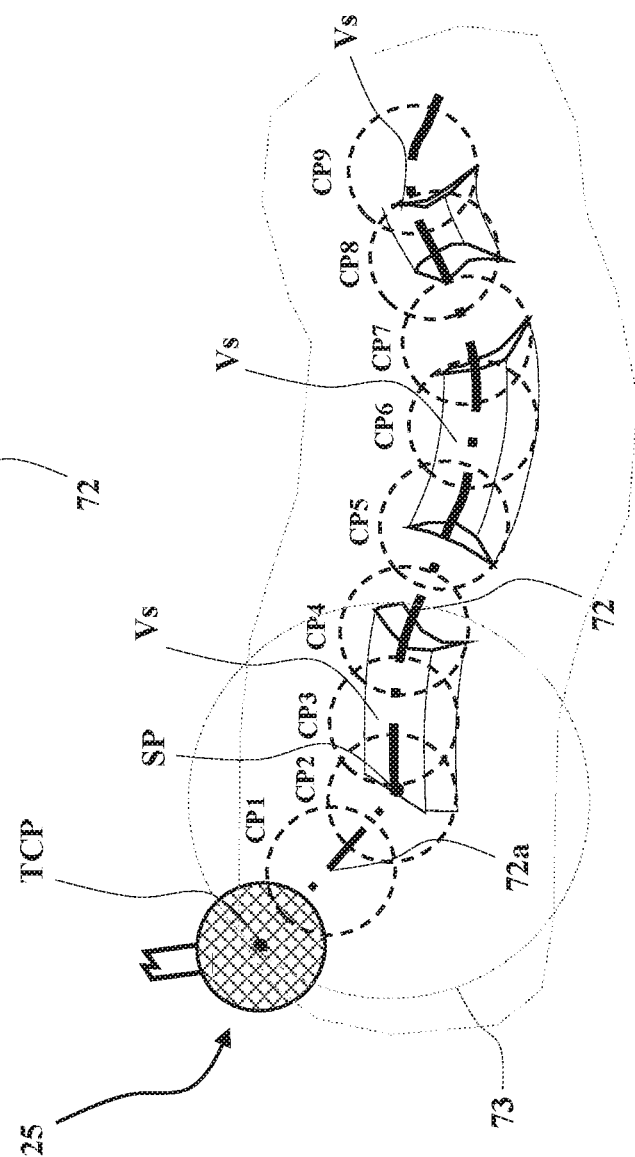
FIG. 7 illustrates a series of movements of the surgical tool along a milling path.

In some cases, as shown in FIG. 7, a lead-in path 72a may first be generated by the behavior control 74 when initiating operation in the guided-manual mode. The lead-in path 72 is a direct pathway from the current position/pose of the tool 20 to the milling path 72 (e.g., connects the TCP to a starting point SP of the milling path 72). The lead-in path 72 may be generated based on a shortest distance from the current position/pose of the tool 20 to the milling path 72 (e.g., shortest distance from the TCP to any point on the milling path 72) or may be generated from the current position/pose of the tool 20 to the starting point SP of the milling path 72. In any case, the lead-in path 72a is generated to lead the tool 20 to the milling path 72. Creation of the lead-in path 72a may require the TCP of the tool 20, and/or any other part of the tool 20, to be within a predefined distance of the starting point SP. Visualization on the display 38 may guide the user into moving the tool 20 to be within this predefined distance. Such a distance could be defined by a virtual sphere 73 centered on the starting point SP, or the like, as shown in FIG. 7. Once within the predefined distance, the behavior control 74 creates the lead-in path 72a to guide the tool 20 to the remainder of the milling path 72. This lead-in path 72a and switching to the guided-manual mode could be automatic upon the TCP of the tool 20 entering the sphere 73.

Figure 8:
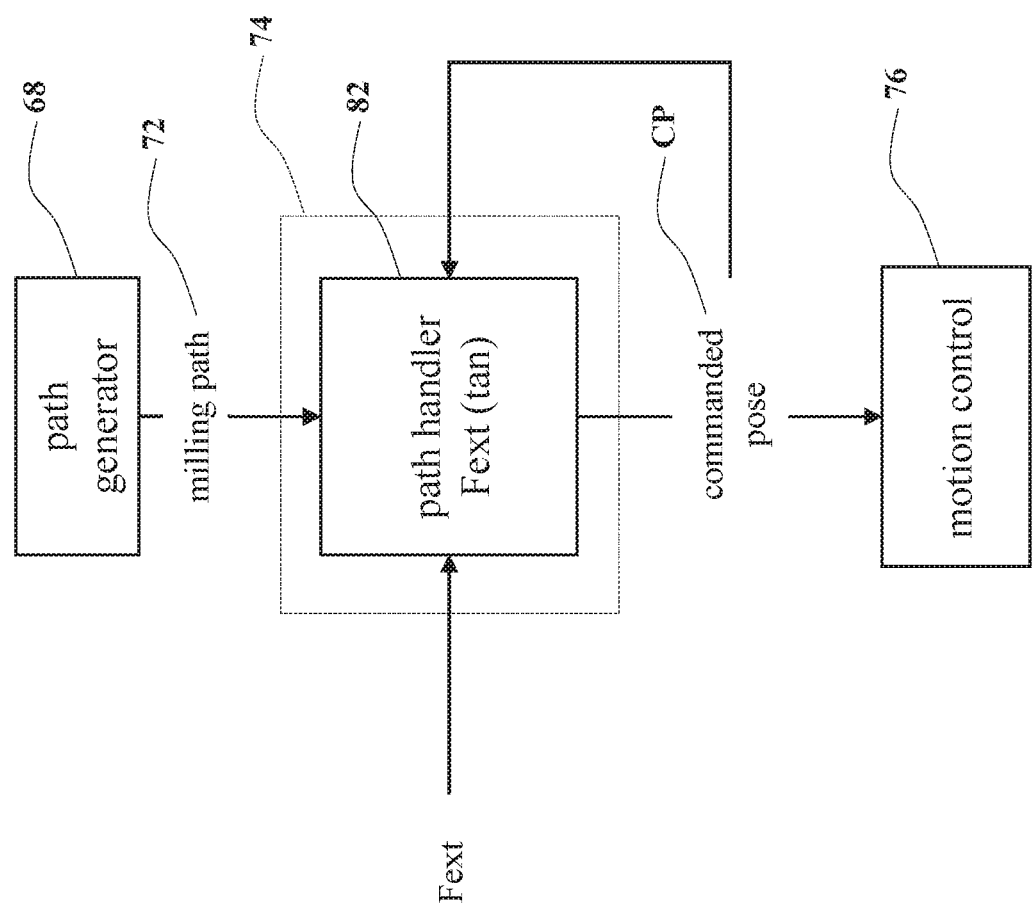
FIG. 8 is a block diagram of modules operable by the control system.

FIG. 8 shows processes carried out to execute the guided-manual mode, in one example. In this example, the behavior control 74 comprises a path handler 82. The path handler 82 comprises executable software stored in a non-transitory memory of any one or more of the aforementioned controllers and implemented by the control system 60. As shown, one input into the path handler 82 comprises the milling path 72 generated by the path generator 68. The milling path 72 may be three-dimensional, as previously described, and defined with respect to any desired coordinate system, such as the manipulator coordinate system MNPL, localizer coordinate system LCLZ, or other coordinate system.

Another input into the path handler 82, in the example shown in FIG. 8, is the current external force $F_{ext}$, including the forces/torques sensed by the force/torque sensor S. The external force $F_{ext}$ may comprise three components of force along x, y, z axes, or may comprise six components of force including the three components of force along x, y, z axes and three components of torque about the x, y, z axes. The components of force may be initially defined in a sensor coordinate system, but can be transformed to another coordinate system, such as a coordinate system of the tool 20.

Another input into the path handler 82 comprises the last (most recent or current) commanded pose CP. As previously mentioned, the commanded pose CP may comprise Cartesian coordinates of the TCP of the tool 20 and a commanded orientation of the tool 20, e.g., pose.

The path handler 82 interpolates along the milling path 72 to determine the next commanded pose CP based on the external force $F_{ext}$ (as transformed to the TCP) and the previous commanded pose. At each iteration of the process shown in FIG. 8, which may be carried out at any suitable frame rate (e.g., every 125 microseconds), the path handler 82 calculates a tangential component $F_{ext}$ (tan) of the external force $F_{ext}$, which is tangential to the milling path 72 at the previous commanded pose. This tangential component of force $F_{ext}$ (tan) at least partially dictates how far along the milling path 72 the tool 20 should move. Said differently, since this tangential component of force $F_{ext}$ (tan) is at least partially derived by how much force the user applied in the tangential direction (e.g., to move the tool 20 in the tangential direction), it largely (and completely, in some cases) defines how far the path handler 82 will ultimately decide to move the tool 20 along the milling path 72. $F_{ext}$ (tan) is computed using both the force and torque components measured by the force/torque sensor S in the sensor coordinate system, which are then transformed to the TCP (tangential path direction) using a Jacobian.

In some cases, the user may exert a force on the tool 20 indicating a desire to move off the milling path 72 and end operation in the guided-manual mode, such as by applying a force normal to the milling path 72 and/or opposite to a previous force applied to move the tool 20 along the milling path 72. For example, the sign +/− of the tangential component of the external force $F_{ext}$ (tan) and/or the magnitude of the normal component of $F_{ext}$ may be evaluated by the control system 60. Based on the sign +/− of the tangential component of $F_{ext}$, and/or the magnitude of the normal component of $F_{ext}$ exceeding a predetermined threshold, the control system 60 can determine whether to switch back to the manual mode or to provide some other type of control for the user, i.e., in the event the user's application of force clearly indicates a desire to end the guided-manual mode. In some versions, the sign +/− of the tangential component of the external force $F_{ext}$ (tan) is utilized to determine a direction that the user wishes to move along the milling path 72 (e.g., forward/backward), and not necessarily a desire to exit the guided-manual mode.

Figure 9A:
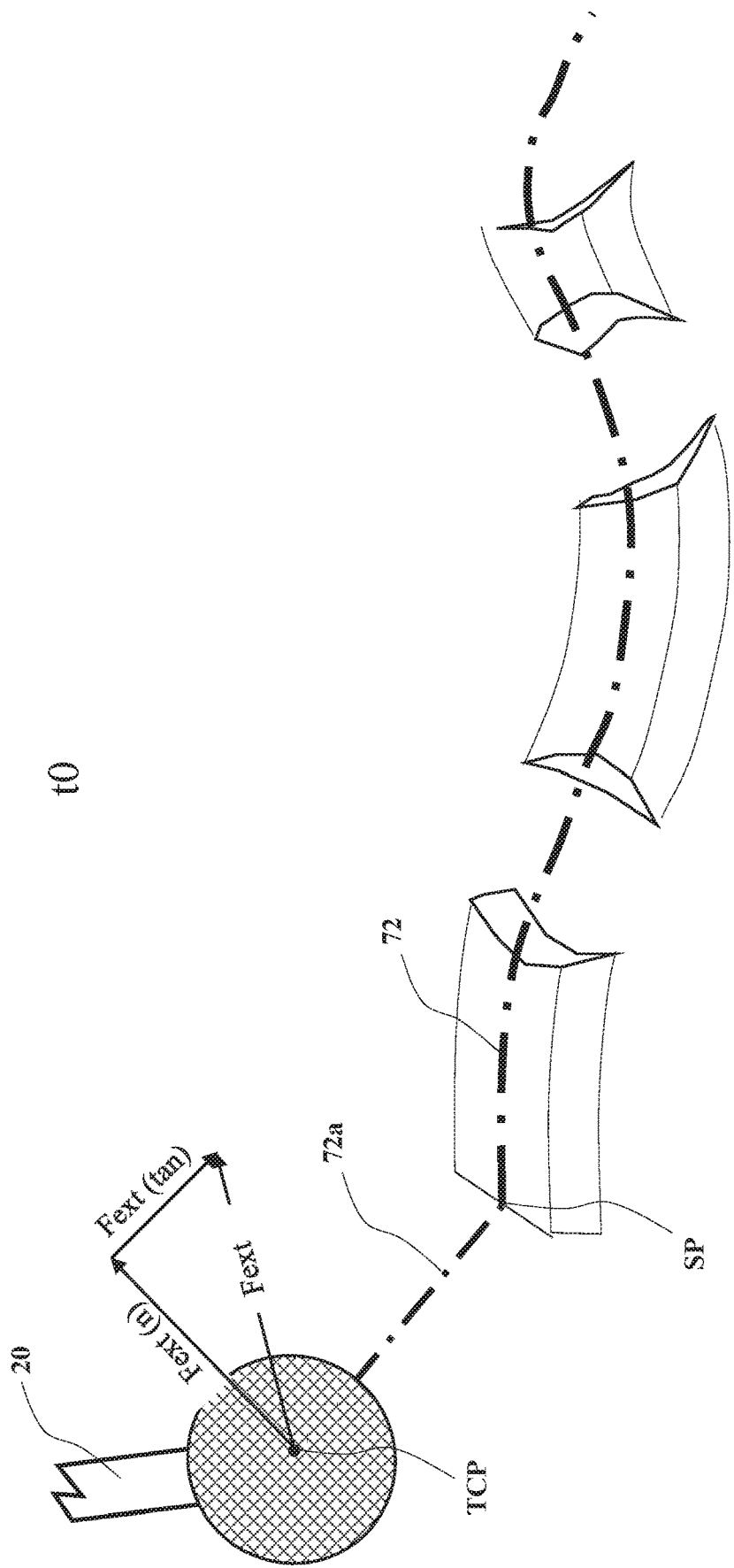
Figure 9B:
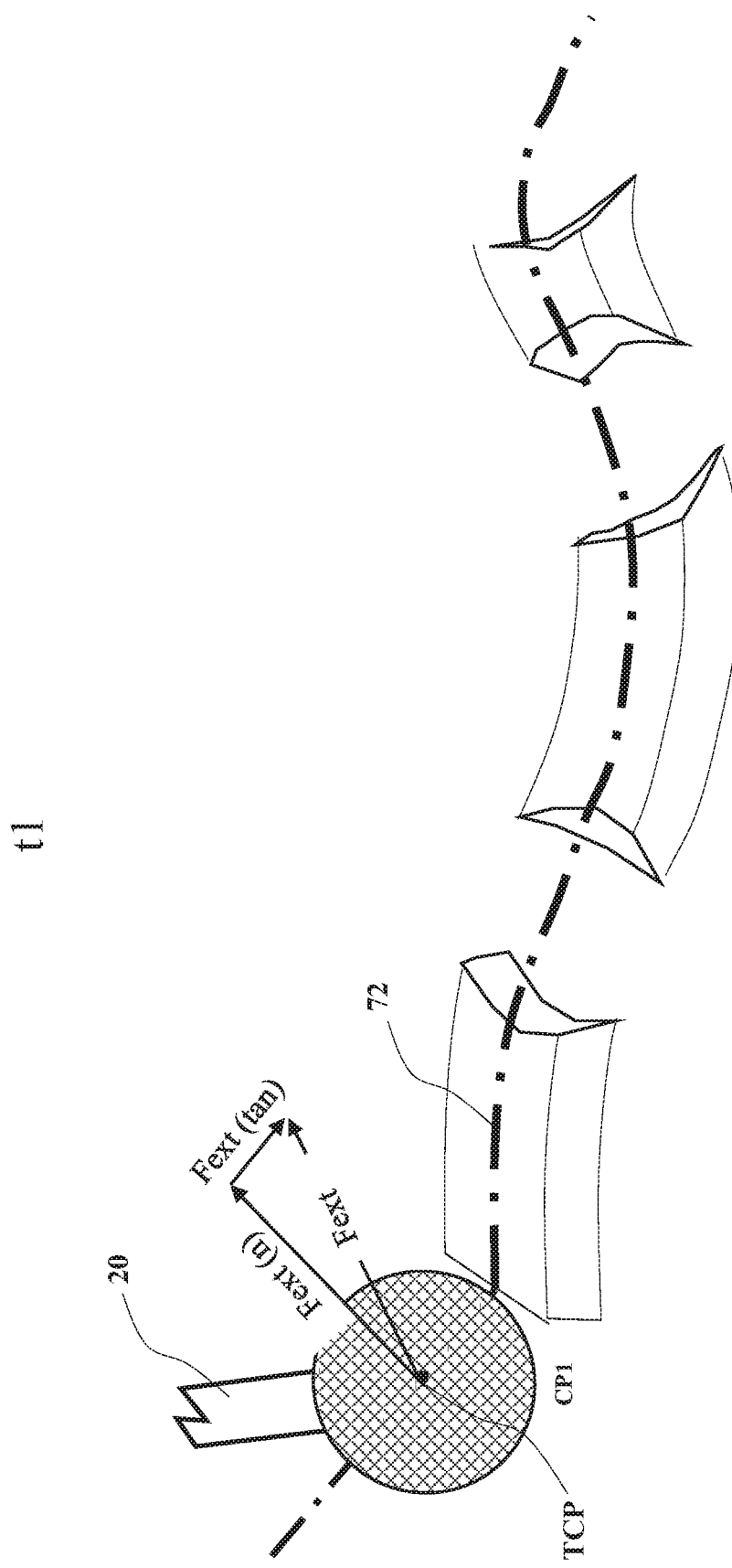
Figure 9C:
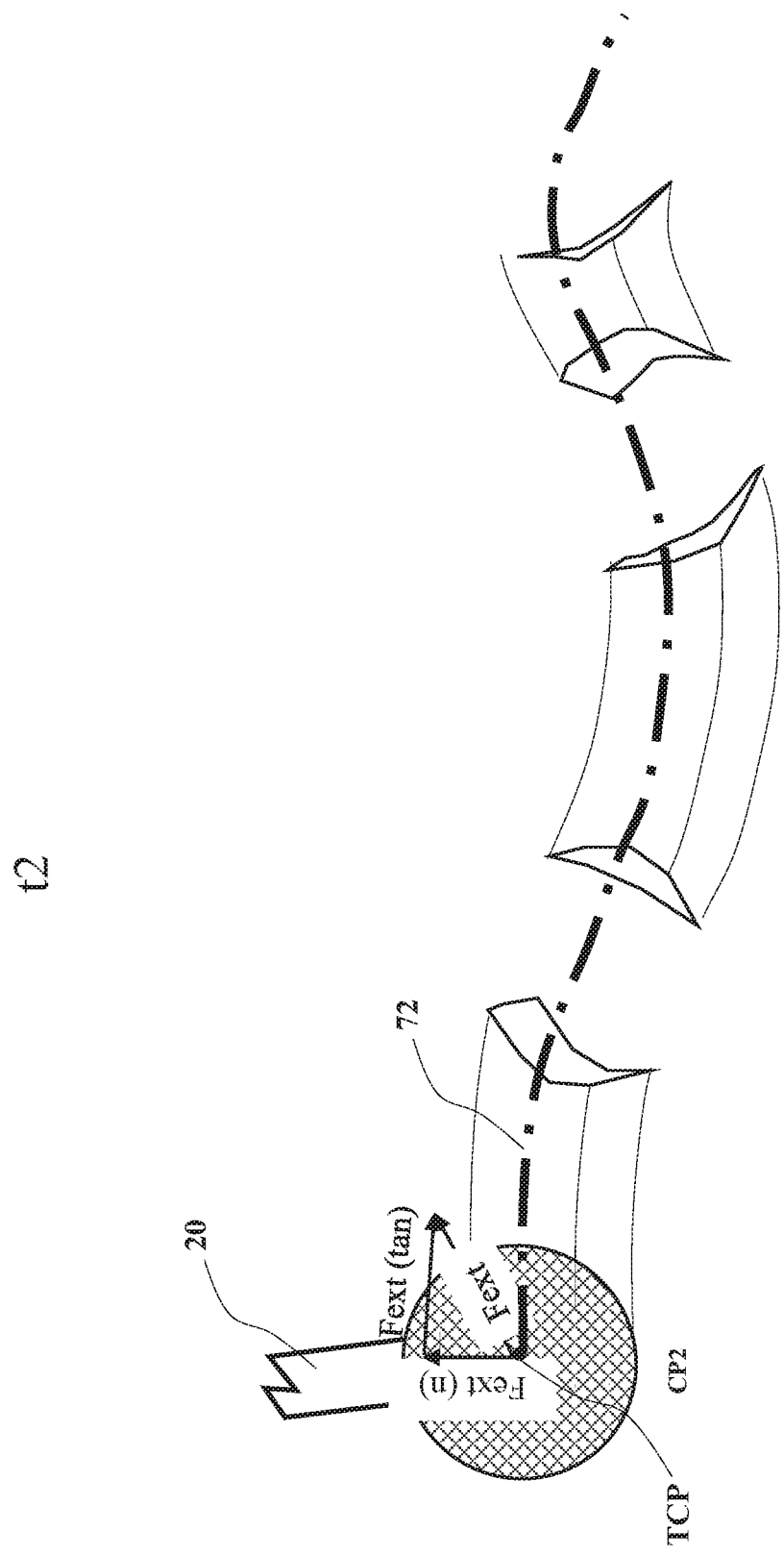
Figure 9D:
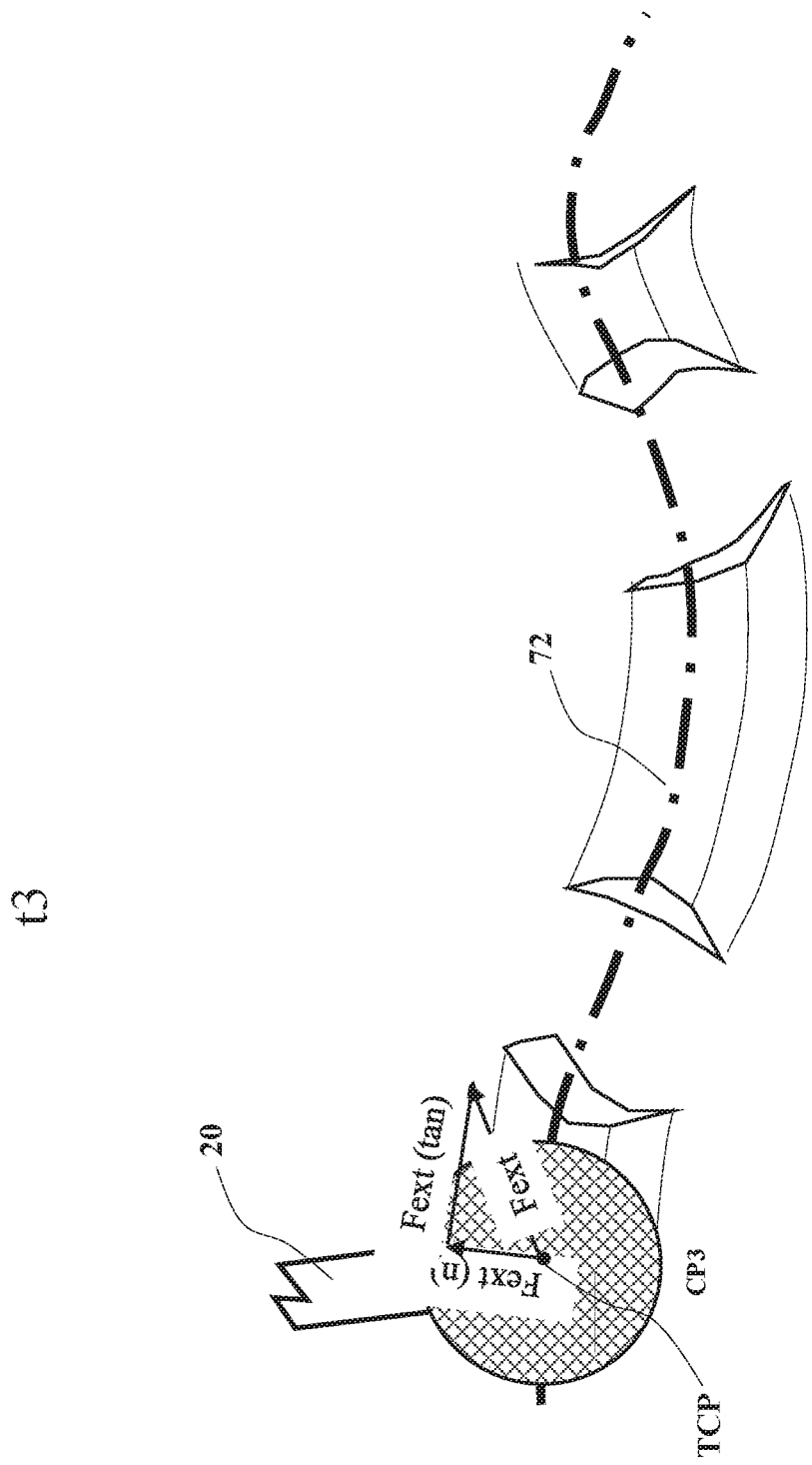
Figure 9E:
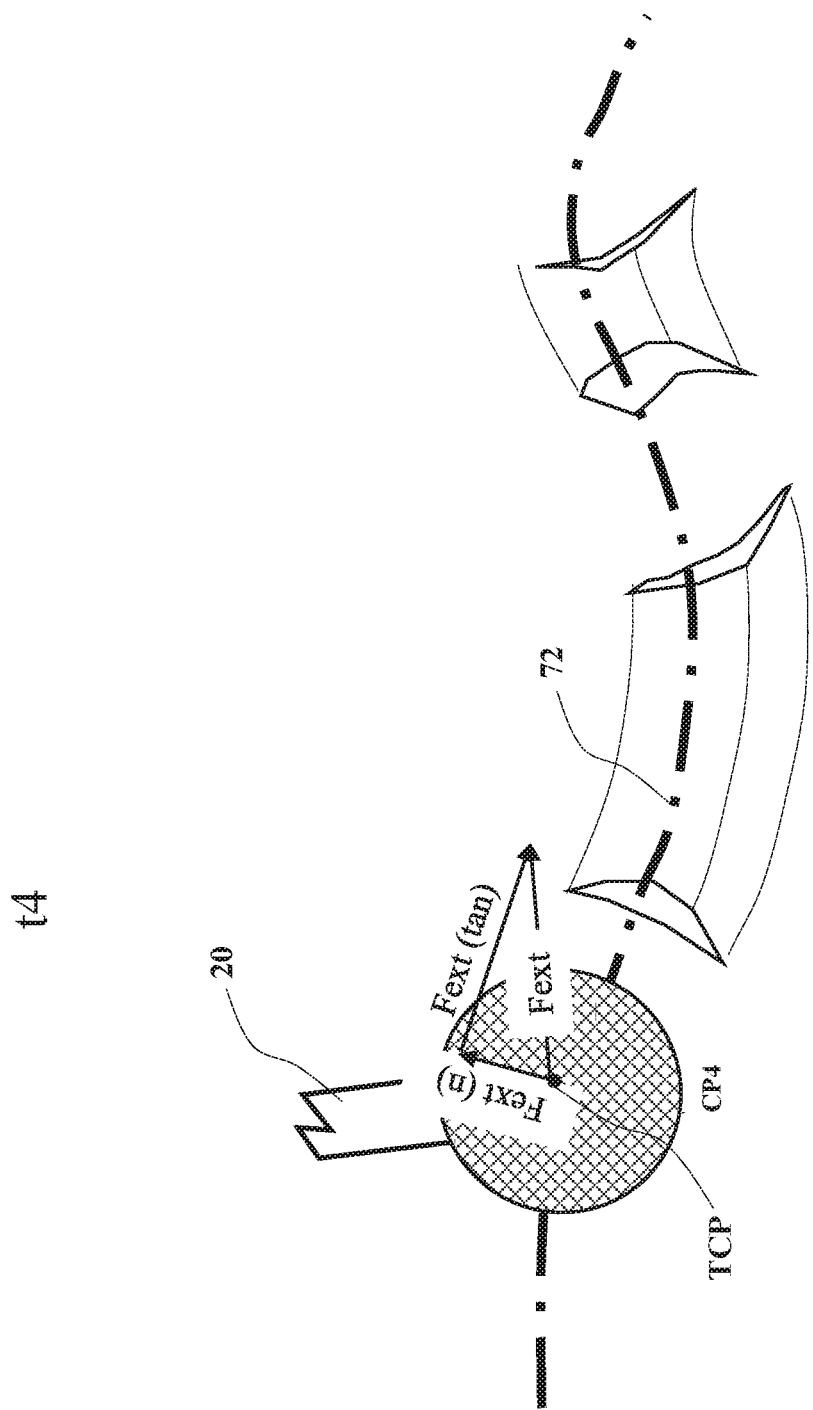
Figure 9G:
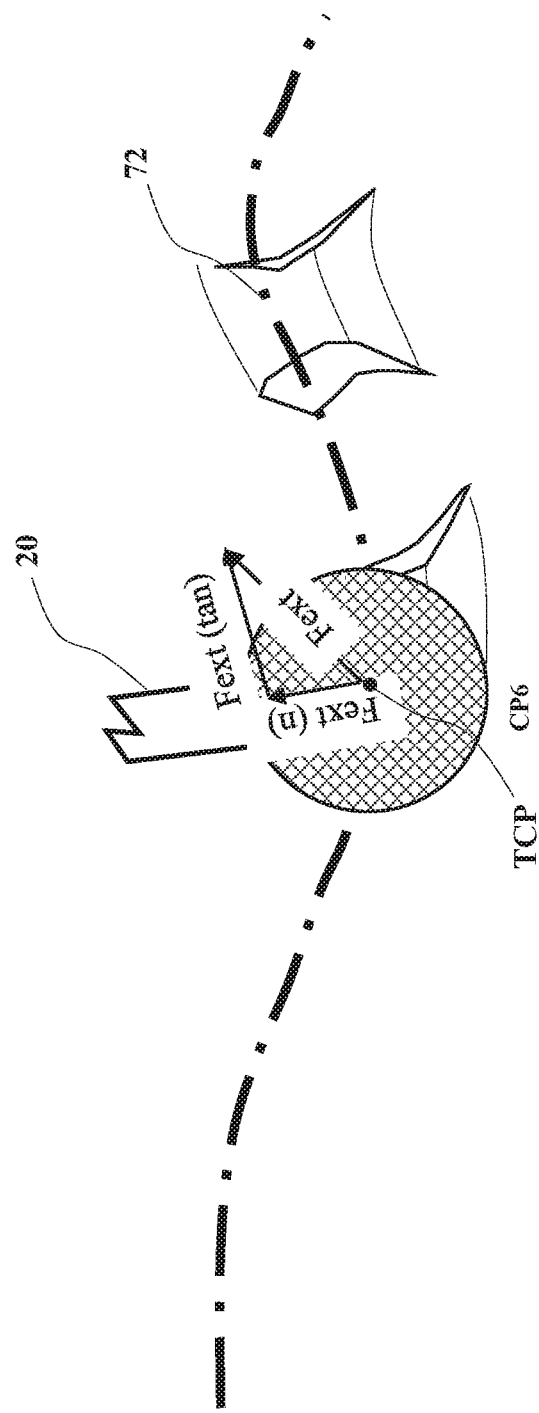
Figure 9H:
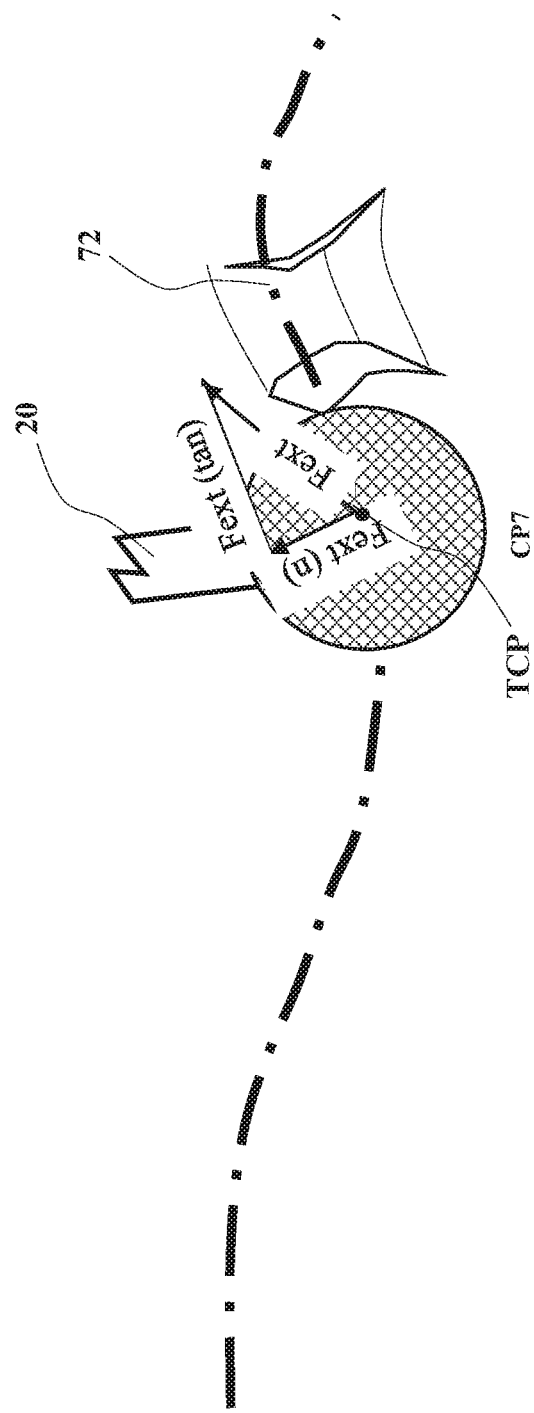
Figure 9I:
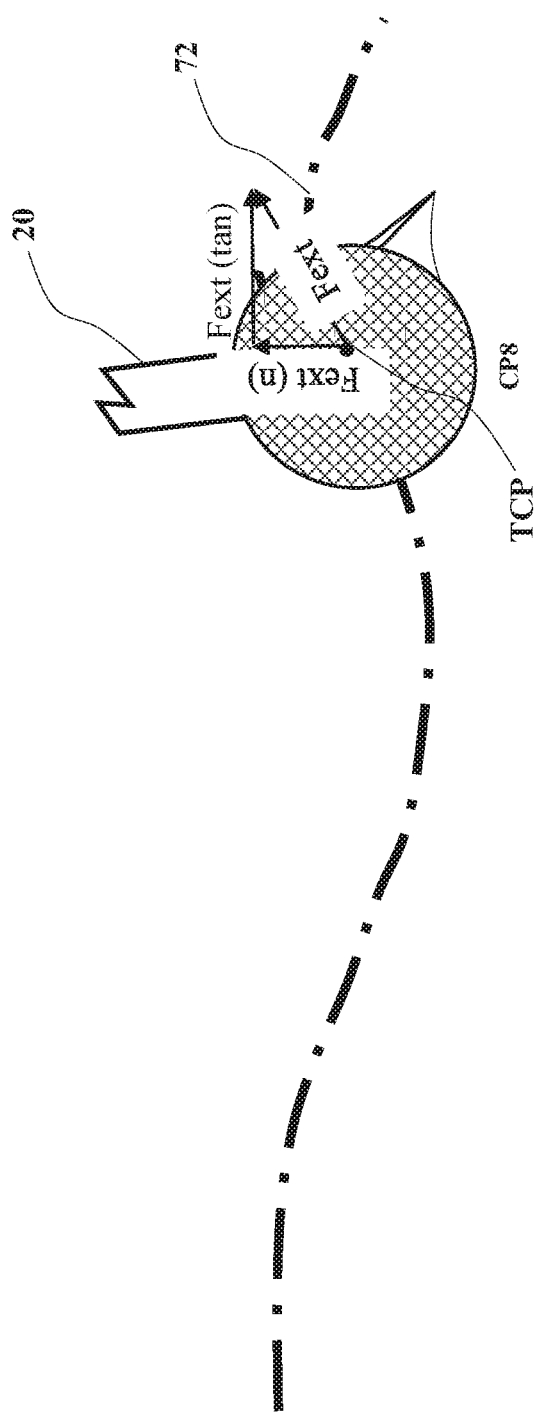

Once the tangential component $F_{ext}$ (tan) of the external force $F_{ext}$ is determined and has a sign +/− indicating a desire to continue moving along the milling path 72 and/or the magnitude of the normal component indicates a desire to continue moving along the milling path 72, the path handler 82 generates the next commanded pose CP. Referring to FIGS. 8 and 9A, the next commanded pose can be determined, in one example, by the following steps: (1) selecting a virtual mass (Vm) for the tool 20, which may be close to the actual mass of the tool 20, or may be any appropriate value to provide desired behavior; (2) calculating a virtual acceleration (a) for the TCP of the tool 20 in the tangential direction based on the tangential component of force $F_{ext}$ (tan) applied at the TCP and the virtual mass ($F_{ext}$ (tan)= (Vm)*(a)); (3) integrating the acceleration over one time step (e.g., 125 microseconds) to determine velocity; (4) integrating the velocity over the same time step to determine a change in position and corresponding translation distance in the tangential direction; and (5) applying the translation distance from the previous commanded pose, along the milling path 72, to yield the next commanded pose CP, e.g., the next commanded pose CP is located on the milling path 72 spaced from the previous commanded pose by the translation distance. The computed translation distance may thus be used as an approximation of how far to move the TCP of the tool 20 along the milling path 72.

The scalar virtual mass Vm could be chosen to give a desired feel, i.e., how the TCP of the tool 20 should accelerate along the milling path 72 in response to the user's tangential forces. Alternately, the scalar virtual mass Vm could be computed from a 6-DOF virtual mass matrix M, which contains the mass and inertia matrix for the virtual rigid body, by computing the scalar effective mass each time step that is seen along the tangential direction of the milling path 72.

The commanded pose CP may also comprise an orientation component that may be defined separately from determining how far to move the TCP of the tool 20 along the milling path 72. For example, the orientation component may be based on maintaining a constant orientation while the TCP moves along the milling path 72. The orientation component may be a predefined orientation or defined based on a particular location along the milling path 72 being traversed. The orientation component may also be user-defined and/or defined in other ways. Thus, the commanded pose CP may include the position output computed by the path handler 82 combined with the separately-computed orientation. The position output and the orientation are combined and output as the commanded pose CP to the motion control 76.

Figure 18:
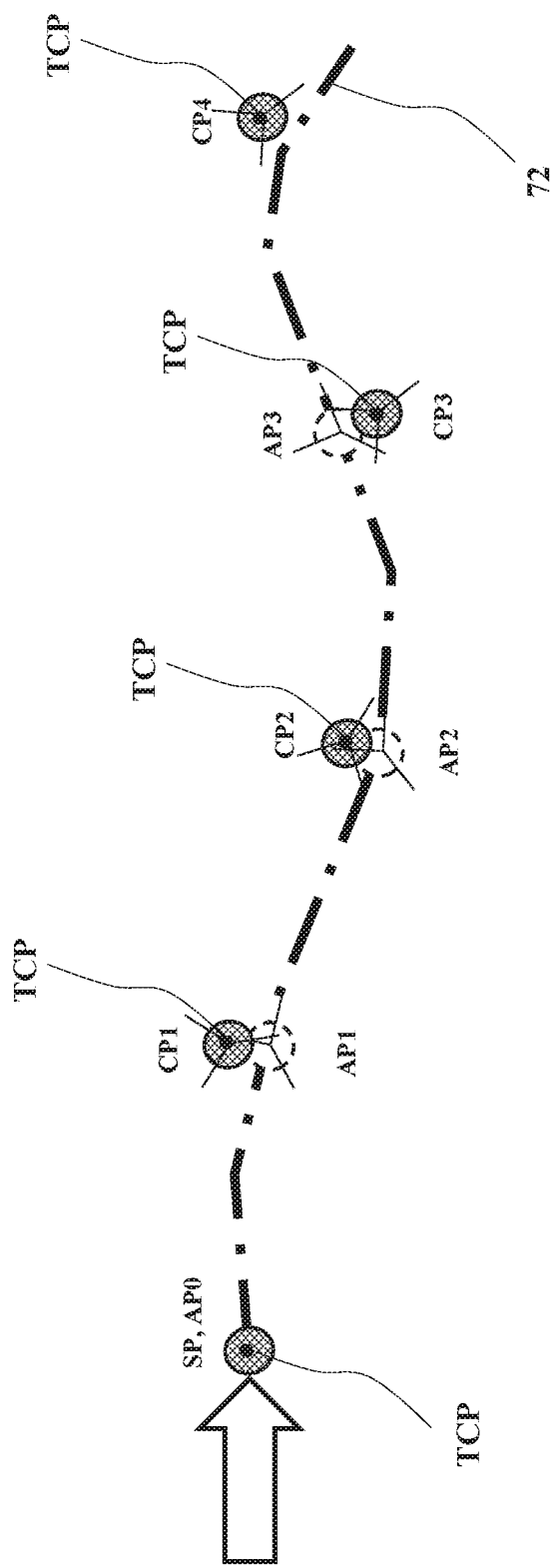
FIG. 18 illustrates a series of movements of the surgical tool along the milling path using the modules of FIG. 10.

The path handler 82 generates the commanded poses CP to be located on the milling path 72 such that the TCP of the tool 20 is generally constrained to movement along the milling path 72. The milling path 72 may be non-linear between consecutive commanded poses CP, so in some iterations the TCP may move off the milling path 72 temporarily, but is generally constrained to return to the milling path 72 by virtue of the commanded poses CP being located on the milling path 72. The description herein of the tool 20 being constrained to movement along the milling path 72 does not require the tool 20 to be restricted to movement only on the milling path 72 but refers to movement generally along the milling path 72 as shown in FIG. 18, for example.

Once the next commanded pose CP is determined, the motion control 76 commands the manipulator 14 to advance the TCP of the tool 20 along the milling path 72 to the next commanded pose CP. Thus, in this version, the control system 60 is configured to command the manipulator 14 to advance the tool 20 along the milling path 72 based on the calculated tangential component of force $F_{ext}$ (tan) and to the exclusion of components of the external force $F_{ext}$ normal to the milling path 72.

Figure 9J:
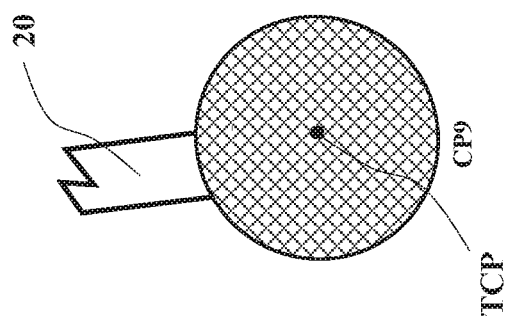

FIGS. 9A to 9J illustrate a number of iterations of the process of FIG. 8, starting from an initial time (t0) to a final time (t9) in which the tool 20 traverses the entire milling path 72, moving from a first commanded pose CP1 (see FIG. 9B) to a final commanded pose CP9 (see FIG. 9J). Initially, to enter the guided-manual mode, the user may provide some form of input into the control system 60, such as via the user interface UI on the tool 20 and/or the manipulator 14, or the guided-manual mode may be selectable via the clinical application 80. The guided-manual mode may also be triggered by moving the tool 20 towards the starting point SP and/or by being within a predefined distance of the starting point SP. One or more of the controllers 21, 26, 36 receive this input and initiate the process shown in FIG. 8. In a first step, at the initial time (t0), the control system 60 generates the lead-in path 72a, as shown in FIG. 9A. Once the lead-in path 72a is generated and the TCP is thereby located on the milling path 72, then the external force $F_{ext}$ at the initial time (t0) can be measured/calculated, applied to the TCP, and resolved into forces normal to the milling path 72 ($F_{ext}$ (n)) and forces tangential to the milling path 72 ($F_{ext}$ (tan)). The next commanded pose of the TCP can then be determined as explained above. The motion control 76 then operates the manipulator 14 to move the TCP to the next commanded pose CP on the milling path 72 (compare FIG. 9A to FIG. 9B, FIG. 9B to FIG. 9C, and so on). This process continues through to the final time (t9) in FIG. 9J. At each iteration, the control system 60 may constrain the orientation of the tool 20 to remain in the same orientation as shown, or may control orientation in other ways, as described above.

At each step shown in FIGS. 9A through 9J, the control system 60 may monitor progress of the tool 20 and virtually remove from the milling path 72 the segments of the milling path 72 traversed by the tool 20. As a result, if the user switches to the semi-autonomous mode after operating for a period of time in the guided-manual mode, then the control system 60 will control the tool 20 to move along only the remaining segments of the milling path 72 not yet traversed while the tool 20 was operating in the guided-manual mode. The control system 60 may also define a new starting point SP for the milling path 72 based on the remaining segments. In other versions, the segments may not be removed so that the milling path 72 remains intact while in the guided-manual mode.

Figure 10:
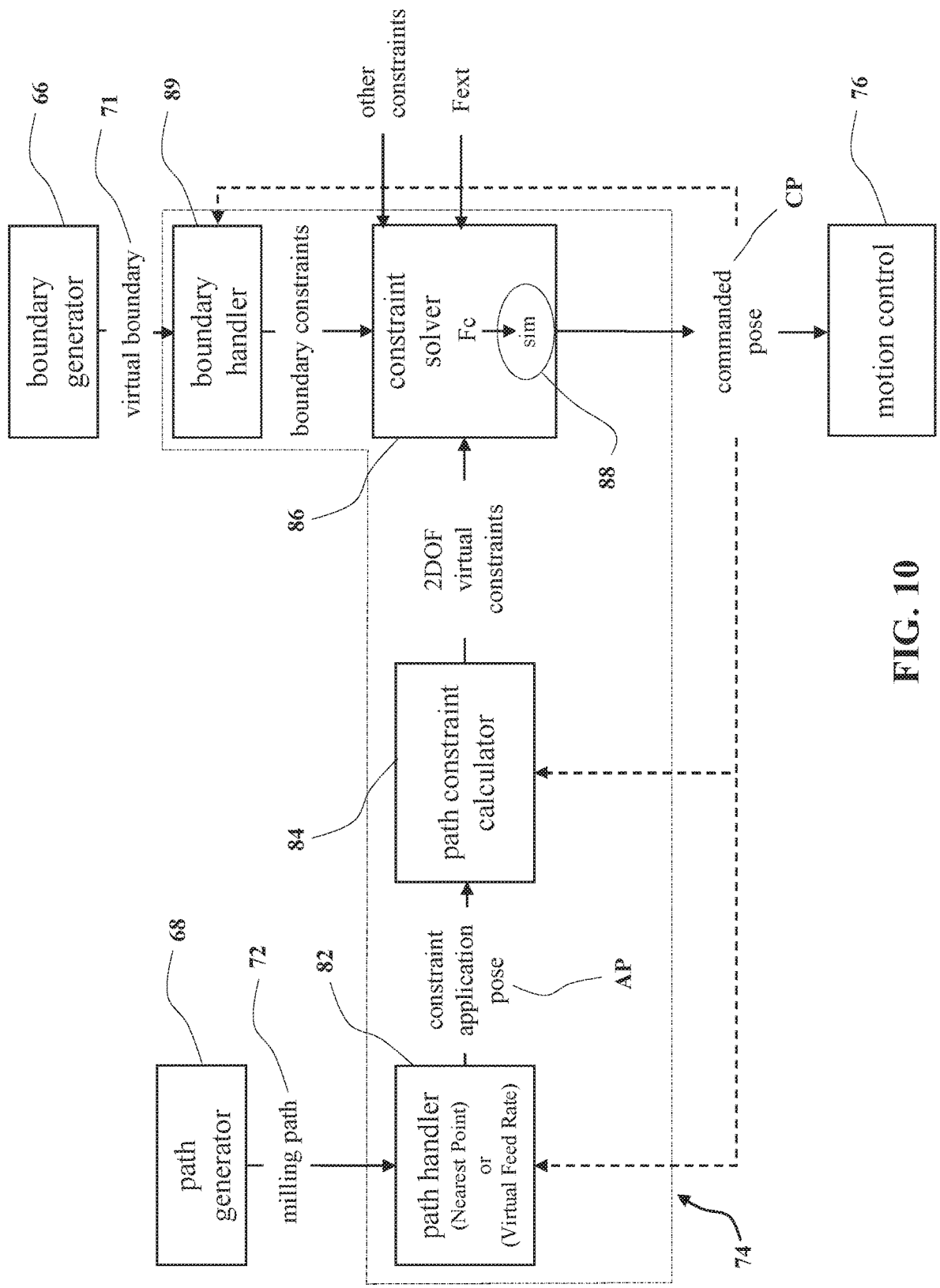
FIG. 10 is a block diagram of modules operable by the control system.

FIG. 10 illustrates processes carried out to execute the guided-manual mode in another example. In this example, the behavior control 74 comprises the path handler 82, and additionally comprises a path constraint calculator 84, a constraint solver 86, and a virtual simulator 88. The behavior control 74 further comprises a boundary handler 89 to generate boundary constraints based on the one or more virtual boundaries 71 generated by the boundary generator 66. In some versions, there are no virtual boundaries 71 being used to constrain movement of the tool 20, and so there would be no boundary constraints employed. The path handler 82, path constraint calculator 84, constraint solver 86, virtual simulator 88, and boundary handler 89 each comprise executable software stored in a non-transitory memory of any one or more of the aforementioned controllers and implemented by the control system 60.

Figure 11:
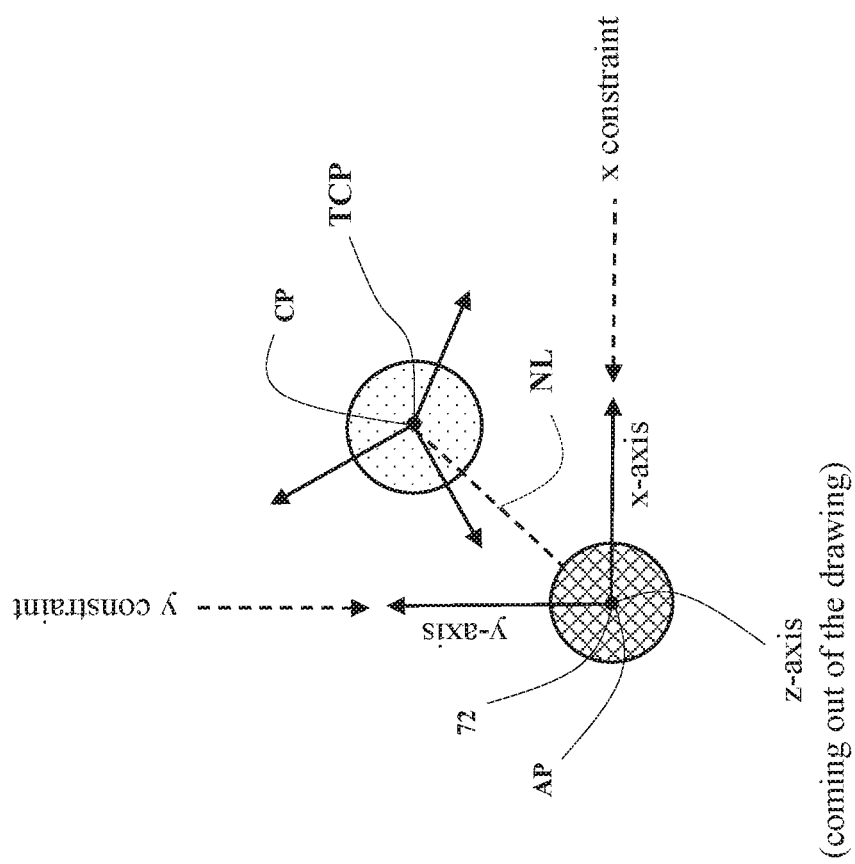
FIG. 11 is an illustration of the milling path, showing the virtual constraints in x and y directions normal to the milling path, and a constraint application pose determined using a "nearest point" method.

In this version, the path handler 82 receives two inputs: the milling path 72 and a previous commanded pose CP. The path handler 82 outputs a constraint application pose AP. The constraint application pose AP is located on the milling path 72, as shown in FIG. 11. The path constraint calculator 84 computes two virtual constraints normal to the milling path 72 as defined by the constraint application pose AP. The constraint solver 86 calculates a constraint force $F_c$ to be virtually applied to the tool 20 in the virtual simulator 88 based on the two virtual constraints where the two virtual constraints act to effectively cancel out components of user forces at the TCP normal to the milling path 72 (which may otherwise cause the TCP of the tool 20 to move normal to the milling path 72), thereby constraining movement of the TCP of the tool 20 to remain along the milling path 72. The virtual simulator 88 may take into account the effects of other forces/constraints as well, as described further below. Ultimately, the virtual simulator 88 calculates a next commanded pose based on its virtual simulation, which ideally causes movement of the tool 20 along the milling path 72. Thus, the user is able to manually manipulate the tool 20, while the control system 60 assists in guiding the tool movement to be along the milling path 72, by utilizing the two virtual constraints. The control system 60 thus assists with guiding the tool movement along the milling path 72 by not defining or at least limiting any constraints to movement of the tool 20 with respect to one degree of freedom being tangential to the milling path 72. The net result is that user forces and torques applied to the tool 20 act to slide the TCP of the tool 20 along the milling path 72. Non-constrained components of the user forces and torques are free to influence the overall movement of the tool 20. Non-constrained forces may include the tangential component of user force at the TCP, as described, but may also include forces/torques that may act to reorient the tool 20. Because there are no constraints in those directions, the virtual simulator 88 does not inhibit movement of the virtual rigid body in those directions.

The constraint application pose AP can be determined/defined using one or more methods. One method is referred to herein as the "nearest point" method and another method is referred to herein as the "virtual feed rate" method. Referring to FIGS. 10 and 11, in the "nearest point" method, the path handler 82 determines each constraint application pose AP by projecting the previous commanded pose CP onto the nearest point on the milling path 72. In most cases, the nearest point on the milling path 72 is defined by a normal line NL extending from the previous commanded pose CP to the milling path 72. Thus, the constraint application pose AP is defined by projecting the previous commanded pose along the normal line NL to the milling path 72. Ideally, the origin of the constraint application pose AP is coincident with the origin of the previous commanded pose if the TCP of the tool 20 is being controlled to be exactly centered on the milling path 72. However, due to the characteristics of the constraints being used (e.g., having configurable stiffness and damping), due to the existence of other constraints, due to the shape of the milling path 72, and/or due to other factors, the previous commanded pose CP may not be perfectly centered on the milling path 72 (see the commanded poses CP1-CP4 in FIG. 18, for example). Thus, the constraint application pose AP is calculated based on the spatial relationship of the previous commanded pose in the utilized coordinate system, relative to the milling path 72, which can also be expressed in the same coordinate system.

In the "nearest point" method, a search process is employed to determine which of the path segments of the milling path 72 is the closest to the previous commanded pose CP. In one embodiment, the search process includes the path handler 82 first performing a broad-phase search to determine a subset of path segments PS within a specified distance of the previous commanded pose CP (e.g., within 1-10 mm, which could be bounded by how far the tool 20 could move relative to the anatomy in one time step at maximum relative velocity). Then, for each of these path segments PS returned from the broad-phase search, the path handler 82 performs a narrow-band search to compute the normal line NL and its length from the previous commanded pose CP to each of these path segments PS. The path handler 82 then selects the normal line NL that has the shortest length. This is the path segment PS to use, i.e., the closest path segment PS to the previous commanded pose CP. Where that normal line NL intersects that path segment PS determines the position of the constraint application pose AP along the milling path 72. This process is repeated each time step as the commanded pose CP is updated.

The orientation component of the constraint application pose AP gives the orientation of the milling path 72 at that point. One possible convention for encoding this orientation information is to choose the z-axis of the constraint application pose coordinate system to be along the milling path 72 (pointing in a positive direction tangentially along the milling path 72) at that point, and the x- and y-axes pointing normal to the milling path 72 at that point (see FIG. 11). Other conventions are possible, as long as the normal and tangent directions of the milling path 72 are captured. This path orientation information is employed by the path constraint calculator 84 to compute the virtual constraints, which with the earlier described convention would be in the x- and y-directions defined by the constraint application pose AP.

The constraint application pose AP can be expressed with respect to a suitable coordinate system, such as the manipulator coordinate system MNPL or localizer coordinate system LCLZ. If the path handler 82 is outputting the constraint application pose AP with respect to the manipulator coordinate system MNPL, then the path handler 82 first employs an appropriate transform computed elsewhere by the control system 60, so that it can convert the milling path pose as well, such as from an anatomy tracker coordinate system to the manipulator coordinate system MNPL (i.e., the milling path 72 may be originally defined with respect to a respective anatomy tracker coordinate frame).

Figure 12:
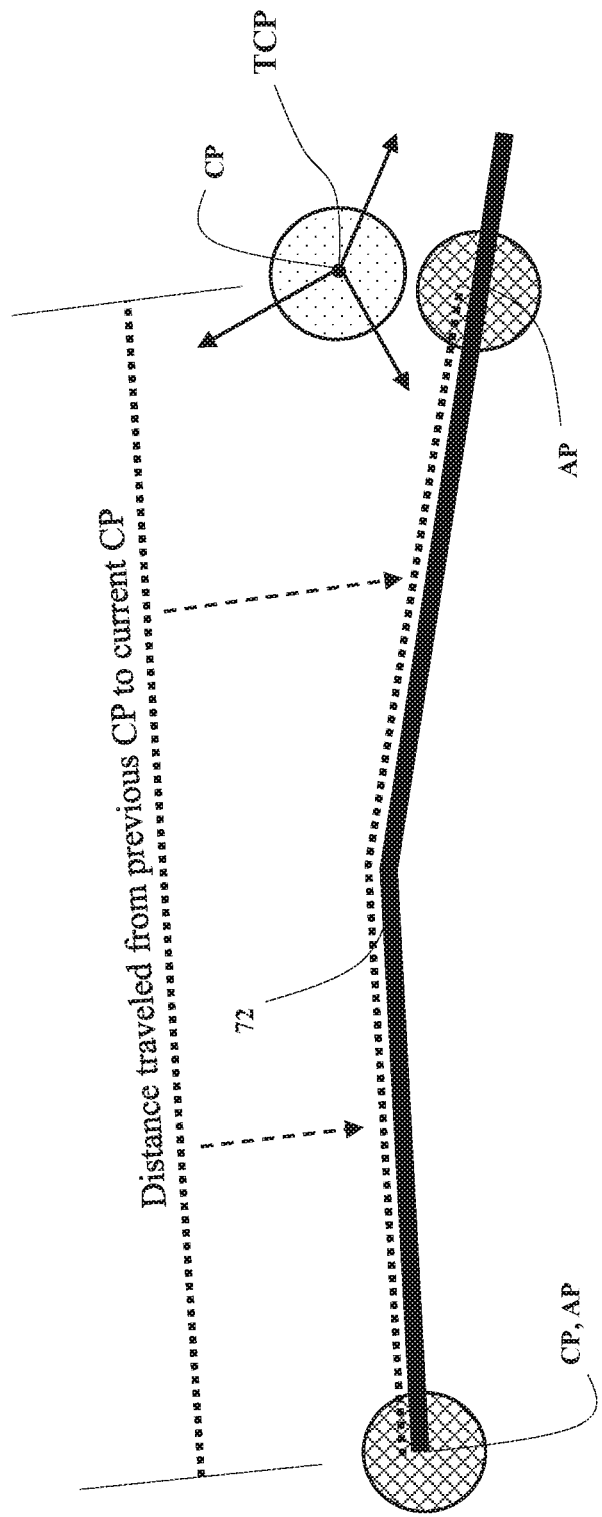
FIG. 12 is an illustration of the milling path, showing the virtual constraints in x and y directions normal to the milling path, and a constraint application pose determined using a "virtual feed rate" method.

In the "virtual feed rate" method, instead of finding the nearest point on the milling path 72, the path handler 82 computes a distance traveled from a previous commanded pose to a current commanded pose CP (see FIG. 12). The path handler 82 then applies this distance along each path segment of the milling path 72 starting from a previous constraint application pose AP (from previous time step) to compute a location of a new constraint application pose AP. More specifically, the path handler 82 steps iteratively within a time step along the milling path 72 one path segment PS at a time until the accumulated distance stepped along the milling path 72 (e.g., path distance) is equal to the computed distance traveled from the previous commanded pose to the current commanded pose CP. This may include the path handler 82 repeatedly checking if the next segment's distance would exceed the computed distance, and if so, the path handler 82 then interpolating linearly within that path segment PS to determine the precise location along the path segment PS where the computed distance is reached. This location becomes the origin of the next constraint application pose AP. This iterative path interpolation process may also include smoothing filters on the interpolated path points, either time domain or spatial, acceleration filters, etc., before setting the result as the origin of the next constraint application pose AP. As with the "nearest point" method, the orientation component of the constraint application pose AP gives the orientation of the milling path 72 at the new constraint application pose AP and can be set as previously described.

Referring back to FIG. 10, the calculated constraint application pose AP is output from the path handler 82 and input into the path constraint calculator 84. The path constraint calculator 84 outputs two virtual constraints (x constraint, y constraint) normal to the milling path 72 at the origin of the constraint application pose AP, as shown in FIG. 11. The path constraint calculator 84 can determine the normal directions using the orientation information of the constraint application pose AP, i.e., its x and y directions, such as when employing the convention for defining the orientation of the constraint application pose AP described above.

As previously described, the two virtual constraints are provided to effectively cancel out components of user forces at the TCP normal to the milling path 72. Without canceling such normal components of user forces, the TCP of the tool 20 could otherwise move away from the milling path 72. The two virtual constraints thereby act to constrain movement of the TCP of the tool 20 so that the TCP remains generally on the milling path 72. The virtual constraints are defined so that virtual forces can be calculated and applied in the virtual simulation to cancel out the components of user forces at the TCP normal to the milling path 72, and hold the user on the milling path 72 with suitable accuracy. In some versions, the two virtual constraints are velocity impulse constraints. In some versions, the constraints are similar to those used in the impulse modeling described in U.S. Pat. No. 9,119,655, incorporated herein by reference. In some versions, these virtual constraints are defined exclusively in the guided-manual mode, and not in the manual mode or the semi-autonomous mode. In some versions, virtual constraints are used in all modes.

As previously noted, the control system 60 may not provide any constraints to movement of the tool 20 with respect to one degree of freedom being tangential to the milling path 72. For example, the path constraint calculator 84 may define the virtual constraints in only two degrees of freedom, normal to the milling path 72, but not define or provide any constraints with respect to the degree of freedom tangential to the milling path 72. As described further below, however, other constraints employed in the behavior control 74 may affect movement of the tool 20 tangential to the milling path 72, such as damping constraints, boundary constraints, etc. For example, in some cases, one or more virtual constraints could be defined in the tangential direction along the milling path 72 to provide damping. These damping constraints could be tuned as desired to control how easy or difficult movement along the milling path 72 in the guided-manual mode feels to the user. Less damping makes it easier to move the tool. More damping is sometimes desired to provide increased stability while machining.

Figure 13:
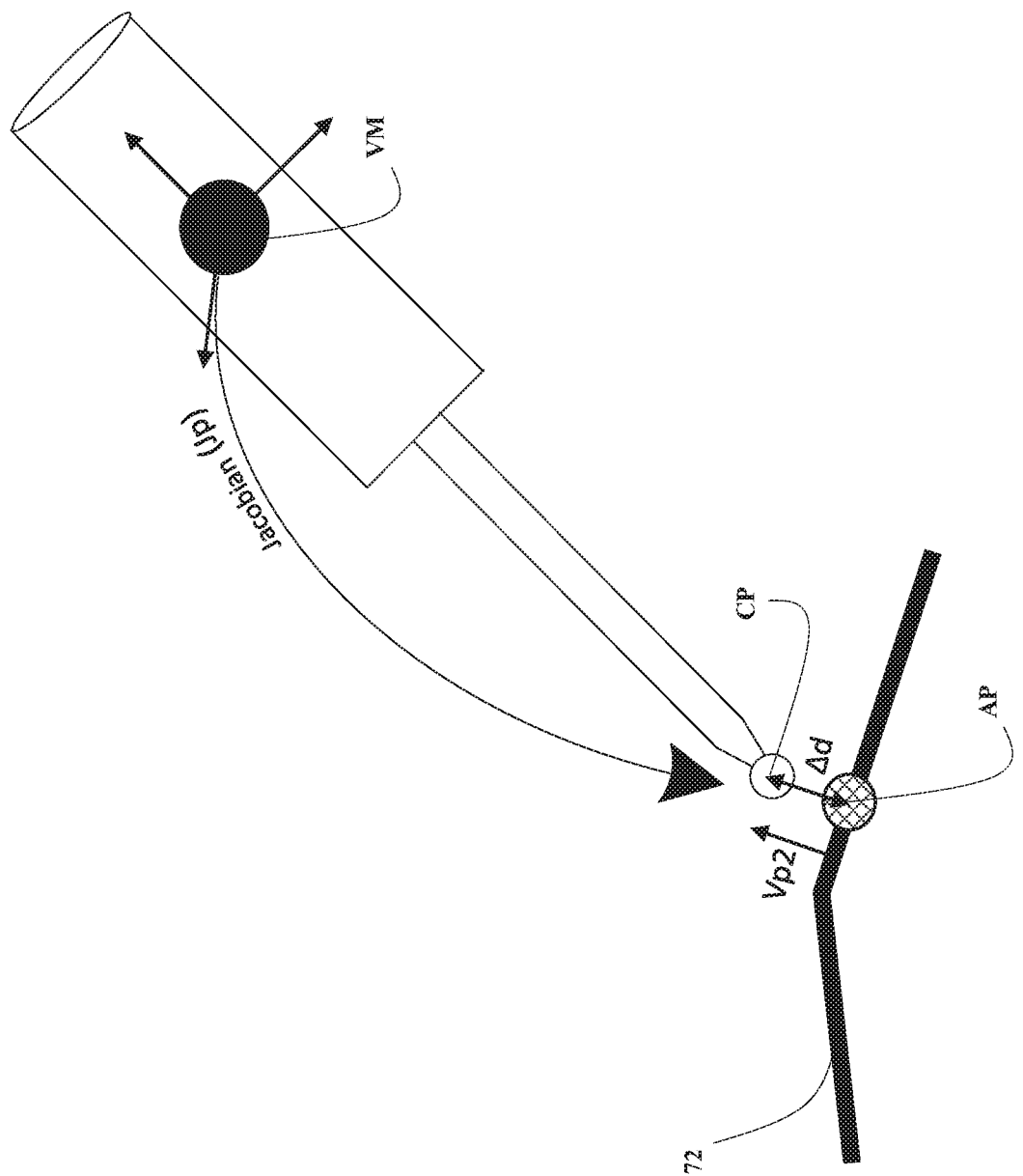
FIG. 13 is an illustration of a virtual rigid body and constraint parameters.

Referring to FIG. 13, the virtual constraints are defined primarily by three runtime parameters: a constraint Jacobian Jp, which maps each one-dimensional, virtual constraint between a constraint coordinate system and a coordinate system employed for the virtual simulation (e.g., between the constraint application pose coordinate system and the virtual mass coordinate system VM); a desired velocity Vp2, which is a scalar velocity of the constraint in the constraint coordinate system (e.g., the desired velocity may be zero when the patient is immobile and the associated milling path 72 defined relative to the patient is not moving, but may be other than zero when the patient moves since the milling path 72 is tied to the patient); and a constraint distance Ad, which is how close the TCP is to the constraint and dictates whether the constraint is being violated. In this case, Ad refers to a distance from the milling path 72, and the two virtual constraints are violated any time the distance is greater than zero in the x and y directions.

In some embodiments, the virtual constraints are not perfectly rigid, but instead each of the virtual constraints has tuning parameters to adjust the stiffness of the virtual constraints, e.g., by incorporating spring and damping parameters into the constraints.

Each virtual constraint also has configuration settings. The configuration settings may comprise: information regarding tuning parameters, such as a constraint force mixing parameter (C) and an error reduction parameter (E); upper and/or lower force limits; and/or upper and lower constraint distance offsets. The upper and lower force limits refer to limits on the forces computed for each constraint that are ultimately solved by the constraint solver 86 to produce a constraint force $F_c$, as described further below. Since the two virtual constraints being provided by the path constraint calculator 84 are two-sided constraints (e.g., the constraint forces computed to satisfy the constraints can be positive or negative), the force limits can be set high in positive and negative directions (e.g., −100,000/+100,000 Newtons) or at any desired limit. The upper and lower constraint distance offsets dictate when the constraint is active. With respect to the two virtual constraints described above, the upper and lower constraint distance offsets can be set so that the constraint is active any time the TCP is off the milling path 72 (e.g., at 0 mm).

Referring to FIG. 14, the constraint parameters for each virtual constraint are passed into the constraint solver 86 by the path constraint calculator 84. The constraint solver 86 places the constraint data for each constraint into a corresponding row of a constraint equation, in matrix form, to solve for $F_p$. The constraint data is placed in the constraint equation, along with other information known by the constraint solver 86, such as the external force $F_{cgext}$, a damping force $F_{damping}$, an inertial force $F_{inertial}$, the virtual mass matrix M, a virtual mass velocity $V_{cg1}$, and the time step $\Delta t$ (e.g., 125 microseconds).

The virtual mass matrix M combines 3×3 mass and inertia matrices. The damping and inertial forces $F_{damping}$ and $F_{inertial}$ are calculated/known by the virtual simulator 88 and are based on the virtual mass velocity $V_{cg1}$ (e.g., the velocity of the virtual mass coordinate system VM) output by the virtual simulator 88 in a prior time step. The virtual mass velocity $V_{cg1}$ is a 6-DOF velocity vector comprising linear and angular velocity components. The damping force $F_{damping}$ is a 6-DOF force/torque vector computed as a function of the virtual mass velocity $V_{cg1}$ and a damping coefficient matrix (linear and rotational coefficients may not be equal). Damping is applied to the virtual mass Vm to improve its stability. The inertial force $F_{inertial}$ is also a 6-DOF force/torque vector computed as a function of the virtual mass velocity $V_{cg1}$ and the virtual mass matrix M. The damping and inertial forces, $F_{damping}$ and $F_{inertial}$, can be determined in the manner described in U.S. Pat. No. 9,566,122 to Bowling et al., hereby incorporated herein by reference.

Referring to the constraint equation shown in FIG. 14, $F_p$ is a force vector in the constraint coordinate system, i.e., each component of $F_p$ is a scalar constraint force acting in the corresponding constraint direction. In order to solve for $F_p$, as describe below, the equation shown in FIG. 14 is converted into a matrix equation where each row represents a single, one-dimensional constraint.

The constraint solver 86 may be configured with any suitable algorithmic instructions (e.g., an iterative constraint solver, Projected Gauss-Seidel solver, etc.) to solve this system of constraint equations in order to provide a solution best satisfying the system of equations (e.g., best satisfying the various constraints). In some cases, all constraints may not simultaneously be met. For example, in the case where motion is overconstrained by the various constraints, the constraint solver 86 will essentially find a 'best fit' solution given the relative stiffness/damping of the various constraints. The constraint solver 86 solves the system of equations and ultimately outputs the constraint force $F_c$.

When a Projected Gauss-Seidel solver is employed, the constraint solver 86 constructs A and b matrices based on the constraints, uses Projected Gauss-Seidel to solve the system of equations to determine the resulting force vector $F_p$, takes the output of Projected Gauss-Seidel and transforms it from the constraint coordinate system to the virtual mass coordinate system VM. For example, using the equation $F_c = J_p^T F_p$, wherein $F_c$ is the constraint force, each resulting force vector $F_p$ is converted to a force/torque vector applied to the virtual mass coordinate system VM.

Methods of using Projected Gauss-Seidel to solve a system of equations for multiple constraints is shown, for example, in "Constraint based physics solver" by Marijn Tamis and Giuseppe Maggiore, dated Jun. 15, 2015 (v1.02), which can be found at http://www.mft-spirit.nl/files/MTamis_ConstraintBasedPhysicsSolver.pdf, or in "Comparison between Projected Gauss-Seidel and Sequential Impulse Solvers for Real-Time Physics Simulations," by Marijn Tamis, dated Jul. 1, 2015 (v1.01), which can be found at http://www.mft-spirit.nl/files/MTamis_PGS_SI_Comparison.pdf, both of which are hereby incorporated herein by reference in their entirety.

The Projected Gauss-Seidel method addresses Linear Complementarity Problems (LCP). Inequality associated with LCP arises since some constraint types (e.g., one-sided constraints, such as the boundary constraints) can only push (apply force) in one direction, e.g., positive constraint force. If the calculated force for such a constraint is negative (or, more broadly, outside its allowed range) for a given iteration of the constraint solver 86, which is invalid, the given constraint must be pruned (or alternately limited/capped at its upper or lower allowed value) and the remaining constraints solved, until a suitable result (i.e., convergence) is found. In this manner, the constraint solver 86 determines the active set of constraints for a given time step, and then solves for their values. Other constraint types can apply forces in both positive and negative directions, e.g., two-sided constraints. Such constraints include the x and y virtual constraints used to hold the tool 20 on the milling path 72 to limit movement in the normal direction to the milling path 72. Such two-sided constraints, when enabled, are usually active and not pruned/limited during the constraint solver 86 iterations.

The constraint force $F_c$ calculated by the constraint solver 86 comprises three components of force along x, y, z axes and three components of torque about the x, y, z axes. The virtual simulator 88 utilizes the constraint force $F_c$, along with the external force $F_{cgext}$, the damping force $F_{damping}$, and the inertial force $F_{inertial}$ (all of which may comprise six components of force/torque), in its virtual simulation. In some cases, these components of force/torque are first transformed into a common coordinate system (e.g., the virtual mass coordinate system VM) and then summed to define a total force FT. The resulting 6-DOF force (i.e., force and torque) is applied to the virtual rigid body and the resulting motion is calculated by the virtual simulator 88. The virtual simulator 88 thus acts to effectively simulate how the various constraints, among other things, affects motion of the virtual rigid body. The virtual simulator 88 performs forward dynamics to calculate the resulting 6-DOF pose and velocity of the virtual rigid body based on the given total force FT being applied to the virtual rigid body. In one example, the virtual simulator 88 comprises a physics engine, which is executable software stored in a non-transitory memory of any one or more of the aforementioned controllers 21, 26, 36 and implemented by the control system 60.

For the virtual simulation, the virtual simulator 88 models the tool 20 as the virtual rigid body in the virtual mass coordinate system VM with the origin of the virtual mass coordinate system VM being located at the center of mass of the virtual rigid body, and with the coordinate axes being aligned with the principal axes of the virtual rigid body (see, e.g., FIG. 13). The virtual rigid body is a dynamic object and a rigid body representation of the tool 20 for purposes of the virtual simulation. The virtual rigid body is free to move according to six degrees of freedom (6-DOF) in Cartesian space according to the virtual simulation. The virtual simulation may be processed computationally without visual or graphical representations. Thus, it is not required that the virtual simulation display dynamics of the virtual rigid body. In other words, the virtual rigid body need not be modeled within a graphics application executed on a processing unit. The virtual rigid body may exist only for the virtual simulation.

The virtual rigid body and its properties (mass, inertia matrix, center of mass, principal axes, etc.) define how the tool 20 will move in response to applied forces and torques (applied by the user via the force/torque sensor S and based on the action of calculated constraint forces). It governs whether the tool 20 will feel heavy or light and how it will move (e.g., accelerate in translation and rotation) in response to applied forces and torques. By adjusting the properties of the virtual rigid body, the control system 60 can adjust how the tool 20 feels to the user. It may be desirable to have the properties of the virtual rigid body modeled to be reasonably close to the actual properties of the tool 20, for as realistic motion/feel as possible, but that is not required. For control stability reasons (given the finite acceleration of the robot system, control latencies, etc.), the virtual mass and inertia may be modeled to be somewhat higher than that of the tool 20.

The virtual rigid body may correspond to components, which may be on or within the tool 20. Additionally or alternatively, the virtual rigid body may extend, in part, beyond the tool 20. The virtual rigid body may take into account the tool 20 with the energy applicator 24 or may take into account the tool 20 without the energy applicator 24. Furthermore, the virtual rigid body may be based on the TCP. In one example, the center of mass of the virtual rigid body is understood to be the point around which the virtual rigid body would rotate if a virtual force is applied to another point of the virtual rigid body and the virtual rigid body were otherwise unconstrained, i.e., not constrained by the manipulator 14. The center of mass of the virtual rigid body may be close to, but need not be the same as, the actual center of mass of the tool 20. The center of mass of the virtual rigid body can be determined empirically. Once the tool 20 is attached to the manipulator 14, the position of the center of mass can be reset to accommodate the preferences of the individual practitioners.

The virtual simulator 88 effectively simulates rigid body dynamics of the tool 20 by virtually applying forces and/or torques on the virtual rigid body, i.e., by virtually applying the components of force and torque from the total force FT on the center of mass of the virtual rigid body in the virtual mass coordinate system VM. Thus, the forces/torques virtually applied to the virtual rigid body may comprise forces/torques associated with the external force $F_{cgext}$, the damping force $F_{damping}$, the inertial force $F_{inertial}$, and the forces/torques from the constraint force $F_c$ associated with the various constraints (by virtue of being embodied in the constraint force $F_c$).

Rigid body Jacobians can be used to transform velocities and forces from one coordinate system (reference frame) to another on the same virtual rigid body and may be employed here to transform the forces and torques of $F_{ext}$ to the virtual mass coordinate system VM as well (e.g., to yield $F_{cgext}$ used in the constraint equation). The virtual simulator 88 then internally calculates the damping force $F_{damping}$ and the inertial force $F_{inertial}$ to determine the total force $F_T$, and also to output the damping force $F_{damping}$ and the inertial force $F_{inertial}$ for use by the constraint solver 86 in its system of equations in the next time step.

Figure 16:
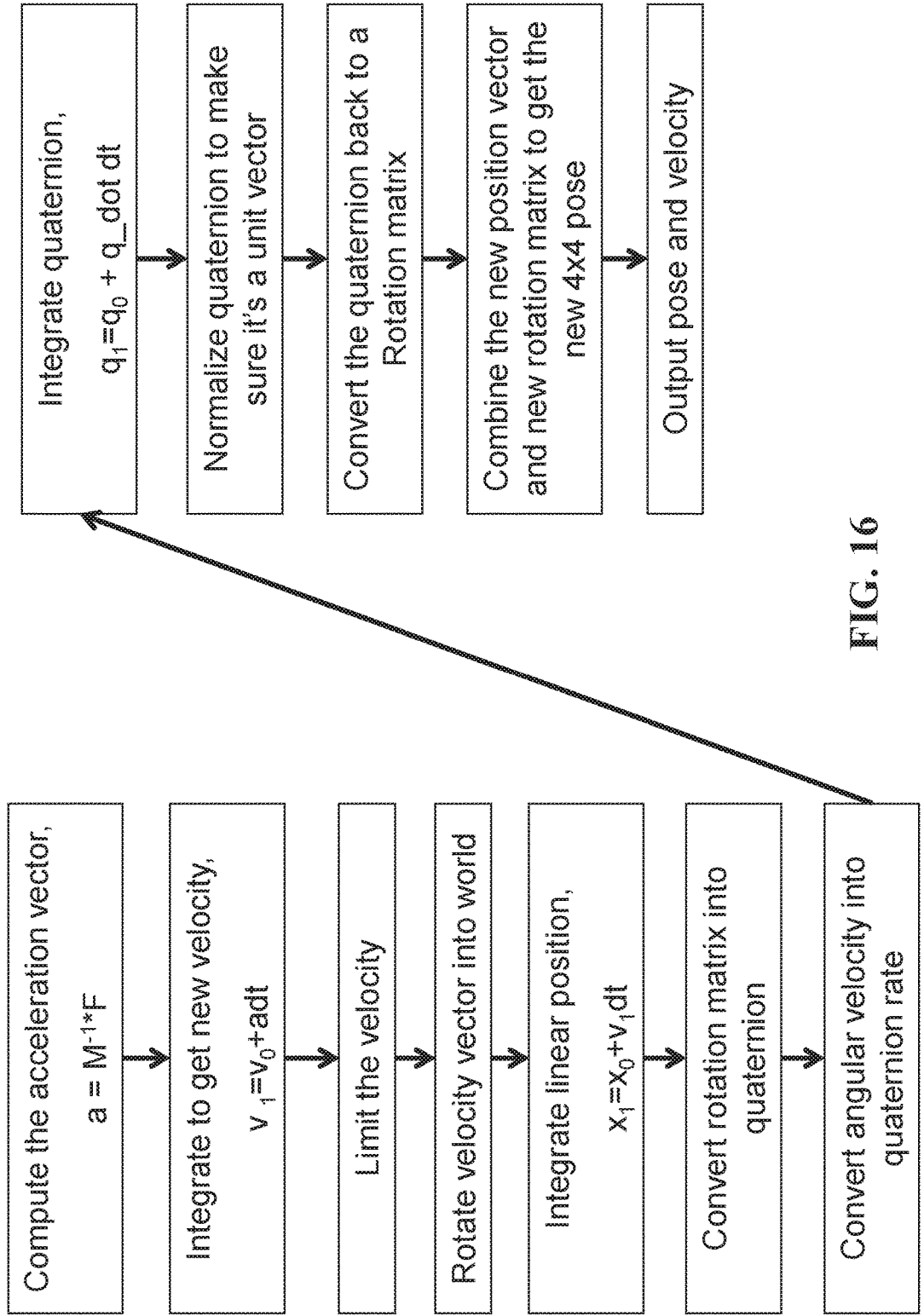
Figure 17:
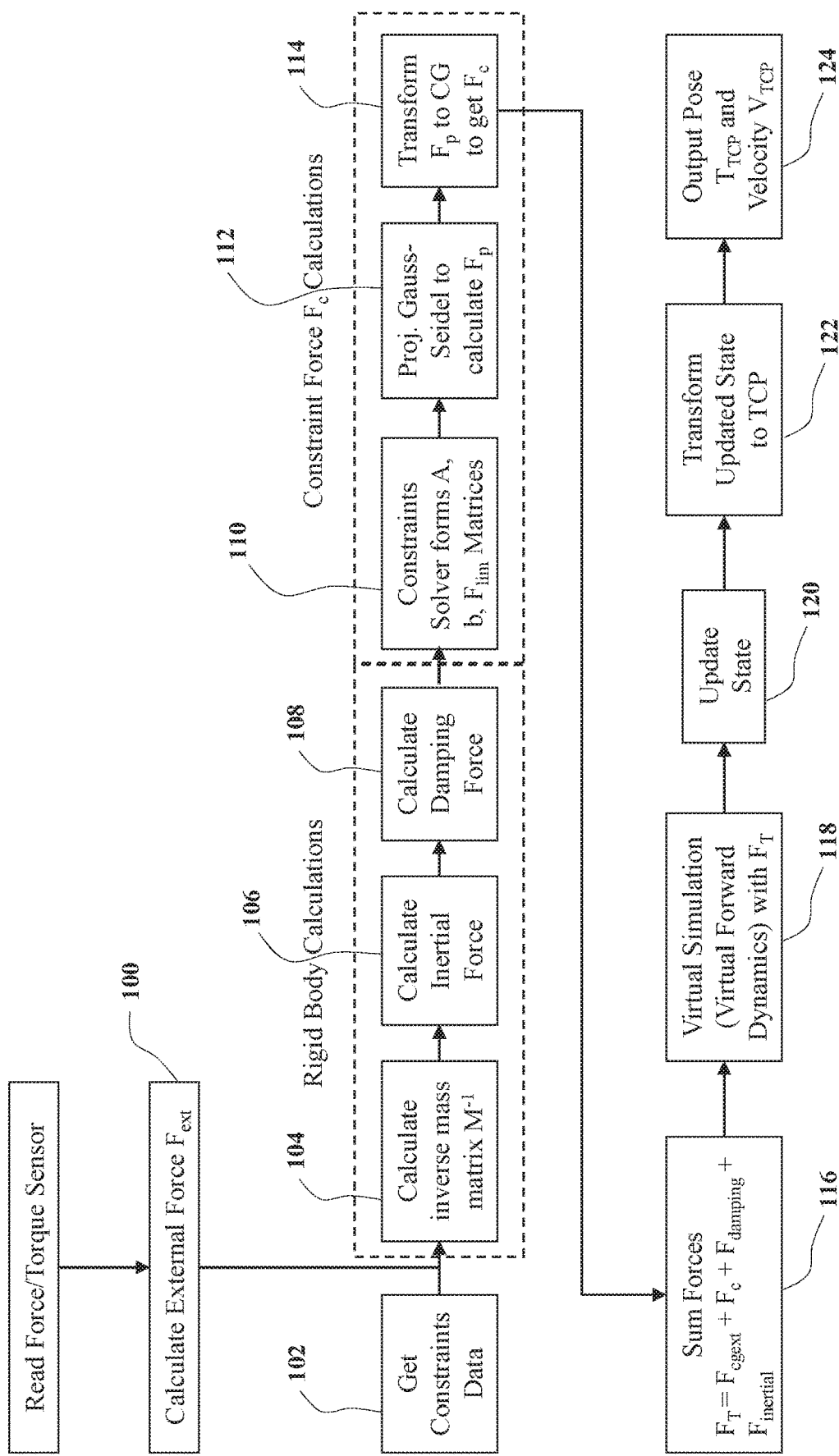
FIG. 17 shows an example set of steps carried out by the control system to solve constraints, perform forward dynamics, and determine a commanded pose.

A virtual forward dynamics algorithm, as shown in FIGS. 16 and 17, may be employed in the virtual simulation to simulate the motion of the virtual rigid body as it would move upon application of the total force $F_T$. Effectively, the virtual forward dynamics algorithm solves the equation F=ma (or a=F/M) in 6-DOF and integrates the acceleration to yield velocity, which is then used to determine a new pose, as shown in FIG. 17. The control system 60 inputs the virtual forces and/or torques (e.g., the total force $F_T$) into the virtual simulator 88 and these virtual forces and/or torques are applied to the virtual rigid body at the center of mass (e.g., the CG) in the virtual simulation 88 when the virtual rigid body is in the initial pose with the initial velocity. The virtual rigid body is moved to a final pose having a different state (i.e., position and/or orientation) and with a final velocity within Cartesian space in response to the control system 60 satisfying the inputted virtual forces and/or torques. The next commanded pose CP to be sent to the motion control 76 is based on the final pose calculated by the virtual simulator 88. Thus, the virtual simulator 88 operates to determine the next commanded pose CP by simulating the effects of applying the total force $F_T$ on the virtual rigid body using virtual forward dynamics as shown in FIG. 16.

Velocity limits may be imposed on the virtual rigid body in the simulation. In some cases, the velocity limits may be set high so that they generally don't affect the simulation, or they may be set at any desired value. The virtual rigid body is in an initial pose (initial state) and has an initial velocity at commencement of each iteration of the virtual simulation (e.g., at each time step/interval dt). The initial pose and initial velocity may be defined as the final pose and the final velocity output by the virtual simulator 88 in the previous time step.

FIG. 17 summarizes various steps carried out by the behavior control 74. These include steps performed by the constraint solver 86 and the virtual simulator 88 as described above. In step 100, the external force $F_{ext}$ is calculated based on readings taken from the force/torque sensor S. In step 102, the constraints data associated with the various virtual constraints are fed into the constraint solver 86 from the path constraint calculator 84, from the boundary handler 89, and/or from other constraint sources.

In steps 104-108, rigid body calculations are carried out by the virtual simulator 88 to determine the inverse mass matrix $M^{-1}$, the inertial force $F_{inertial}$, and the damping force $F_{damping}$ of the virtual rigid body. In steps 110-114, the constraint solver 86 utilizes the output from the rigid body calculations performed in steps 104-108 and the constraints data provided in step 102 to perform the constraint force calculations previously described to ultimately yield the constraint force F. In step 116, the constraint force $F_c$ is summed with the external force $F_{cgext}$, the damping force $F_{damping}$, and the inertial force $F_{inertial}$ to yield the total force $F_T$. In step 118, the total force $F_T$ is applied to the virtual rigid body in the virtual simulation conducted by the virtual simulator 88 to determine a new pose and velocity of the virtual rigid body in step 120, and ultimately to transform the new pose and velocity to the TCP in step 122. The new commanded pose CP ($T_{TCP}$), and velocity ($V_{TCP}$) are output by the virtual simulator 88 in step 124.

FIG. 18 illustrates motion of the TCP of the tool 20 along the milling path 72 in the guided-manual mode using the process of FIG. 10. The TCP of the tool 20 moves from the starting position SP to a first commanded pose CP1, then to a second commanded pose CP2, then to a third commanded pose CP3, and finally to a fourth commanded pose CP4. Along the way, the control system 60 executes the process set forth in FIG. 10 to determine the series of constraint application poses AP0, AP1, AP2, AP3, so that the control system 60 is able to determine each subsequent commanded pose CP. The purpose of each of the constraint application poses AP0, AP1, AP2, AP3, as described above, is to provide a reference pose at which to define the two virtual constraints so that the TCP remains generally on the milling path 72 at each iteration. For example, after the TCP moves to the first commanded pose CP1, the path handler 82 then calculates the first constraint application pose AP1 (e.g., with x- and y-axes normal to the milling path 72 using the convention previously described), and the path constraint calculator 84 thereafter calculates the two normal, virtual constraints to be applied to the TCP of the tool 20 so that the next commanded pose CP2 of the TCP of the tool 20 is along the milling path 72.

Figure 19A:
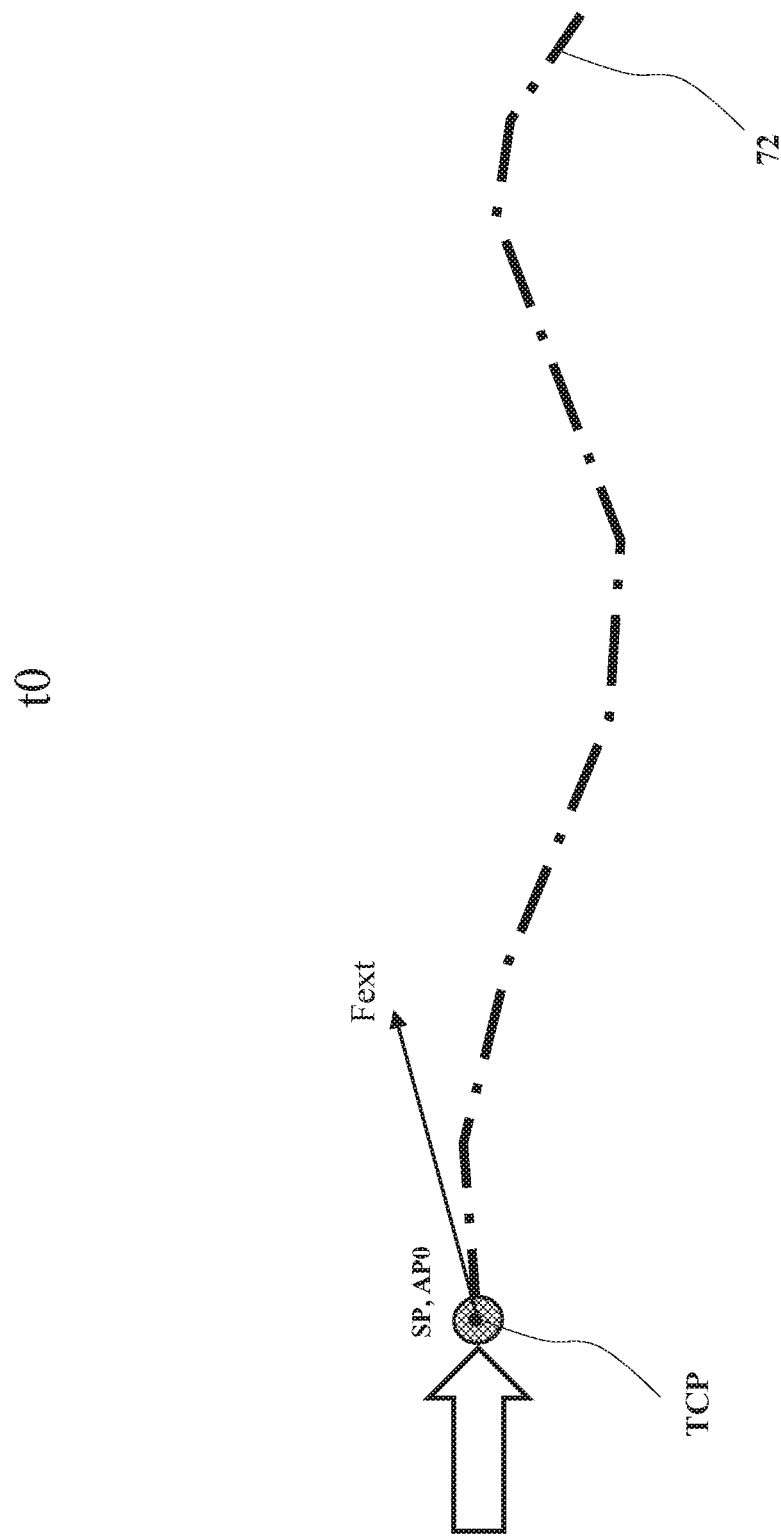
FIGS. 19A-19E illustrate each of the movements of the surgical tool along the milling path shown in FIG. 18.
Figure 19B:
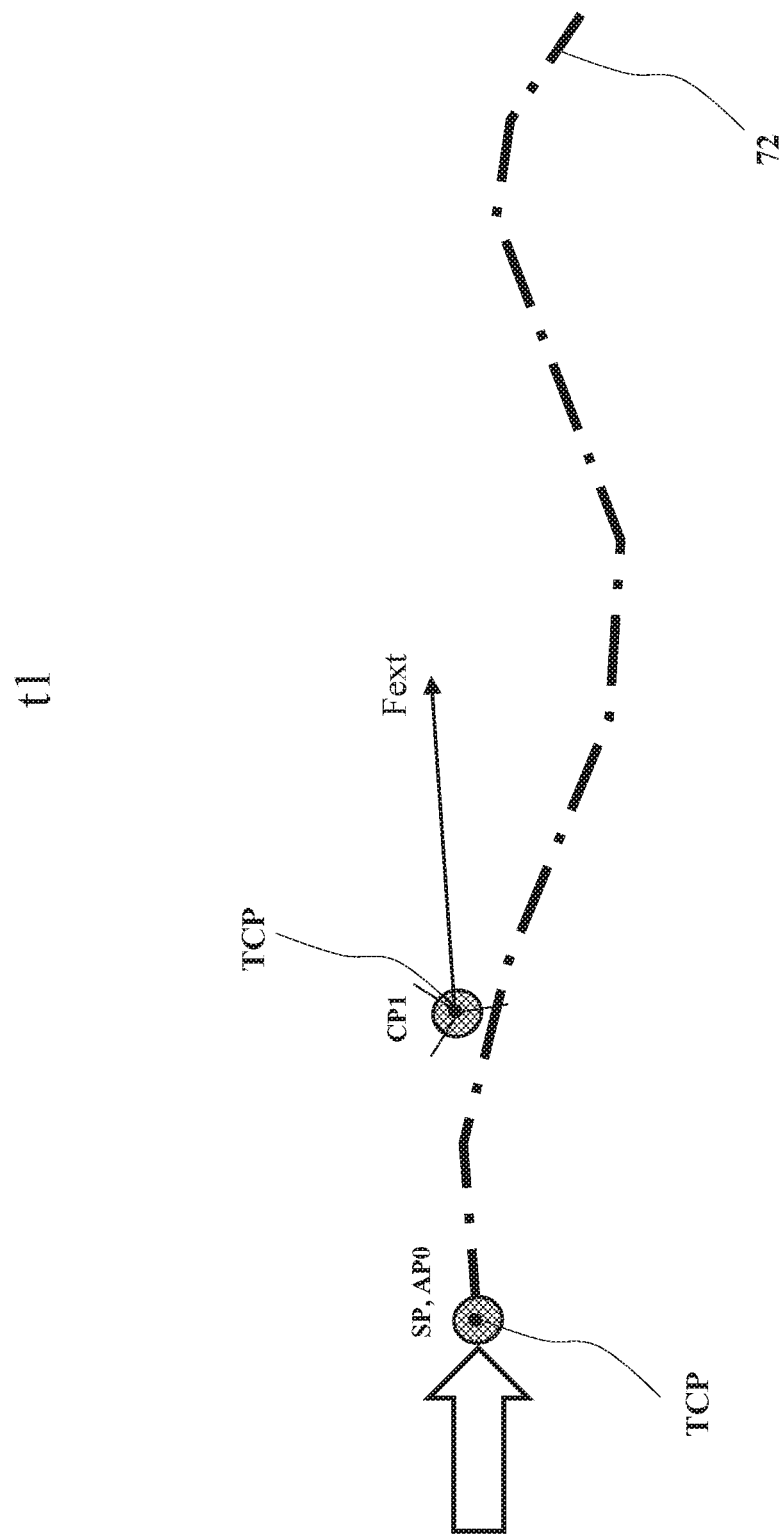
Figure 19C:
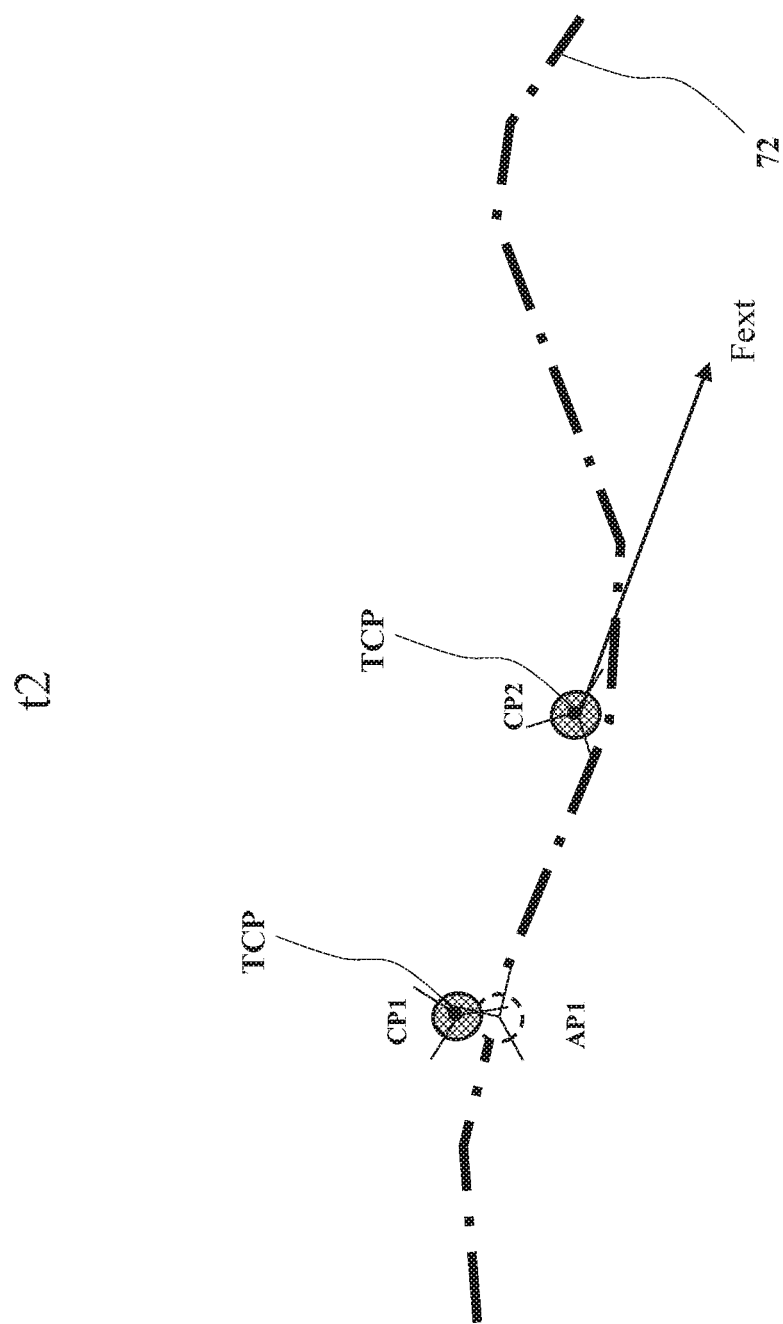
Figure 19D:
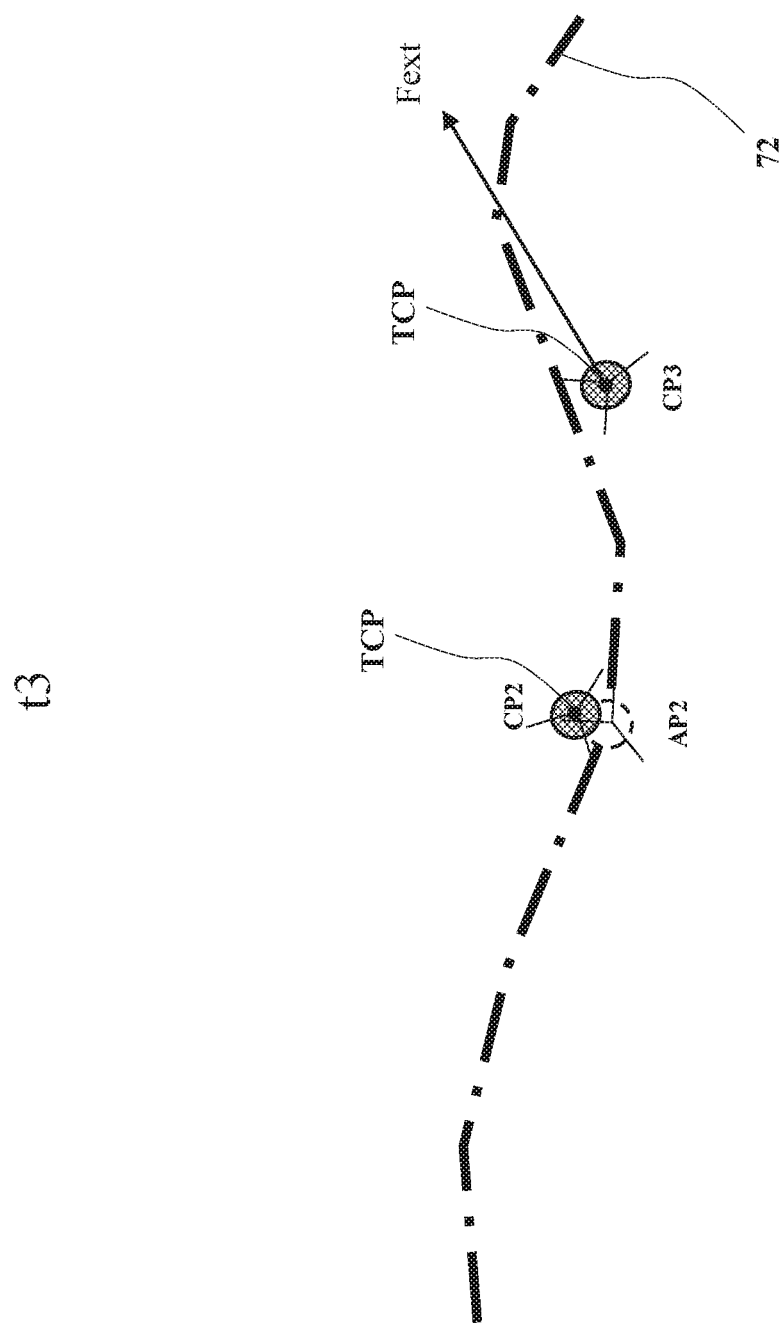
Figure 19E:
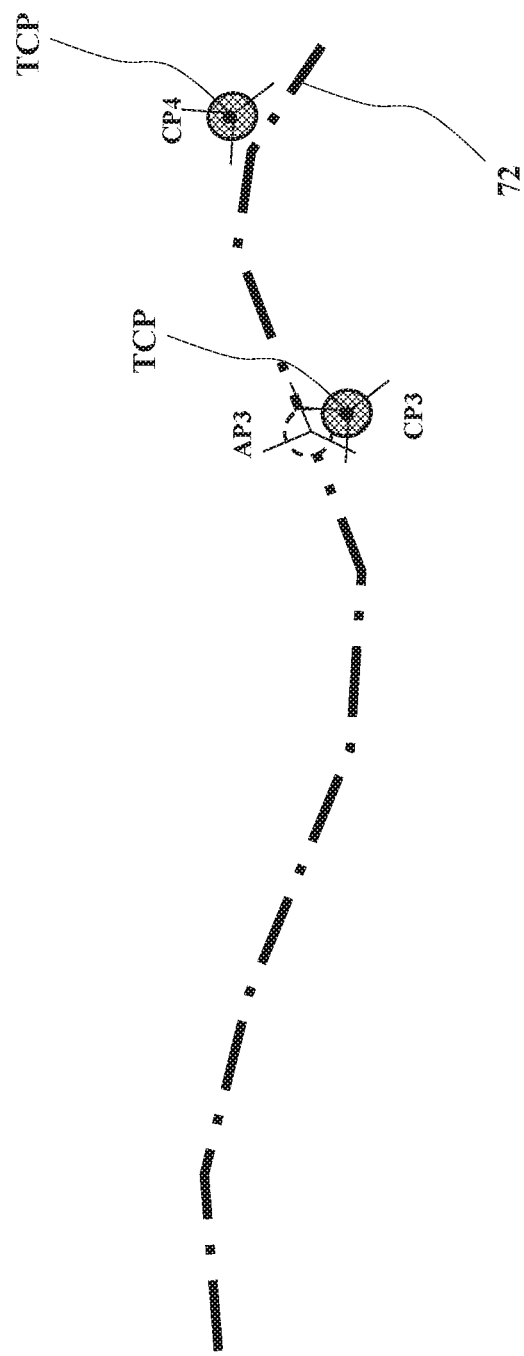

FIGS. 19A through 19E show the process being carried out from an initial time (t0) to a final time (t4). It should be noted that the application of user forces in the tangential direction along the milling path 72 causes the TCP of the tool 20 to slide generally along the milling path 72, but in the absence of any external force $F_{ext}$, the TCP would simply move from the previous commanded pose CP toward the next constraint application point AP. For example, referring to FIG. 19B and FIG. 19C, if there was no external force $F_{ext}$ applied as shown in FIG. 19B, then the TCP would have been pulled towards the constraint application pose AP1 shown in FIG. 19C (e.g., the next commanded pose CP2 would be near or at the constraint application pose AP1, as opposed to being further along the milling path 72 as shown). This resulting movement is due to $F_{ext}$. Any off-path components of $F_{ext}$ are effectively canceled out by the constraint force $F_c$, and the remaining (unconstrained) force components along the milling path 72 are allowed to slide the tool 20. At each time step, the tool 20 can slide along the tangent line (defined by the z direction of the constraint application pose AP), and since the milling path 72 may be curved and the virtual constraints not infinitely stiff, the tool 20 may deviate slightly from the milling path 72 each time step. However, this deviation is compensated for the next time step by the action of the continually updating (i.e., at each time step) normal virtual constraints and resulting constraint force F.

In some versions, the control system 60 operates to address behavior of the tool 20 at the start and/or end of the milling path 72 so that the user does not inadvertently over-machine and/or "slip off" the ends of the milling path 72. To provide a rigid boundary at the ends of the milling path 72, additional constraints, such as additional virtual constraints output by the path constraint calculator 84 may feed into the constraint solver 86. For example, an end constraint may be added that is applied in the tangential direction (i.e., along the milling path 72), with the constraint applied in a direction which opposes movement that would result in moving past the start/end of path. Where the two virtual constraints implemented normal to the path direction are "two-sided" constraints (meaning they can yield both positive/negative forces as needed), the end constraint is a "one-sided" constraint (which can yield force only in the "positive" tangential direction as needed). The end constraint is defined tangentially along the milling path 72.

The path handler 82 generates/sets an indicator (e.g., a flag or flags, such as 'start path' or 'end path' flags) that is sent to the path constraint calculator 84 along with the constraint application pose AP to trigger the path constraint calculator 84 to output the one-sided constraint in the tangential direction and oppose movement in the tangential direction such that it prevents further movement along the milling path 72, but only in the direction that would result in the user progressing past the end of the milling path 72. The direction of the end constraint may be based on the constraint application pose AP (e.g., applied opposite to its positive z-axis direction when approaching the end of path or applied in the positive z-axis direction when at the start of path). Other sign conventions to define the end constraint are also possible. For example, the constraint application pose AP may be set so that its positive z-axis direction is always pointing tangentially along the milling path 72 in a direction towards interior segments of the milling path 72 (i.e., the positive z-axis would be flipped once the midway point of the milling path 72 is reached). In this case, the end constraint would be applied in the positive tangential direction.

When the software detects the constraint application pose AP is at one of the end-of-path locations, it will enable the end constraint defined above; otherwise the end constraint is disabled. This approach allows the user to guide the tool 20 smoothly forward and backwards along the milling path 72, but to have a firm stop (i.e., additional force feedback, with configurable stiffness/damping) at the corresponding ends of the milling path 72. If a firm end-of-path behavior is not desired (i.e., if it's desired for the user to "fall off" the ends), an alternate approach would be to use the previously defined two virtual constraints normal to the milling path 72, and simply turn them both off when an end-of-path target is reached (as determined by the path handler 82), allowing the tool 20 to move freely. This behavior could be accompanied by user feedback on the displays 38, audible feedback, and/or haptic feedback.

Figure 20:
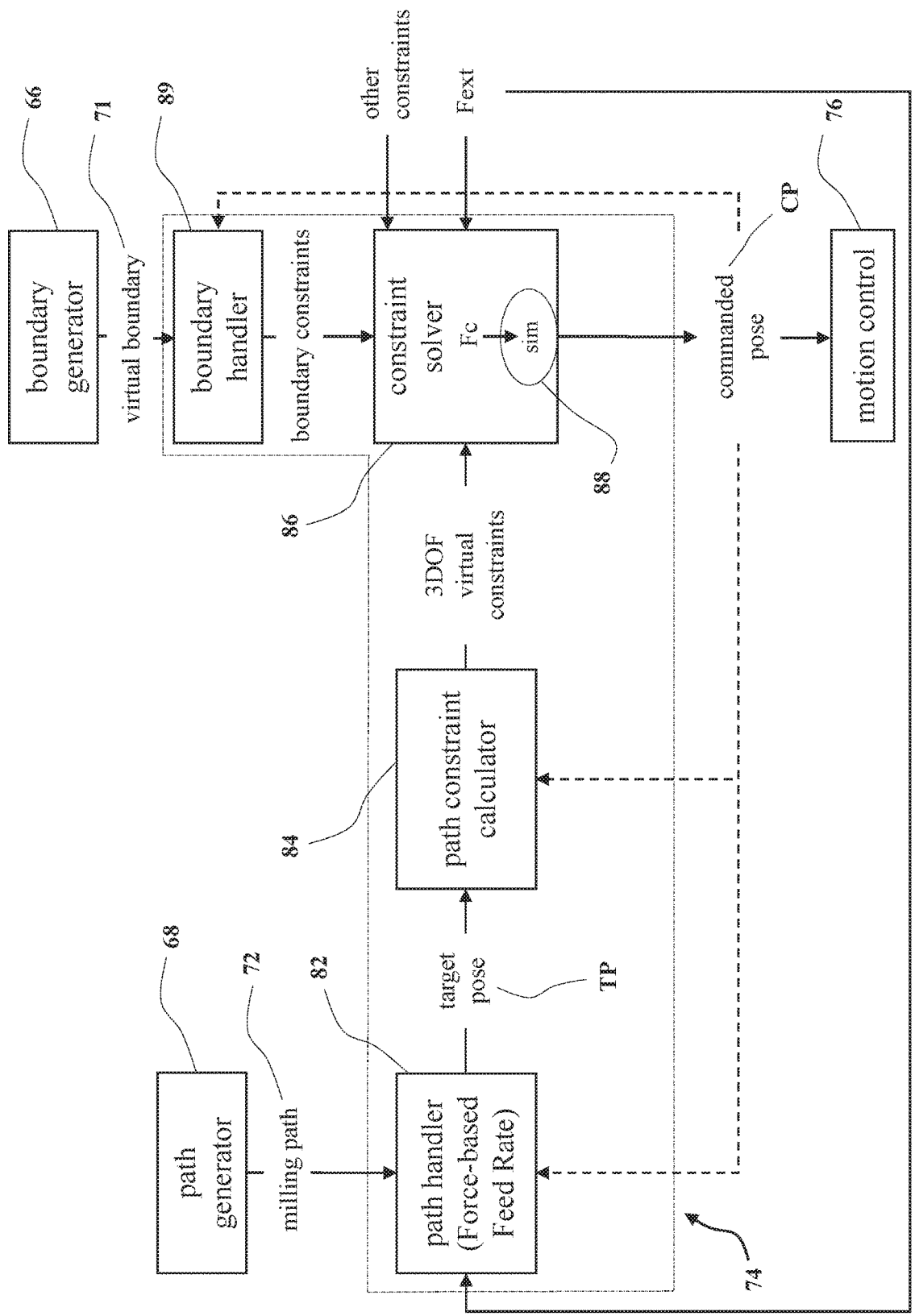
FIG. 20 is a block diagram of modules operable by the control system.

FIG. 20 illustrates processes carried out to execute the guided-manual mode in another example. In this example, the behavior control 74 comprises the path handler 82, the path constraint calculator 84, the constraint solver 86, and the virtual simulator 88. The path handler 82, path constraint calculator 84, constraint solver 86, and the virtual simulator 88 each comprises executable software stored in a non-transitory memory of any one or more of the aforementioned controllers and implemented by the control system 60.

Figure 21:
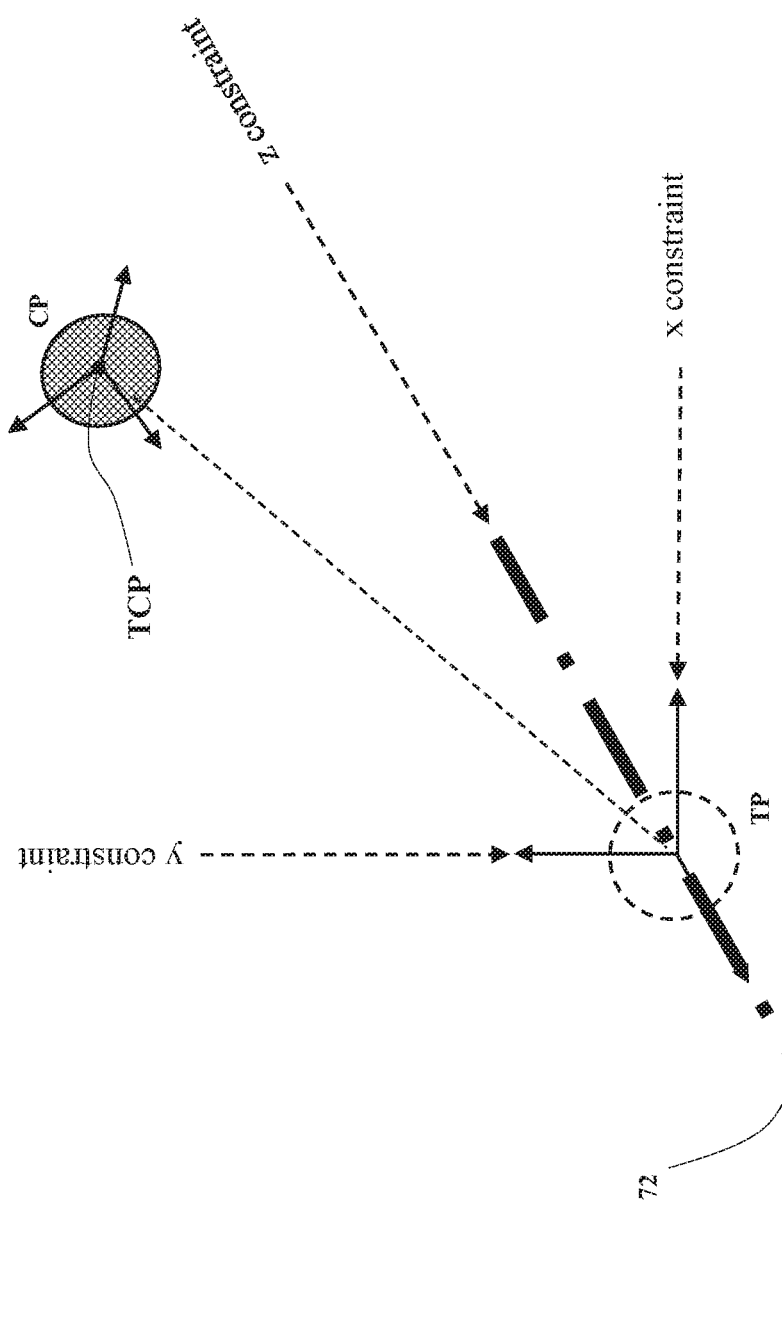
FIG. 21 is an illustration of the milling path, showing virtual constraints in x, y, and z directions with respect to a constraint coordinate system.

In this version, the path handler 82 receives three inputs: the milling path 72, the previous commanded pose CP, and the external force $F_{ext}$. The path handler 82 processes these inputs to determine a constraint application pose, at which to define three virtual constraints (x constraint, y constraint, z constraint), as illustrated in FIG. 21. In this version, the constraint application pose is a target pose TP with its origin located on the milling path 72 to which it is desired to move the TCP of the tool 20. The same convention for locating the axes of the constraint application pose on the milling path 72 described above could be employed in this version as well to locate the axes of the target pose TP on the milling path 72. Other conventions are also possible. Ideally, the next commanded pose CP coincides with the target pose TP. Of course, in certain cases, the next commanded pose CP may not coincide with the target pose TP. The external force $F_{ext}$ is utilized by the path handler 82 to determine a virtual feed rate of the TCP of the tool 20, which is then used by the path handler 82 to determine the next target pose TP. The origin of the next target pose TP is also located on the milling path 72.

Additional constraints could also be used beyond the x, y, z constraints. For example, additional constraints could be used so that the target pose is also encoded with a desired orientation in one or more of the rotational degrees of freedom. In that case, one or more of the axes for the target pose TP could be chosen to give the desired orientation of the TCP coordinate frame (for that point on the milling path 72). Accordingly, more than three virtual constraints would be computed by the path constraint calculator 84 for both the position and orientation components. Thus, the guided-manual mode may assist users in guiding the TCP of the tool 20 along the milling path 72, while also guiding the orientation of the tool 20 in one or more degrees of freedom. Path-defined orientations could be computed/determined by the path generator 68, either offline or during the procedure, based on the surgical approach, clinical access, etc., and passed into the path handler 82 as part of the milling path 72, such that the orientation of the tool 20 automatically changes in a desirable/predefined way as the user slides the TCP of the tool 20 along the milling path 72. Alternatively, or additionally, a set of orientation constraints could be determined independently of the path constraint calculator 84 and passed into the constraint solver 86 as part of the 'other constraints' input. One example for this approach would be to have a 2-DOF set of orientation constraints (e.g., for a spherical bur) to keep the bur shaft within a predefined virtual aperture, as described in U.S. Pat. No. 9,566,122, hereby incorporated herein by reference. Other options for orientation control are possible, such as no orientation control whereby the user is able to freely reorient the tool 20. These examples of orientation control could be employed in this version, the versions of FIG. 8 or 10, or in other embodiments. Thus, two or three virtual constraints for the TCP position could come from the path constraint calculator 84 (see, e.g., FIGS. 10 and 20), and additional constraints could be provided by an independent orientation control source. The position and orientation constraints, or individual constraints, can have different stiffness/damping tuning to give a desired user interaction and feel. The constraint solver 86 solves the full set of constraints and outputs a commanded pose CP to the motion control 76.

At each iteration of the process shown in FIG. 20, which may be carried out at any suitable frame rate (e.g., every 125 microseconds), the path handler 82 calculates a tangential component $F_{ext}$ (tan) of the external force $F_{ext}$ that is tangential to the milling path 72 at the origin of the previous commanded pose CP. This tangential component of force $F_{ext}$ (tan) at least partially dictates how far along the milling path 72 the tool 20 should move. Said differently, since this tangential component of force $F_{ext}$ (tan) is at least partially derived by how much force the user applied in the tangential direction (e.g., to move the tool 20 in the tangential direction), it largely defines how far to move the tool 20 along the milling path 72.

Once the tangential component $F_{ext}$ (tan) of the external force $F_{ext}$ is determined, according to some examples, the tangential component $F_{ext}$ (tan) is fed into the equation $F_{ext}$ (tan)=(Vm)*(a) referenced above with respect to FIG. 8 to define an effective feed rate along the milling path 72, e.g., by integrating the acceleration over the time step (e.g., 125 microseconds), and to determine how far along the milling path 72 to place the origin of the target pose TP by integrating the effective feed rate (velocity) over the same time step. It should be appreciated that the effective feed rate (velocity) could be combined with other feed rate sources before determining the location of the target pose TP, such as the feed rate sources described in U.S. Pat. No. 9,566,122, hereby incorporated herein by reference.

$F_{ext}$ (tan) can be computed so that a positive value is in a forward path direction and a negative value is in a negative path direction. The integrations can thus be performed in a manner yielding the direction of the tangential distance. For example, a negative distance indicates to move backwards along the milling path 72. In some cases, it may not be desired to allow the user to move backwards along the milling path 72. In that case, if the tangential distance computed is negative, it may be limited at zero.

Once the tangential distance and direction is determined (see FIG. 22, for example), the path handler 82 then steps iteratively within a time step along the milling path 72, one path segment PS at a time, until the accumulated distance stepped along the milling path 72 (e.g., path distance) is equal to the tangential distance. This iterative process may include the path handler 82 repeatedly checking if the next segment's distance would exceed the computed tangential distance, and if so, the path handler 82 then interpolates linearly within that path segment PS to determine the precise location along the path segment PS where the tangential distance is reached. This location becomes the origin of the next target pose TP. FIG. 23B, for example, illustrates the tangential distance being greater than a distance of one full path segment 1PS, but shorter than the distance of two path segments 1PS, 2PS. Accordingly, the path handler 82 would linearly interpolate along the second path segment 2PS to determine the precise location along the second path segment 2PS where the tangential distance is reached and this becomes the next target pose TP. It may also help to imagine the tangential distance being folded over onto the second path segment 2PS as illustrated by the arrow in FIG. 23B. This iterative path interpolation process may also include smoothing filters on the interpolated path points, either time domain or spatial, acceleration filters, etc., before setting the result as the origin of the next target pose TP. The target pose TP is then sent to the path constraint calculator 84 to compute the three virtual constraints. In this example, these virtual constraints include x, y, z virtual constraints to be applied to effectively move the tool 20 from the current commanded pose CP of the tool 20 to the target pose TP (more or less constraints are also possible). These three constraints are computed based on the difference between the current commanded pose and the target pose TP. Of course, in other versions, orientation constraints could also be defined based on differences between current orientations and desired orientations.

The three virtual constraints defined by the path constraint calculator 84 are next input into the constraint solver 86 (possibly with boundary constraints and/or other constraints, as shown in FIG. 20) to be processed by the constraint solver 86 to determine the resulting constraint force $F_c$ in the same manner as previously described. The virtual simulator 88 then carries out a virtual simulation in the same manner previously described to ultimately determine a next commanded pose CP.

Figure 22:
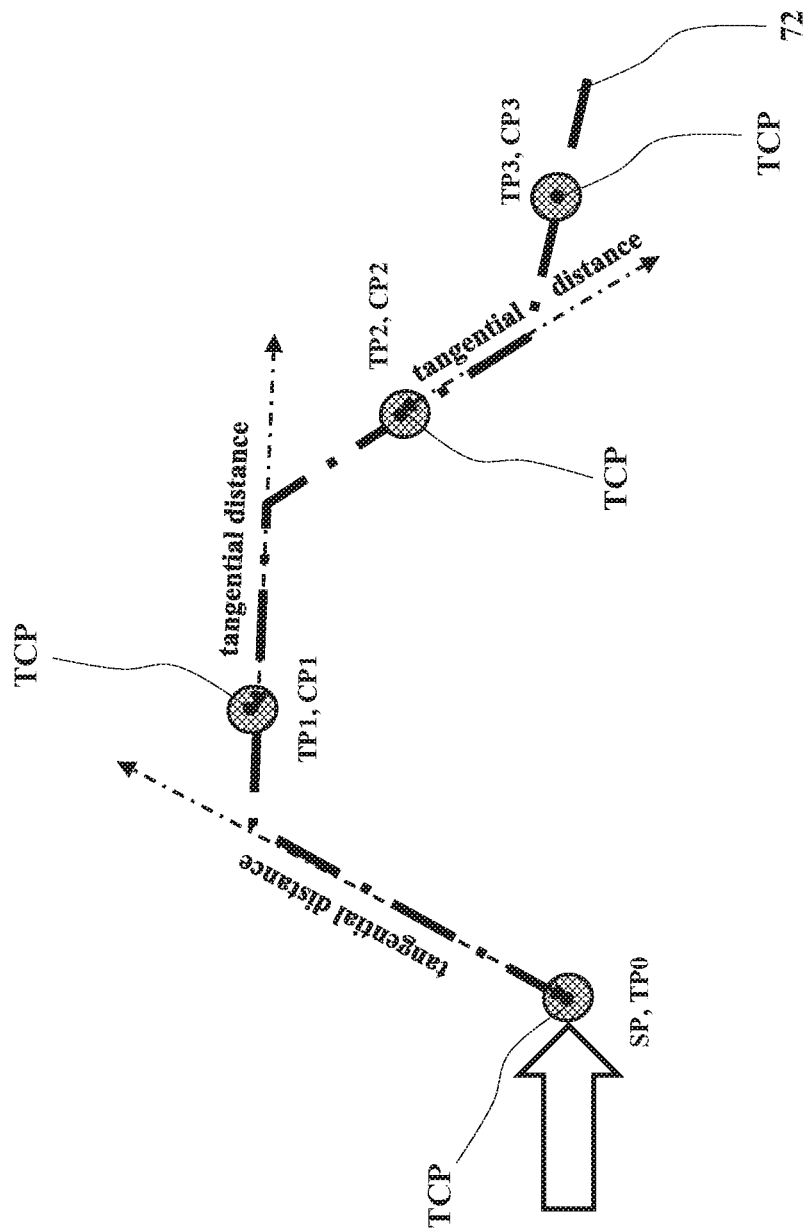
FIG. 22 illustrates a series of movements of the surgical tool along another milling path using the modules of FIG. 20.
Figure 23B:
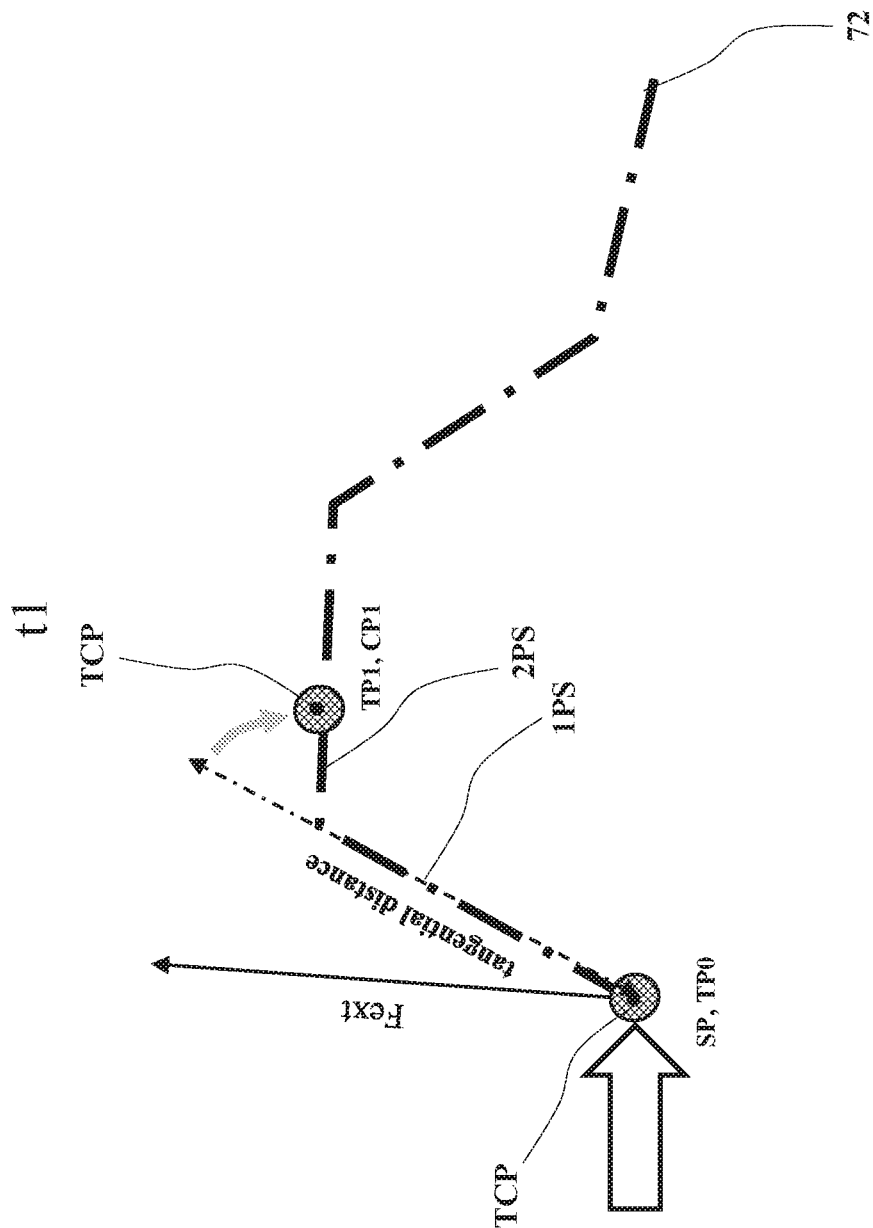
Figure 23C:
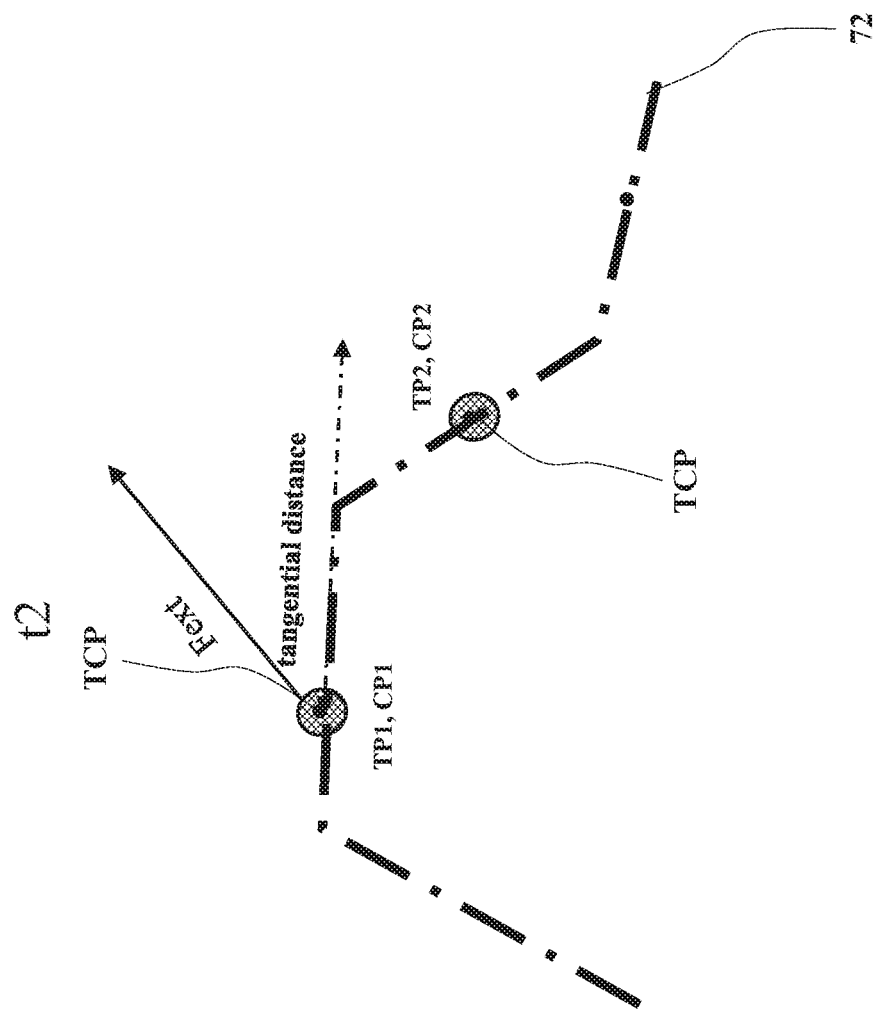
Figure 23D:
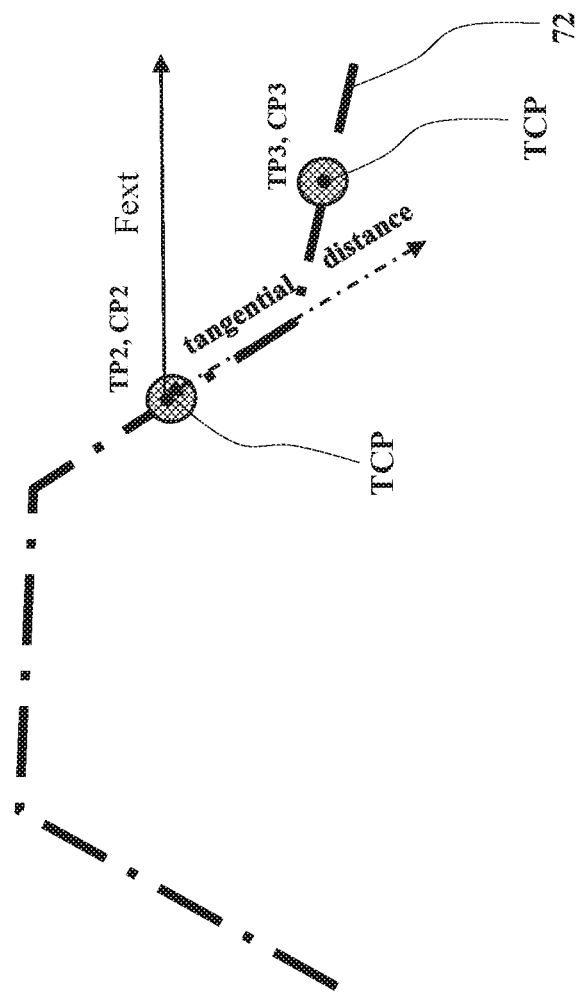

FIG. 22 illustrates motion of the TCP of the tool 20 along the milling path 72 in the guided-manual mode for this example from the starting point SP to a first commanded pose CP1, then to a second commanded pose CP2, and finally to a third commanded pose CP3. Along the way, the control system 60 executes the process set forth in FIG. 20 to determine the series of target poses TP1, TP2, TP3, so that the control system 60 is able to determine each subsequent commanded pose CP in the virtual simulation. Again, although the commanded poses CP1, CP2, CP3 are shown to coincide with the target poses TP1, TP2, TP3, this may not always be the case.

It should be appreciated that a lead-in path could be employed in the manner described above to guide the user to the starting point SP. From the starting point SP, upon the user manually applying forces and torques to the tool 20, the external force $F_{ext}$ is determined via the force/torque sensor S and the path handler 82 receives the external force $F_{ext}$ to compute the effective feed rate and associated tangential distance to be traversed along the milling path 72 to define the first target pose TP1. Once the first target pose TP1 is defined, the path constraint calculator 84 then calculates the three virtual constraints to ultimately cause movement of the tool 20 to/toward the target pose TP1. The constraint solver 86 and virtual simulator 88 operate as before to determine each subsequent commanded pose.

FIGS. 23A through 23D show the process being carried out from an initial time (t0) to a final time (t3). As the milling path 72 is incrementally interpolated using the process of FIG. 20, segments are traversed up until you reach the respective end of the milling path 72, at which point the target pose TP no longer updates in that direction. If a firm end-of-path behavior is not desired (i.e., if it's desired for the user to "fall off" the ends), an alternate approach would be to turn off one or more of the virtual constraints when an end-of-path target is reached (as determined by the path handler 82), allowing the tool 20 to move freely. This behavior could be accompanied by user feedback on the displays 38, audible feedback, and/or haptic feedback.

A user pendant, separate from the tool 20, or other user interface UI (e.g., on the tool 20) may be employed to switch between the various modes of operation of the manipulator 14. The control system 60 may be configured to automatically switch modes in certain situations. For example, if the control system 60 was operating the manipulator 14 in the semi-autonomous mode initially, prior to switching to the guided-manual mode, the control system 60 may automatically restart the semi-autonomous mode once the user switches off the guided-manual mode. The control system 60 may also first prompt the user before automatically continuing in the semi-autonomous mode, such as by providing selectable prompts on one or more of the displays 38 to continue in the semi-autonomous mode. The user may select to continue in the manual mode, semi-autonomous mode, etc. The control system 60, if transitioning to the semi-autonomous mode from the guided-manual mode, may first calculate a transition path to the milling path 72, which may be the shortest distance from the current position of the TCP to the milling path 72, and then utilize this transition path as a form of lead-in path to resume movement along the milling path 72. Upon this transition from the guided-manual mode to the semi-autonomous mode (or upon transition from the manual mode to the guided-manual mode), it may be desirable to re-compute the milling path 72 based on what volume of tissue was removed in the guided-manual mode and/or the manual mode (or alternatively, based on which volume of tissue is remaining), to have an optimized/cleaned up milling path 72, reduced machining time, less air cutting, etc. Logging the volume of tissue removed, such as during the manual mode, in order to re-compute a milling path and improve efficiency in the semi-autonomous mode is described in U.S. Pat. No. 9,566,122, hereby incorporated herein by reference. Those same principles can be applied here when transitioning from the guided-manual mode to the semi-autonomous mode or from the manual mode to the guided-manual mode.

When the control system 60 is operating in the semi-autonomous mode and the user instructs the control system 60 to switch to the guided-manual mode, or when the control system 60 automatically switches to the guided-manual mode, the control system 60 records the last position on the milling path 72 that the tool 20 occupied in the semi-autonomous mode before switching to the guided-manual mode. After moving along the milling path 72, in guided-manual mode as desired, the tool 20 is in a different position on the milling path 72 than the last recorded position. The control system 60, when switching back to the semi-autonomous mode, can return back to the last recorded position to pick up where the semi-autonomous mode left off. In some versions, the lead-in path 72a described above may be used in the guided-manual mode to reach the starting point SP, which is the starting point SP for semi-autonomous machining. In this case, once the tool 20 is at the starting point SP, then semi-autonomous operation can start automatically or following user prompting and selection.

The current pose of the tool 20 relative to the milling path 72 and/or relative to the surgical site may be output by the navigation system 32 and represented on the displays 38 via graphical representations of the tool 20, virtual boundaries 71, milling path 72, and/or the surgical site, e.g., the femur F or other anatomy. These graphical representations may update in real-time so that the user is able to visualize their progress in the guided-manual mode relative to the complete milling path 72 or portions of the milling path 72. For example, the graphical representations of the tool 20 and anatomy may move on the displays 38 in real-time with actual movement of the tool 20 by the manipulator 14 and the anatomy. The milling path 72 can also be updated as described above to show the user the portions/segments of the milling path 72 already traversed by the tool 20 in the guided-manual mode. These can be differentiated from portions/segments that still need to be traversed, such as by rendering them different colors, line types, graying out or removing the traversed portions/segments, or the like.

The TCP of the tool 20, and/or other portions of the tool 20, may be additionally, or alternatively, constrained to the milling path 72 by employing virtual boundaries along and/or around the milling path 72. Such virtual boundaries 90, 92 are shown in FIGS. 24 and 25. These virtual boundaries may represent tubes disposed about the milling path 72 with an entrance 94 and an exit 96. The entrance 94 and/or the exit 96 of the virtual boundaries 90, 92 may be funnel-shaped or other shape to facilitate entrance of the tool 20 into the virtual boundary 90, 92. These virtual boundaries 90, 92 may constrain movement of the tool in a manner similar to that disclosed in U.S. Pat. No. 9,119,655, incorporated herein by reference, or as described in U.S. Pat. No. 8,010, 180, hereby incorporated herein by reference.

In this embodiment, the TCP of the tool 20 may be modeled as a sphere and a tube-shaped triangle mesh surface (with the tube having the same, approximately the same, or slightly larger diameter as the tool's sphere model) may be created that traverses the milling path 72. This mesh surface can be created ahead of time (offline), but could be generated on-the-fly, such as by the boundary generator. Mesh density may be high enough (e.g., small enough triangles, typically 0.1 to 1.0 mm on a side) such that the triangle mesh sufficiently and smoothly represents a tube surface, resulting in a smooth feel as the tool 20 is slid down the tube.

When using these models in the guided-manual mode, velocity constraints are generated from each active mesh triangle (with each constraint acting along the normal vector of its corresponding mesh triangle) that prevent the tool 20 from escaping the tube once it enters. However, the tool 20 can slide freely in either direction down the length of the tube (constraints are normally not defined in these directions). The velocity constraints generated in this case would typically be passed into the constraint solver 86 as part of the boundary constraints output from the boundary handler 89. Accordingly, in this embodiment, the path generator 68, path handler 82, and path constraint calculator 84 may be absent. Optionally, additional damping forces and/or damping constraints can be added to add/create damping along the tube surface if desired (e.g., for machining stability, feel, user preference, etc.). The constraints are passed into the constraint solver 86 and solved (possibly with other active constraints) by the constraint solver 86, generating a constraint force Fc, which is summed by the virtual simulator along with other forces ($F_{cgext}$, $F_{damping}$, $F_{inertial}$) applied to the virtual rigid body, and forward dynamics performed to get a resulting commanded pose CP.

The tube can have a three-dimensionally curved path. This may be useful, for example, to assist in creating a helical motion for peg hole machining, e.g., allowing the user to use a small bur to more easily machine a larger diameter hole by following a helical path. A helical-shaped mesh can be generated having a much smaller diameter than the physical bur, to prevent the mesh from intersecting with itself, with the sphere representing the tool 20 having the same smaller diameter. By choosing an appropriate slope/pitch for the helical tube, the user only needs to apply gentle downward force and the tool 20 slides its way down the helix. The mesh can be created as shown in FIG. 29 with a funnel shaped opening to guide the user to the entrance 94 of the tube and lead to the exit 96 that guides the user to pull the tool straight up following machining.

Figure 26:
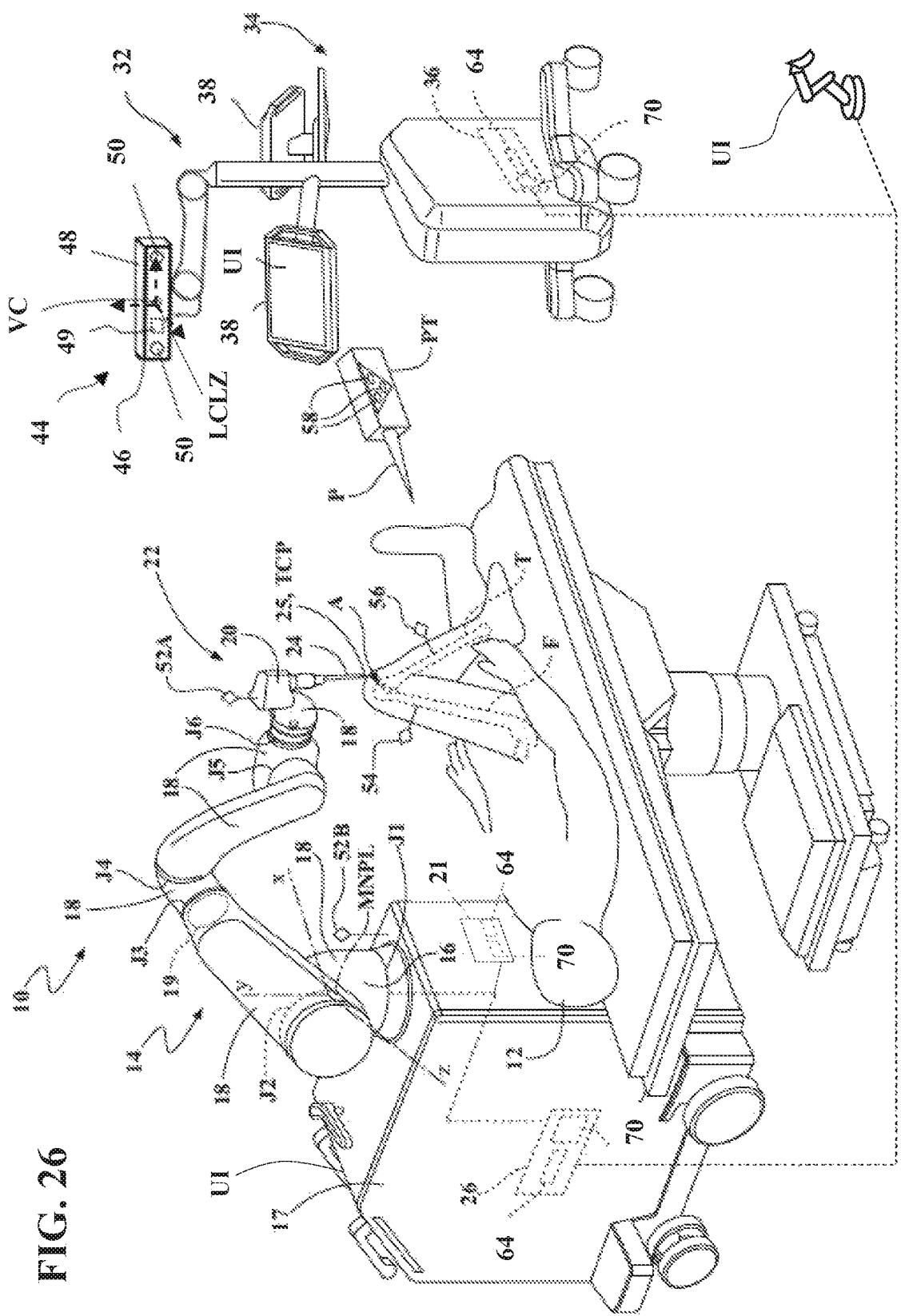
FIG. 26 is a perspective view of a tele-manipulated robotic surgical system.

Referring to FIG. 26, the guided-manual mode described herein may be employed in various types of robotic systems. For example, the manipulator 14 may comprise a tele-manipulated robotic arm that is controlled via a user interface UI that is remotely located relative to the tele-manipulated robotic arm to control the tele-manipulated robotic arm. The user interface UI may comprise a separate manipulator such as a 6-DOF control unit that is manually manipulated by a user, e.g., a separate manipulator with active joints to provide haptic feedback to the user. During a free mode, the tele-manipulated robotic arm mimics the motion imparted to the user interface UI by the user. For example, the user interface UI may comprise the same linkage and joint configuration as the tele-manipulated robotic arm and movement of one or more links on the user interface UI cause movement of the corresponding links on the tele-manipulated robotic arm. In some embodiments, this coordinated movement may be at different scaling factors (e.g., a 1 mm movement of a link of the user interface UI may correlate to a 10 mm movement of the same link of the tele-manipulated robotic arm).

During the guided-manual mode, the tele-manipulated robotic arm is controlled by the manipulator controller 26 to keep the tool 20 on the milling path 72. This may be accomplished by restricting available movements of the user interface UI in a manner that causes the tele-manipulated robotic arm to only be moved in a manner that keeps the tool 20 on the milling path 72. Such restriction could be performed via the virtual constraints described above being applied to the user interface UI, and by extension such constraints would effectively be applied to the tele-manipulated robotic arm owing to the tele-manipulated robotic arm being cooperatively connected to the user interface UI to move in the same manner, albeit at potentially different scaling factors. Additionally, or alternatively, the user interface UI may be freely moved by the user, but the manipulator controller 26 effectively ignores those movements of the user interface UI that would otherwise correspond to moving the tool 20 off the milling path 72 and the manipulator controller 26 only reacts to corresponding movements from the user interface UI that would keep the tool 20 on the milling path 72.

Several embodiments have been described in the foregoing description. However, the embodiments discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The invention claimed is:

1. A robotic surgical system comprising:
   a surgical tool;
   a manipulator configured to support the surgical tool, the manipulator comprising a plurality of links;
   a force/torque sensor to measure forces and torques applied to the surgical tool; and
   a control system configured to:
     obtain a milling path for the surgical tool wherein the milling path is three-dimensional and predetermined;
     define virtual constraints to constrain movement of the surgical tool to be along the milling path, wherein the virtual constraints are defined with respect to two degrees of freedom each being normal to the milling path, and wherein movement of the surgical tool with respect to one degree of freedom tangential to the milling path is unconstrained by the virtual constraints;
     receive an input from the force/torque sensor in response to user forces and torques manually applied to the surgical tool by a user;
     simulate dynamics of the surgical tool in a virtual simulation based on the virtual constraints and the input from the force/torque sensor; and
     command the manipulator to advance the surgical tool along the milling path based on the virtual simulation.

2. The robotic surgical system of claim 1 wherein the control system is further configured to simulate dynamics of the surgical tool by representing the surgical tool as a virtual rigid body having a virtual mass and by applying a constraint force to the virtual mass in the virtual simulation to yield a commanded pose, wherein the constraint force is based on the virtual constraints.

3. The robotic surgical system of claim 1, wherein the control system is configured to determine a first commanded pose based on the virtual simulation and to calculate a first constraint application pose on the milling path that is at a point nearest to the first commanded pose.

4. The robotic surgical system of claim 3, wherein the control system is configured to determine the point nearest to the first commanded pose by: performing a broad-phase search to determine a subset of path segments within a specified distance of the first commanded pose; performing a narrow-band search to compute a normal line and a length of the normal line from the first commanded pose to each of the path segments of the subset determined in the broad-phase search; and selecting the normal line that has the length that is shortest.

5. The robotic surgical system of claim 3, wherein the control system is configured to:
define first virtual constraints with respect to the two degrees of freedom normal to the milling path based on a distance between the first commanded pose and the first constraint application pose, wherein the first virtual constraints are defined at the first constraint application pose;
determine a second commanded pose based on the first virtual constraints; and
command the manipulator to move to the second commanded pose.

6. The robotic surgical system of claim 1, wherein the control system is configured to calculate a tangential component of force tangential to the milling path based on the input from the force/torque sensor.

7. The robotic surgical system of claim 1, wherein the control system is configured to:
determine a first commanded pose based on the virtual simulation;
calculate a first constraint application pose on the milling path based on a distance between the first commanded pose and a previous commanded pose, the distance being projected onto the milling path to compute a point on the milling path at which to define the first constraint application pose;
define first virtual constraints with respect to the two degrees of freedom normal to the milling path based on a distance between the first commanded pose and the first constraint application pose;
define the first virtual constraints with respect to the two degrees of freedom normal to the milling path at the first constraint application pose;
determine a second commanded pose based on the first virtual constraints; and
command the manipulator to move to the second commanded pose.

8. The robotic surgical system of claim 1, wherein the manipulator is operable in a guided-manual mode and a semi-autonomous mode and wherein the control system is further configured to utilize the virtual constraints in the guided-manual mode.

9. The robotic surgical system of claim 8, in response to transitioning to the semi-autonomous mode from the guided-manual mode, the control system is configured to calculate a transition path from a current position of a tool center point of the surgical tool to a last known point of the surgical tool on the milling path before transitioning from the semi-autonomous mode.

10. The robotic surgical system of claim 1, wherein the control system is configured to:
define a starting position for the surgical tool on the milling path;
determine a current position of the surgical tool; and
define a lead-in path from the current position of the surgical tool to the starting position of the milling path.

11. The robotic surgical system of claim 1, wherein the control system is configured to:
track locations at which the surgical tool has been applied to an anatomy;
track locations at which the surgical tool has not been applied to the anatomy; and
define the milling path along one or more of the locations at which the surgical tool has not been applied to the anatomy.

12. The robotic surgical system of claim 1, wherein the control system is configured to determine a direction of movement to move the surgical tool along the milling path based on the input from the force/torque sensor, the surgical tool being movable in opposing directions along the milling path.

13. The robotic surgical system of claim 12, wherein the control system is configured to define an end constraint with respect to one degree of freedom tangential to the milling path to constrain the surgical tool to remain on the milling path by constraining movement beyond an end of the milling path, and wherein the control system is configured to perform one or more of the following:
provide an indication of when to apply the end constraint; and
disable the virtual constraints based on reaching an end of the milling path.

14. The robotic surgical system of claim 1, wherein the virtual constraints are defined as velocity constraints, wherein each of the velocity constraints comprises stiffness and damping parameters and one or more force limits and one or more activation limits.

15. The robotic surgical system of claim 1, wherein the control system is configured to:
obtain a virtual boundary for the surgical tool with the virtual boundary being three-dimensional tube defining the milling path; and
define virtual constraints on movement of the surgical tool inside the tube and along the milling path, the virtual constraints being defined to constrain movement of the surgical tool to be along the milling path.

16. A method for operating a robotic surgical system, the robotic surgical system comprising a surgical tool, a manipulator configured to support the surgical tool, and a force/torque sensor to measure forces and torques applied to the surgical tool, the method comprising the steps of:
obtaining a milling path for the surgical tool wherein the milling path is three-dimensional and predetermined;
defining virtual constraints to constrain movement of the surgical tool to be along the milling path, wherein the virtual constraints are defined with respect to two degrees of freedom each being normal to the milling path, and wherein movement of the surgical tool with respect to one degree of freedom tangential to the milling path is unconstrained by the virtual constraints;
receiving input from the force/torque sensor in response to user forces and torques manually applied to the surgical tool by a user;
simulating dynamics of the surgical tool in a virtual simulation based on the virtual constraints and the input from the force/torque sensor; and
commanding the manipulator to advance the surgical tool along the milling path based on the virtual simulation.

17. The method of claim 16 wherein simulating the dynamics of the surgical tool in a virtual simulation comprises representing the surgical tool as a virtual rigid body having a virtual mass and applying a constraint force to the virtual mass in the virtual simulation to yield a commanded pose, wherein the constraint force is based on the virtual constraints.

18. The method of claim 16, comprising determining a first commanded pose based on the virtual simulation and calculating a first constraint application pose on the milling path that is at a point nearest to the first commanded pose.

19. The method of claim 18, wherein determining the point nearest to the first commanded pose comprises: performing a broad-phase search to determine a subset of path segments within a specified distance of the first commanded pose; performing a narrow-band search to compute a normal line and a length of the normal line from the first commanded pose to each of the path segments of the subset determined in the broad-phase search; and
  selecting the normal line that has the length that is shortest.

20. The method of claim 18, comprising:
  defining first virtual constraints with respect to the two degrees of freedom normal to the milling path based on a distance between the first commanded pose and the first constraint application pose, wherein the first virtual constraints are defined at the first constraint application pose;
  determining a second commanded pose based on the first virtual constraints; and
  commanding the manipulator to move to the second commanded pose.

21. The method of claim 16, comprising calculating a tangential component of force tangential to the milling path based on the input from the force/torque sensor.

22. The method of claim 16, comprising:
  determining a first commanded pose based on the virtual simulation;
  calculating a first constraint application pose on the milling path based on a distance between the first commanded pose and a previous commanded pose, the distance being projected onto the milling path to compute a point on the milling path at which to define the first constraint application pose;
  defining first virtual constraints with respect to the two degrees of freedom normal to the milling path based on a distance between the first commanded pose and the first constraint application pose;
  defining the first virtual constraints with respect to the two degrees of freedom normal to the milling path at the first constraint application pose;
  determining a second commanded pose based on the first virtual constraints; and
  commanding the manipulator to move to the second commanded pose.

23. The method of claim 16, wherein the manipulator is operable in a guided-manual mode and a semi-autonomous mode and further comprising defining the virtual constraints in the guided-manual mode.

24. The method of claim 23, wherein in response to transitioning to the semi-autonomous mode from the guided-manual mode, further comprising calculating a transition path from a current position of a tool center point of the surgical tool to a last known point of the surgical tool on the milling path before transitioning from the semi-autonomous mode.

25. The method of claim 16, comprising:
  defining a starting position for the surgical tool on the milling path;
  determining a current position of the surgical tool; and
  defining a lead-in path from the current position of the surgical tool to the starting position of the milling path.

26. The method of claim 16, comprising:
  tracking locations at which the surgical tool has been applied to an anatomy;
  tracking locations at which the surgical tool has not been applied to the anatomy; and
  defining the milling path along one or more of the locations at which the surgical tool has not been applied to the anatomy.

27. The method of claim 16, comprising determining a direction of movement to move the surgical tool along the milling path based on the input from the force/torque sensor, the surgical tool being movable in opposing directions along the milling path.

28. The method of claim 27, comprising defining an end constraint with respect to one degree of freedom tangential to the milling path to constrain the surgical tool to remain on the milling path by constraining movement beyond an end of the milling path, and further performing one or more of the following:
  providing an indication of when to apply the end constraint; and
  disabling the virtual constraints based on reaching an end of the milling path.

29. The method of claim 16, comprising defining the virtual constraints as velocity constraints, wherein each of the velocity constraints comprises stiffness and damping parameters and one or more force limits and one or more activation limits.

30. The method of claim 16, comprising:
  obtaining a virtual boundary for the surgical tool with the virtual boundary being three-dimensional tube defining the milling path; and
  defining virtual constraints on movement of the surgical tool inside the tube and along the milling path, the virtual constraints being defined to constrain movement of the surgical tool to be along the milling path.

* * * * *